US008809019B2

(12) United States Patent
Sibbesen et al.

(10) Patent No.: US 8,809,019 B2
(45) Date of Patent: Aug. 19, 2014

(54) MICROORGANISM EXPRESSING ALDOSE-1-EPIMERASE

(75) Inventors: Ole Sibbesen, Bagsärd (DK); Birgitte Rönnow, Copenhagen K (DK); Thomas Hvid Andersen, Frederiksberg (DK)

(73) Assignee: Terranol A/S (DK)

( * ) Notice: Subject to any disclaimer, the term of this patent is extended or adjusted under 35 U.S.C. 154(b) by 627 days.

(21) Appl. No.: 13/000,723

(22) PCT Filed: Jul. 3, 2009

(86) PCT No.: PCT/IB2009/052916
§ 371 (c)(1),
(2), (4) Date: Dec. 22, 2010

(87) PCT Pub. No.: WO2010/001363
PCT Pub. Date: Jan. 7, 2010

(65) Prior Publication Data
US 2011/0099892 A1 May 5, 2011

Related U.S. Application Data

(60) Provisional application No. 61/081,535, filed on Jul. 17, 2008.

(30) Foreign Application Priority Data

Jul. 4, 2008 (GB) .................................. 0812318.4

(51) Int. Cl.
*C12N 9/92* (2006.01)
(52) U.S. Cl.
USPC .......................................... 435/70.1; 435/105
(58) Field of Classification Search
USPC .................................. 435/105, 243
See application file for complete search history.

(56) References Cited

U.S. PATENT DOCUMENTS

| 5,508,176 A | 4/1996 | Hillen et al. |
| 2005/0208636 A1 | 9/2005 | Wahlbom et al. |

FOREIGN PATENT DOCUMENTS

| WO | WO 91/17243 A1 | 11/1991 |
| WO | WO 03/062430 A1 | 7/2003 |
| WO | WO 2005/023998 A1 | 3/2005 |
| WO | WO 2005/091733 A2 | 10/2005 |
| WO | WO 2005/113774 A3 | 12/2005 |
| WO | WO 2006/009434 A1 | 1/2006 |
| WO | WO 2006/096130 A1 | 9/2006 |
| WO | WO 2008/041840 A1 | 4/2008 |

OTHER PUBLICATIONS

Gatz et al., Cloning and Expression of the *Acinetobacter calcoaceticus* Mutarotase Gene in *Escherichia coli*. Journal of Bacteriology, 168: p. 31-39, 1986.*

Hahn-Hagerdal et al. Toward industrial pentose-fermenting yeast strains. Appl. Microbial. Biotechnol. 74: 937-953, 2007.*
Gatz, Christiane et al., "Cloning and Expression of the *Acinetobacter calcoaceticus* Mutarotase Gene in *Escherichia coli*" Journal of Bacteriology, Oct. 1986, vol. 168, No. 1, p. 31-39. XP-002550762.
Jong-Hoon, Lee et al., "Expression of the Galactose Mutarotase Gene from *Lactococcus lactis* ATCC7962 in *Eshcherichia coli*"Database Biosis, Biosciences Information Services, Dec. 2000, XP002550763, Abstract, 1 page.
Scott, Aaron et al., "Characterization of the *Saccharomyces cerevisiae* galactose mutarotase/UDP-galactose 4-epimerase protein, Gal10p", FEMS Yeast Research, vol. 7, No. 3, May 2007, p. 366-371. XP-002550761.
International Search Report, PCT/IB2009/052916, Terranol A/S, dated Oct. 30, 2009, 5 pages.
Anderson, R. L. And Allison D. P., "Purification and Characterization of D-Lyxose Isomerase". J. Biol. Chem. (1965) 240, 2367-2372.
Bailey, J. M., Fishman P. H., and Pentchev P. G., "Studies on Mutarotases. III. Isolation and characterization of a mutarotase from bovine kidney cortex". (1969) J. Biol. Chem. 244, 781-788.
Becker, D. M. and Guarente L. "High-efficiency transformation of yeast by electroporation". (1991) Methods Enzymol. 194, 182-187.
Brahma A. and Bhattacharyya D. "UDP-galactose 4-epimerase from *Kluyveromyces fragilis*". (2004) Evidence for independent mutarotation site. Eur. J. Biochem. 271, 58-68.
Burnett, M. E., Liu J., and Conway T. "Molecular Characterization of the *Zynnomonas mobilis* Enolase (eno)" (1992) Gene. J. Bact. 174, 6548-6553.
Cheng H., Jiang N., Shen A., and Feng Y. "Molecular cloning and functional expression of D-arabitol dehydrogenase gene from *Gluconobacter oxydans* in *Escherichia coli*". (2005) FEMS Microbiol. Lett. 252, 35-42.
Conway T., Sewell G. W., and Ingram L. O., "Glyceraldehyde-3-Phosphate Dehydrogenase Gene from *Zymomonas mobilis*: Cloning, Sequencing, and Identification of Promoter Region". (1987) J. Bact. 169, 5653-5662.
Dische, Z. and Borenfreund E. "A new spectrophotometric method for the detection and determination of keto sugars and trioses". (1951) J. Biol. Chem. 192, 583.
Dothie, J. M., Giglio J. R., Moore C. B., Taylor S. S., and Hartley B. S. "Ribitol dehydrogenase of *Klebsiella aerogenes*. Sequence and properties of wild-type and mutant strains". (1985) Biochem. J. 230, 569-578.
Eberts, T. J., Sample R. H. B., Glick M. R., and Gregory H. E. "A Simplified, Colorimetric Micromethod for Xylose in Serum or Urine, with Phloroglucinol". (1979) Clin. Chem. 25, 1440-1443.
Goldstein, A. L. and McCusker J. H. "Three New Dominant Drug Resistance Cassettes for Gene Disruption in *Saccharomyces cerevisiae*". (1999) Yeast 15, 1541-1553.
Güldener U., Heck S., Fiedler T., Beinhauer J., and Hegemann J. H. "A new efficient gene disruption cassette for repeated use in budding yeast", (1996) Nucleic Acids Res. 24, 2519-2524.
Izumori, K., Rees A. W., and Elbein A. D. "Purification,Crystallization, and Properties of D-Ribose Isomerase from *Mycobacterium smegmatis*". (1975) J. Biol. Chem. 250, 8085-8087.

(Continued)

*Primary Examiner* — Tekchand Saidha
*Assistant Examiner* — Rama P Ramanujam
(74) *Attorney, Agent, or Firm* — McKee, Voorhees & Sease

(57) ABSTRACT

A transformed microorganism capable of converting an aldopentose to a ketopentose at a higher rate than the equivalent microorganism prior to transformation.

3 Claims, 4 Drawing Sheets

(56) References Cited

OTHER PUBLICATIONS

Figure 1:
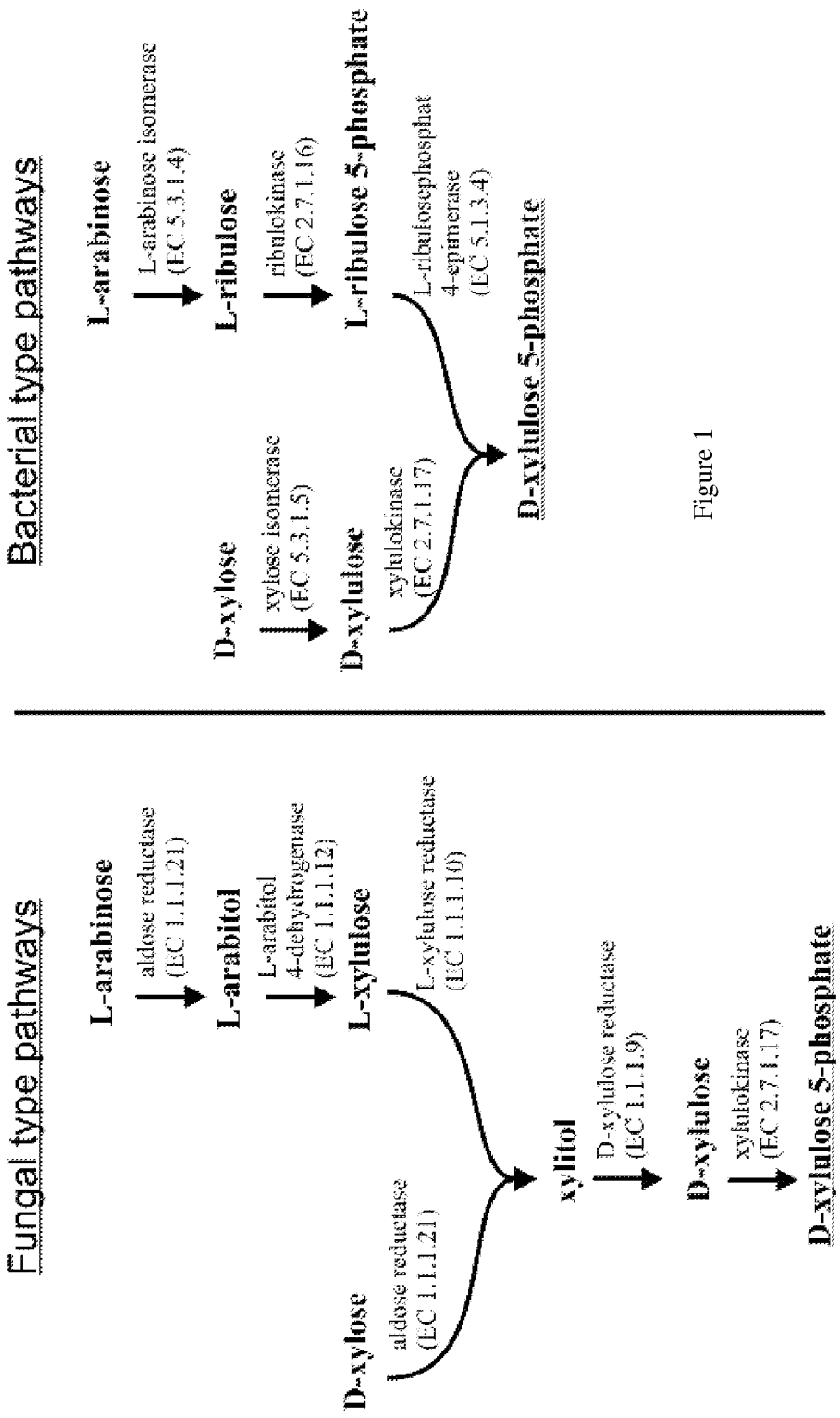

Kavanagh, K., Klimcek M., Nidetsky B., and Wilson D. K. "Structure of xylose reductase bound to NAD+ and the basis for single and dual co-substrate specificity in family 2 aldo-keto reductases". (2003) Biochem. J. 373, 319-326.

Majumdar, S., Ghatak J., Mukherji S., Bhattacharjee H., and Bhaduri A. "UDPgalactose 4-epimerase from *Saccharomyces cerevisiae*: A bifunctional enzyme with aldose 1-epimerase activity". (2004) Eur. J. Biochem. 271, 753-759.

Mumberg, D., Mailer R., and Funk M. "Yeast vectors for the controlled expression of heterologous proteins in different genetic backgrounds". (1995) Gene 156, 119-122.

Nakamura, Y., Gojobori T., and Ikemura T. "Codon Usage tabulated from international DNA sequence databases: status for the year 2000". (2000) Nucleic Acids Res. 28, 292.

Richard, P., Londesborough J., Putkonen M. Kalkkinen N., and Penttila M. "Cloning and Expression of a Fungal L-Arabinitol 4-Dehydrogenase Gene", (2001) J. Biol. Chem. 276, 40631-40637.

Rygus et al., "Inducible high-level expression of heterologous genes in *Bacillus megaterium* using the regulatory elements of the xylose-utilization", 1991, Applied Microbiol. Biotechnol., vol. 35, p. 594-599.

Ryu, K.-S., Kim C., Kim I., Yoo S., Choi B.-S., and Park C. "NMR Application Probes a Novel and Ubiquitous Family of Enzymes That Alter Monosaccharide Configuration". (2004) J. Biol. Chem. 279, 25544-25548.

Shimonishi, T. and Izumori K. "A new enzyme, L-ribose isomerase from *Acinetobacter* sp. strain DL-28". (1996) J. Ferment. Bioeng. 81, 493-497.

Verho, R., Putkonen M., Londesborough J., Penttila M., and Richard P. "A Novel NADH-linked L-Xylulose Reductase in the L-Arabinose Catabolic Pathway of Yeast". (2004) J. Biol. Chem. 279, 14746-14751.

Witteveen, C. F. B., Weber F., Busink R., and Visser J. "Isolation and characterisation of two xylitol dehydrogenases from *Aspergillus niger*". (1994) Microbiol. 140, 1679-1685.

Woodyer, R., Simurdiak M., van der Donk W. A., and Zhao H. "Heterologous Expression, Purification, and Characterization of a Highly Active Xylose Reductase from *Neurospora crassa*". (2005) Appl. Environ. Microbiol. 71, 1642-1647.

Yanese, H., Sato D., Yamamoto K., Matsuda S., Yamamoto S., and Okamoto K. "Genetic Engineering of *Zymobacter palmae* for Production of Ethanol from Xylose". (2007) Appl. Environ. Microbiol. 73, 2592-2599.

\* cited by examiner

US 8,809,019 B2

MICROORGANISM EXPRESSING ALDOSE-1-EPIMERASE

CROSS-REFERENCE TO RELATED APPLICATIONS

This is a National Phase application claiming priority to PCT/IB2009/052916 filed Jul. 3, 2009 which claims priority under 35 U.S.C. §119 to provisional application U.S. Ser. No. 61/081,535 filed Jul. 17, 2008, which claims priority to GB 0812318.4 filed Jul. 4, 2008, all of which are herein incorporated by reference in their entireties.

FIELD OF THE INVENTION

The present invention relates to a microorganism.

In particular, the present invention relates to a transformed microorganism capable of (i) converting an aldopentose to a ketopentose at a higher rate than the equivalent microorganism prior to transformation; and/or (ii) a higher growth rate in the presence of aldopentose than the equivalent microorganism prior to transformation; and/or (iii) a higher metabolism of aldopentose than the equivalent microorganism prior to transformation.

The present invention further relates to methods for preparing transformed microorganisms capable of: (i) producing a pentose derived compound; and/or (ii) converting an aldopentose to a ketopentose at a higher rate than the equivalent microorganism prior to transformation; and/or (iii) a higher growth rate in the presence of aldopentose than the equivalent microorganism prior to transformation; and/or (iv) a higher metabolism of aldopentose than the equivalent microorganism prior to transformation; said methods comprising the step of transforming a microorganism with a nucleotide sequence encoding an aldose-1-epimerase wherein said transformed microorganism is capable of converting an aldopentose to a ketopentose.

Further, the present invention relates to inoculums (inocula) and culture media comprising the microorganism according to the present invention or a microorganism prepared by a method according to the present invention.

The present invention additionally relates to methods for producing biofuel and/or a pentose derived compound comprising culturing a microorganism according to the present invention or a microorganism prepared by a method according to the present invention.

In addition, the present invention relates to a biofuel and/or a pentose derived compound obtained by a method of the present invention.

Further, the present invention relates to the use of a microorganism according to the present invention or prepared by a method of the present invention for the production of a ketopentose and/or a biofuel and/or a pentose derived compound.

BACKGROUND

Biofuels are being developed as a green and sustainable alternative to fossil fuels for transportation, heating and energy supply. Rising oil prices have made the production of biofuels more economically feasible, and ultimately the availability of fossil fuels is limited. Bioethanol, a biofuel, is generally considered as being much more $CO_2$ neutral in comparison with petroleum based transportation fuel. In addition, it is possible to use bioethanol as a partial as well as full gasoline substitute without drastic changes to the engine technology.

Typically, bioethanol is produced by fermentation of sugars derived from agricultural feedstock—such as sugar cane, sugar beet, maize and cereals (such as wheat and corn)—which are starch—rich and sugar-rich plant materials (the remainder of these plant materials is referred to as agricultural waste). However, a problem associated with processes which use these materials is that they utilise what could otherwise have been used for foodstuffs for humans and animal feeds. A consequence of this is that there is a reduction in the amount of foodstuffs and animal feeds which are available which, in turn, increases the price of food.

In fact, it has been predicted that even if the entire maize crop of the USA was used for ethanol production it would not be possible to meet the future demand in the USA. For example, in Spring 2008 the US Department for Agriculture estimated that, based on the amount of US land sown with maize, about 12 billion bushels of maize would be harvested in USA in 2008. Using techniques currently available in the art, 2.8 gallons of ethanol is the average production from 1 bushel of maize. Thus, if the entire 2008 USA maize harvest was made into ethanol, 33 billion gallons of ethanol would be obtained. According to the US Energy Information Administration statistics, however, 142 billion gallons of gasoline was used as fuel for cars and trucks in 2007 in USA. Assuming that there is no significant decline in the demand for gasoline in the USA in 2008, then the supply of the gasoline substitute ethanol from maize could not meet the demand.

Thus, the availability of sources of starch-rich and sugar-rich plant materials is a rate-limiting factor for the production of biofuels.

The so-called agricultural waste material of, for example, sugar cane, sugar beet, sorghum, Soya beans, maize, and cereals (such as wheat and corn) comprises mainly lignocellulosic material. Lignocellulosic material primarily comprises long sugar chains. In general, about two thirds of the sugars of these long chain sugars are hexose sugars (in particular glucose), which are mainly in the form of cellulose, and about one third of the sugars of these long chain sugars are pentose sugars (in particular xylose and arabinose) present mainly in the form of arabinoxylan polymers. After hydrolysis of cellulose, the hexose sugars can be fermented by the traditional yeast based method. However, cellulose is a robust structure which is very resistant to extraction and enzymatic hydrolysis. Arabinoxylans are comparatively easier to extract and hydrolyse to release, in the main, pentose sugars; but the released sugars can not be fermented into ethanol in sufficiently high concentration by known microorganisms.

Two obstacles for efficient ethanol production from waste plant material are the difficulties associated with depolymerisation of cellulose and the lack of suitable organisms that can metabolize, for large-scale production, pentose sugars into ethanol.

Theoretically, one way to obtain such a suitable organism is to transfer the ability to metabolize pentoses from natural pentose metabolizing organisms into known highly efficient ethanol producers. This has been the subject of much work in various research groups during the last 15-20 years. But with pentoses it has not been possible to obtain metabolic rates comparable to the rates obtained when using glucose. To increase this low metabolic rate has been and is still a subject of discussion and ongoing research and is still a major obstacle for the use of, for example, engineered *S. cerevisiae* in ethanol fermentation from pentoses.

STATEMENTS OF THE INVENTION

Surprisingly, we have found that by modifying microorganisms to express and/or overexpress an aldose-1-epimerase, a faster conversion of aldopentoses into ketopentoses is facilitated (when compared to the equivalent microorganisms prior to modification). In that way, microorganisms can be obtained which are capable of faster conversion of pentose sugars (preferably aldopentose sugars) into a biofuel (preferably a biofuel comprising ethanol) when compared to the equivalent microorganisms prior to modification, which is particularly advantageous for large-scale industrial biofuel production.

Figure 4:
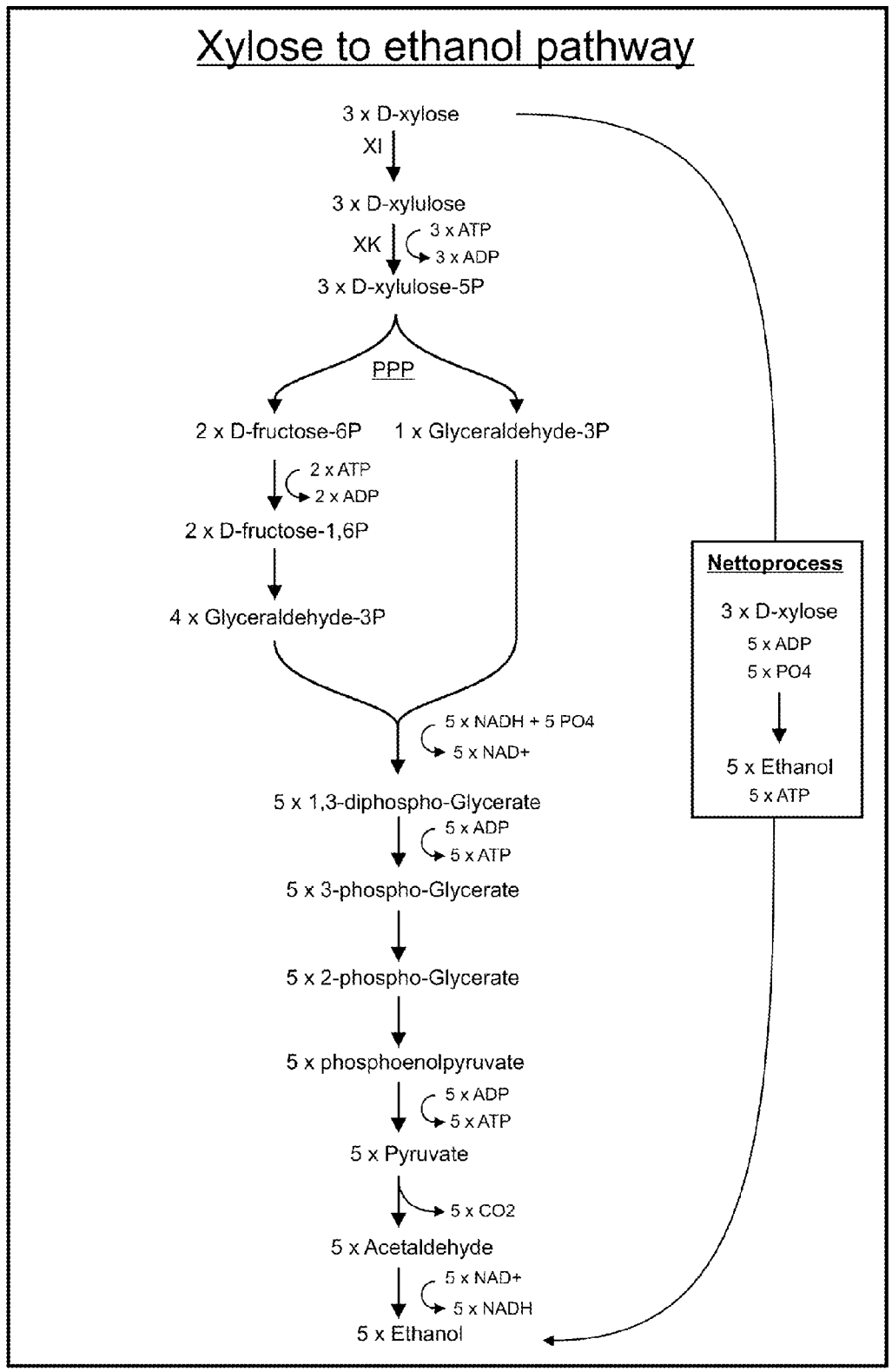

Xylulose-5-phosphate is an intermediate (which may be derived from D-xylose, L-arabinose or even D-lyxose), that enters into the pentose phosphate pathway and is further metabolized into ethanol under anaerobic conditions. An entire metabolic pathway from xylose into ethanol is shown in FIG. 4.

Ribulose-5-phosphate is an intermediate (which may be derived from D-ribose), that enters into the pentose phosphate pathway and is further metabolized into ethanol under anaerobic conditions.

In one aspect, the present invention provides a transformed microorganism capable of converting an aldopentose to a ketopentose at a higher rate than the equivalent microorganism prior to transformation.

In another aspect, the present invention provides a transformed microorganism capable of a higher growth rate in the presence of aldopentose than the equivalent microorganism prior to transformation.

The present invention additionally provides a transformed microorganism capable of a higher metabolism of aldopentose than the equivalent microorganism prior to transformation.

The present invention further provides a microorganism wherein said microorganism comprises a nucleotide sequence encoding an exogenous aldose-1-epimerase.

In another aspect, the present invention provides a microorganism wherein said microorganism is capable of expressing an exogenous aldose-1-epimerase.

In a further aspect, the present invention provides a microorganism wherein said microorganism comprises a nucleotide sequence encoding an exogenous aldose-1-epimerase, and wherein said microorganism is capable of expressing said exogenous aldose-1-epimerase; and wherein said microorganism is capable of converting an aldopentose to a ketopentose.

Further, the present invention provides a microorganism comprising an expression vector encoding an aldose-1-epimerase, wherein said microorganism is capable of converting an aldopentose to a ketopentose.

In another aspect, the present invention provides a transformed microorganism wherein said microorganism is capable of expressing an aldose-1-epimerase and wherein said microorganism is capable of converting an aldopentose to a ketopentose.

The present invention provides, in a further aspect, a method for preparing a transformed microorganism capable of producing a ketopentose, said method comprising the step of transforming a microorganism with a nucleotide sequence encoding an aldose-1-epimerase, and wherein said transformed microorganism is capable of converting an aldopentose to a ketopentose.

The present invention provides, in a further aspect, a method for preparing a transformed microorganism capable of producing a pentose derived compound, said method comprising the step of transforming a microorganism with a nucleotide sequence encoding an aldose-1-epimerase, and wherein said transformed microorganism is capable of converting an aldopentose to a ketopentose.

The present invention provides, in a further aspect, a method for preparing a transformed microorganism capable of producing a pentose derived compound at a higher rate than the equivalent microorganism prior to transformation, said method comprising the step of transforming a microorganism with a nucleotide sequence encoding an aldose-1-epimerase, and wherein said transformed microorganism is capable of converting an aldopentose to a ketopentose.

In another aspect, the present invention provides a method for preparing a transformed microorganism capable of converting an aldopentose to a ketopentose at a higher rate than the equivalent microorganism prior to transformation, said method comprising the step of transforming a microorganism with a nucleotide sequence encoding an aldose-1-epimerase, wherein said transformed microorganism is capable of converting an aldopentose to a ketopentose.

In a further aspect, the present invention provides a method for preparing a transformed microorganism capable of converting an aldopentose to a ketopentose at a higher rate than the equivalent microorganism prior to transformation, said method comprising the step of transforming a microorganism such that the expression of an aldose-1-epimerase is upregulated, wherein said transformed microorganism is capable of converting an aldopentose to a ketopentose.

In addition, the present invention provides a method for preparing a transformed microorganism capable of a higher growth rate in the presence of aldopentose than the equivalent microorganism prior to transformation, said method comprising the step of transforming a microorganism with a nucleotide sequence encoding an aldose-1-epimerase, wherein said transformed microorganism is capable of converting an aldopentose to a ketopentose.

In a further aspect, the present invention provides a method for preparing a transformed microorganism capable of a higher growth rate in the presence of aldopentose than the equivalent microorganism prior to transformation, said method comprising the step of transforming a microorganism such that the expression of an aldose-1-epimerase is upregulated, wherein said transformed microorganism is capable of converting an aldopentose to a ketopentose.

The present invention additionally provides a method for preparing a transformed microorganism capable of a higher metabolism of aldopentose than the equivalent microorganism prior to transformation, said method comprising the step of transforming a microorganism with a nucleotide sequence encoding an aldose-1-epimerase, wherein said transformed microorganism is capable of converting an aldopentose to a ketopentose.

In a further aspect, the present invention provides a method for preparing a transformed microorganism capable of a higher metabolism of aldopentose than the equivalent microorganism prior to transformation, said method comprising the step of transforming a microorganism such that the expression of an aldose-1-epimerase is upregulated, wherein said transformed microorganism is capable of converting an aldopentose to a ketopentose.

The present invention provides, in a further aspect, a method for producing a pentose derived compound, wherein said method comprises culturing in a culture medium a microorganism according to the present invention or a microorganism prepared by a method of the present invention.

In a further aspect, the present invention provides a method for producing a pentose derived compound comprising the steps of:
(a) transforming a microorganism with a nucleotide sequence encoding an aldose-1-epimerase wherein said transformed microorganism is capable of converting an aldopentose to a ketopentose; and (b) culturing the transformed microorganism in a culture medium.

The present invention provides, in a further aspect, a method for producing a ketopentose, wherein said method comprises culturing in a culture medium a microorganism according to the present invention or a microorganism prepared by a method of the present invention.

In a further aspect, the present invention provides a method for producing a ketopentose comprising the steps of
(a) transforming a microorganism with a nucleotide sequence encoding an aldose-1-epimerase wherein said transformed microorganism is capable of converting an aldopentose to a ketopentose; and
(b) culturing the transformed microorganism in a culture medium.

Ketopentoses mentioned herein may be metabolised further within the cell facilitating the production of a range of products, which include but are not limited to: ethanol, lactic acid, succinic acid, acetic acid, acetaldehyde, itaconic acid, cresol, 3-hydroxypropionic acid, poly-3-hydroxyalkanoates, protocatechuic acid, pyrocatechol, guaiacol, veratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione and aromatic amino acids.

In another aspect, the present invention provides a method for producing a biofuel, wherein said method comprises the step of culturing in a culture medium a microorganism according to the present invention or a microorganism prepared by a method according to the present invention.

In another aspect, the present invention provides a method for preparing a transformed microorganism capable of producing a biofuel at a higher rate in a culture medium than the equivalent microorganism prior to transformation, said method comprising the step of transforming a microorganism with a nucleotide sequence encoding an aldose-1-epimerase, preferably in an expression vector encoding same, wherein said transformed microorganism is capable of converting an aldopentose to a ketopentose.

In another aspect, the present invention provides a method for producing a biofuel comprising the steps of:
(a) transforming a microorganism with a nucleotide sequence encoding an aldose-1-epimerase, preferably in an expression vector encoding same, wherein said transformed microorganism is capable of converting an aldopentose to a ketopentose; and
(b) culturing the transformed microorganism in a culture medium comprising aldopentose.

In a further aspect, the present invention provides a method for producing a biofuel wherein said method comprises the step of culturing a microorganism in a culture medium, wherein said microorganism comprises a nucleotide sequence encoding an aldose-1-epimerase and wherein said microorganism is capable of expressing said aldose-1-epimerase; and wherein said microorganism is capable of converting an aldopentose to a ketopentose.

In a further aspect, the present invention provides a biofuel obtained or obtainable by a method according to the present invention.

In another aspect, the present invention provides the use of a microorganism according to the present invention or a microorganism prepared by a method of the present invention for the production of a ketopentose.

In another aspect, the present invention provides the use of a microorganism according to the present invention or a microorganism prepared by a method of the present invention for the production of a pentose derived compound.

Further, the present invention provides the use of a microorganism according to the present invention or a microorganism prepared by a method of the present invention for the production of a biofuel.

In another aspect, the present invention provides the use of a microorganism for the production of a biofuel, wherein said microorganism comprises a nucleotide sequence encoding an aldose-1-epimerase, and wherein said microorganism is capable of expressing said aldose-1-epimerase, and wherein said microorganism is capable of converting an aldopentose to a ketopentose.

In a further aspect, the present invention provides an inoculum comprising a microorganism according to the present invention or a microorganism prepared by a method according to the present invention.

Further, the present invention provides a culture medium comprising a microorganism according to the present invention or a microorganism prepared by a method according to the present invention.

SOME ADVANTAGES

Advantageously, by using the microorganisms according to the present invention, biofuels (such as ethanol) can be produced.

A further advantage is that by using the microorganisms according to the present invention, biofuels (such as ethanol) can be efficiently produced using pentose sugars. Without wishing to be bound by theory, the modification of microorganisms to express or overexpress an aldose-1-epimerase allows an increase in the rate of inter-conversion between aldopentose anomers and the intracellular conversion of aldopentoses to ketopentoses—in other words it relieves a rate-limiting constraint—which in turn allows for a faster and more efficient production of ethanol by the pentose phosphate pathway than compared to the equivalent microorganism prior to modification.

More advantageously, by using the microorganisms according to the present invention, biofuels can be produced from waste materials such as agricultural wastes (including cereal straw—such as wheat straw; sugar beet pulp; sugar cane bagasse; stovers—such as sorghum, Soya beans, maize or corn stovers; and wood chips). With the present invention there is no need (or there is a reduced need) to use materials (such as sugar cane extract, sugar beet extract, sorghum starch, maize starch, wheat starch or corn starch) which could otherwise be used as a food source for humans and/or as an animal feed.

Most advantageously, the present invention provides microorganisms which are capable of metabolising, for large-scale production (such as industrial production), pentose sugars (such as aldopentose sugars) into a biofuel (such as a biofuel comprising ethanol).

Advantageously, the microorganisms according to the present invention enable the optimum use of the sugars released by hydrolysis of lignocellulosic material by the fermentation of pentose sugars.

The present invention enables the production of a biofuel which is more $CO_2$ neutral in comparison with petroleum based transportation fuel. With the present invention, $CO_2$ emissions will be low (even lower) when producing the biofuel according to the present invention than compared to the production of a typical petroleum based transportation fuel (fossil fuels).

Surprisingly, the present invention shows that the transformation of microorganisms to express aldose-1-epimerase results in an increased conversion rate of pentose sugars to a biofuel.

FIGURES

FIG. 1. A schematic representation of the metabolic pathways detailing the metabolism of the two most abundant aldopentoses, D-xylose and L-arabinose. Both aldopentoses are converted into a ketopentose, and further into D-xylulose 5-phosphate. Without wishing to be bound by theory, as indicated on the figure, one type of pathway (aldose reductase type) is found in fungi whereas the other type of pathway (isomerase type) is found in bacteria. In the fungal pathway type, the first enzymes may be called "D-xylose reductase" and "L-arabinose reductase", but often the same enzyme can reduce both D-xylose and L-arabinose and may then serve both pathways and be referred to by the less specific name "aldose reductase".

Figure 2:
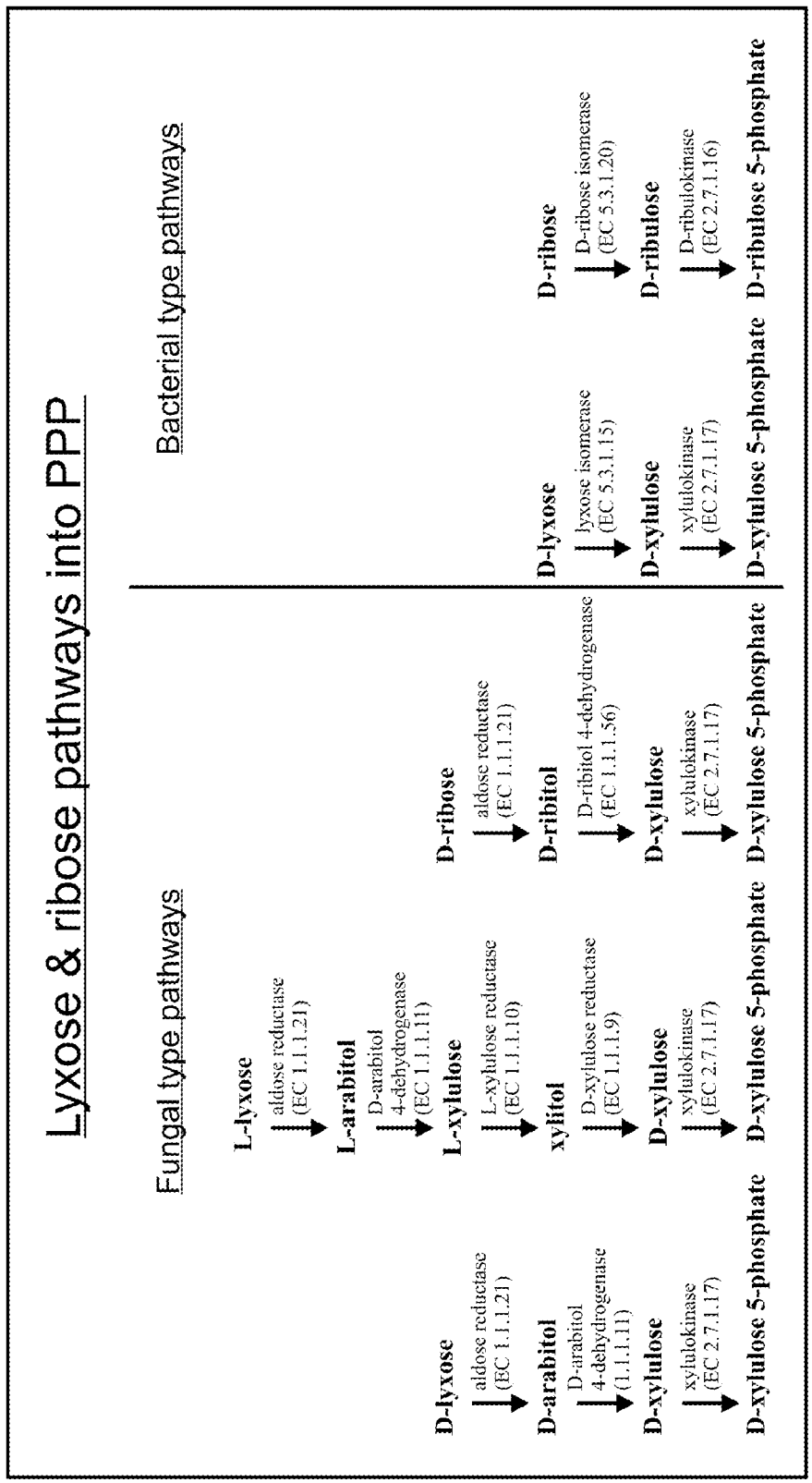

FIG. 2. Without wishing to be bound by theory, FIG. 2 shows a schematic representation of fungal and bacterial type of metabolic pathways of some less abundant pentoses (D- and L-lyxose, D-ribose) detailing the initial metabolism until the entry into the pentose phosphate pathway.

Figure 3:
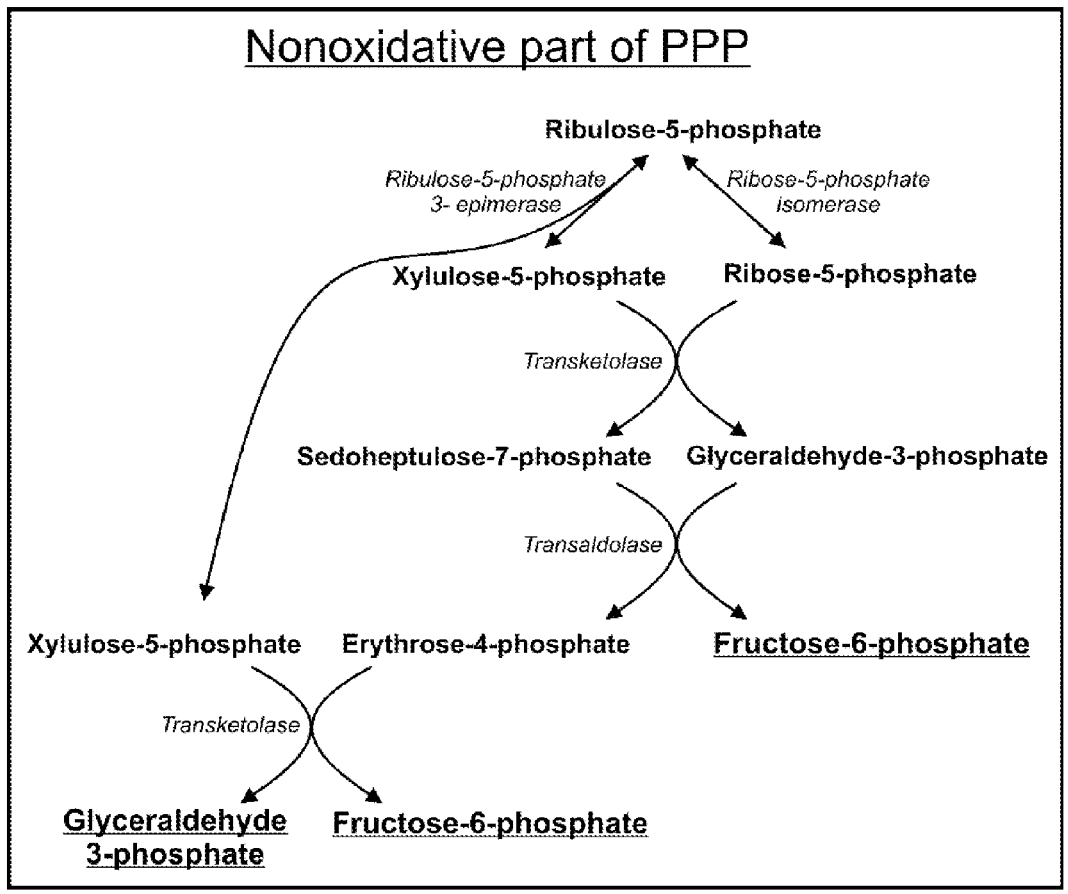

FIG. 3. A schematic representation of the non-oxidative part of the pentose phosphate pathway (PPP).

FIG. 4. A. schematic representation of the pentose phosphate pathway (PPP). Here, ketopentose xylulose-5-phosphate, which may be derived from D-xylose or L-arabinose, is further metabolized into ethanol under anaerobic conditions. XI is xylose isomerase and XK is xylulokinase. The net input of xylose into the process and the net output of ethanol from the process is shown (nettoprocess).

DETAILED DESCRIPTION

As used herein the phrase "a transformed microorganism capable of converting an aldopentose to a ketopentose at a higher rate than the equivalent microorganism prior to transformation" encompasses microorganisms transformed with a nucleotide sequence encoding an aldose-1-epimerase, such as an expression vector comprising said nucleotide sequence, and microorganisms transformed to upregulate the expression of an aldose-1-epimerase (in other words overexpress an aldose-1-epimerase).

In one embodiment the microorganism has been transformed with a nucleotide sequence that causes the microorganism to overexpress an aldose-1-epimerase. For example, a promoter is inserted into the genome of a microorganism which enables the microorganism to overexpress an endogenous nucleotide sequence encoding an aldose-1-epimerase.

In another embodiment the microorganism has been transformed with a nucleotide sequence encoding an aldose-1-epimerase. For example, the microorganism is transformed with an expression vector comprising a nucleotide sequence encoding an aldose-1-epimerase operably linked to a regulatory sequence.

Preferably the nucleotide sequence encoding an aldose-1-epimerase mentioned herein is in an expression vector encoding same.

Preferably the expression vector mentioned herein comprises a promoter capable of overexpressing the nucleotide sequence encoding an aldose-1-epimerase. Examples of such promoters include the GPD promoter, the TEF promoter and the ADP promoter. Preferred promoters which may be used to overexpress an aldose-1-epimerase can be any of the regulatory elements controlling the expression of nucleotide sequences encoding proteins involved in glycolysis and glucose fermentation.

As used herein, the term "higher rate" in the phrase "a transformed microorganism capable of converting an aldopentose to a ketopentose at a higher rate than the equivalent microorganism prior to transformation" refers to a transformed microorganism which is capable of decreasing the amount of aldopentose in a culture medium such that the reduction in the amount of aldopentose in the culture medium is at least 5%, 10%, 20% or 25% more per cell than that of the equivalent microorganism prior to transformation when cultured under the same culture conditions for a given time period within the exponential growth phase.

The term "exponential growth phase" is used in the normal sense of the art—e.g. the microorganisms are dividing at a constant rate such that the total number of microorganisms doubles with each division. The skilled person can readily determine the lag phase (the period during which the cells adjust to a new environment before the onset of exponential growth), the exponential growth phase, the stationary phase (where the rate of cell division equals the rate of cell death, hence viable cell number remains constant) and the death phase (where the viable count declines) for any microorganism for a given set of culture conditions.

The term "equivalent microorganism prior to transformation" as used herein refers to the microorganism prior to transformation with a nucleotide sequence that encodes an aldose-1-epimerase or prior to transformation with a nucleotide sequence that causes the upregulation (e.g. overexpression) of an aldose-1-epimerase.

As used herein the term "the conversion of an aldopentose to a ketopentose" refers to, for example, the conversion of the aldopentose xylose to the ketopentose xylulose; the conversion of the aldopentose arabinose to the ketopentose xylulose; the conversion of the aldopentose arabinose to the ketopentose ribulose; the conversion of the aldopentose lyxose to the ketopentose xylulose; and the conversion of the aldopentose ribose to the ketopentose ribulose.

In a preferred aspect, the ketopentose is xylulose.

The term "a transformed microorganism capable of converting an aldopentose to a ketopentose" as used herein refers to a microorganism which comprises one or more polynucleotide sequences encoding one or more polypeptides involved in the conversion of an aldopentose to a ketopentose. Examples of polypeptides capable of converting an aldopentose to a ketopentose include xylose isomerase, arabinose isomerase, D-lyxose isomerase, and ribose isomerase; the combination of xylose reductase and xylulose reductase, the combination of arabinose reductase, L-arabitol 4-dehydrogenase, L-xylulose reductase and D-xylulose reductase, and the combination of D-lyxose reductase and D-arabinitol dehydrogenase. The polypeptide(s) may be endogenous and/or exogenous to said microorganism. The polypeptide(s) may be encoded by one or more expression vectors.

Preferably the aldopentose is selected from the group consisting of xylose, arabinose, ribose and lyxose. Preferably the aldopentose is xylose or arabinose. More preferably, the aldopentose is xylose.

The spontaneous conversion between α-aldopentose and β-aldopentose in microorganisms is slow. For example, the spontaneous conversion of β-D-xylose to α-D-xylose has a first-order K-value of about 0.094/min at physiologic temperature (Bailey et al, 1969).

As used herein, the term "overexpress" in the phrase "a nucleotide sequence that causes the microorganism to overexpress an aldose-1-epimerase" and "a promoter capable of overexpressing the nucleotide sequence encoding an aldose-1-epimerases" refers to an increase in expression from zero to a level of expression or going from a lower level of expression to a higher level of expression (e.g. upregulation) when the transformed microorganism is compared to the equivalent microorganism prior to transformation. Microorganisms overexpressing an aldose-1-epimerase have an increased ability to catalyse the conversion between α-aldopentose and β-aldopentose.

Preferably said transformed microorganism which overexpresses an aldose-1-epimerase is able to catalyse the conversion of an α-aldopentose to a β-aldopentose at a rate which is at least 10%, 15%, 20% or 25% higher than an untransformed microorganism, measured in an assay where 1 g of disrupted cell mass has been added to 50 ml of a freshly prepared, buffered, neutral solution containing 100 mM of the β-aldopentose, using the interconversion assay as described later herein.

Examples of microorganisms overexpressing an aldose-1-epimerase include: (i) microorganisms transformed with an expression vector encoding an aldose-1-epimerase (prior to transformation said microorganism was not capable of expressing the aldose-1-epimerase); and (ii) microorganisms transformed to upregulate the expression of an endogenous aldose-1-epimerase (prior to transformation said microorganism was capable of expressing said aldose-1-epimerase for a given set of culture conditions during exponential growth but after transformation said microorganism is capable of expressing said aldose-1-epimerase at a higher level, in the same culture conditions, during exponential growth).

As used herein the term "higher growth rate" in the phrase "a transformed microorganism capable of a higher growth rate in the presence of aldopentose than the equivalent microorganism prior to transformation" refers to a transformed microorganism which is capable of an increased growth rate such that the time taken for a doubling in the number of microorganisms per ml during the exponential growth phase is at least 10%, 15%, 20% or 25% lower than that of the equivalent microorganism prior to transformation when cultured under the same culture conditions. In a preferred aspect, the microorganisms are cultured at their optimal growth temperature; and preferably the culture medium comprises between 1% and 4% aldopentose in addition to optimal amounts of salts, vitamins and other nutrients necessary for the microorganism.

The term "higher metabolism" as used herein in the phrase "a transformed microorganism capable of a higher metabolism of aldopentose than the equivalent microorganism prior to transformation" refers to a transformed microorganism which is capable of a metabolising aldopentose such that the consumed amount of the aldopentose in the culture medium is at least 10%, 20%, 25%, 30% or 35% higher per cell than that of the equivalent microorganism prior to transformation when cultured under the same culture conditions for a given time period within the exponential growth phase. In a preferred aspect, the microorganisms are cultured at their optimal growth temperature; and preferably the culture medium comprises between 1% and 4% aldopentose in addition to optimal amounts of salts, vitamins and other nutrients necessary for the microorganism.

Preferably the transformed microorganism according to the present invention has a rate of conversion of the aldopentose to the ketopentose which is at a higher level than the equivalent microorganism prior to transformation. The term "higher level" as used in this phrase refers to a transformed microorganism which is capable of a converting aldopentose such that the reduction in the amount of aldopentose in the culture medium is at least 5%, 10%, 20% or 25% more per cell than that of the equivalent microorganism prior to transformation when cultured under the same culture conditions for a given time period within the exponential growth phase.

The term "a nucleotide sequence encoding an aldose-1-epimerase" as used herein encompasses nucleotide sequences comprising regulatory sequences enabling the expression of the nucleotide sequence encoding an aldose-1-epimerase such as promoters and enhancers which may be natively or non-natively associated with the nucleotide sequence encoding an aldose-1-epimerase.

As used herein, the term "higher rate" in the phrase "a transformed microorganism capable of producing a biofuel at a higher rate in a culture medium than the equivalent microorganism prior to transformation" refers to a transformed microorganism capable of producing at least 10%, 20%, 25%, 30% or 35% more biofuel per cell than that of the equivalent microorganism prior to transformation when cultured under the same culture conditions for a given time period within the exponential growth phase. Preferably, the microorganisms are cultured at their optimal production circumstances (e.g. optimal oxygen pressure and stirring speed), and preferably the culture medium comprises between 2% and 6% aldopentose in addition to optimal amounts of salts, vitamins and other nutrients necessary for the microorganism.

Preferably, the method for producing a biofuel further comprises the step of obtaining the biofuel from the culture medium.

Transformed Microorganism

As mentioned herein, the term "transformed microorganism" refers to a microorganism that has been genetically altered by recombinant DNA technology. The term "transformed" as used herein is synonymous with terms such as "transfected", "recombinant", "genetically engineered" and "genetically modified".

The term "transformed microorganism" in relation to the present invention includes any microorganism that comprises an expression vector(s) comprising the nucleotide sequence(s) mentioned herein and/or a promoter(s) that is capable of allowing the expression (in particular overexpression i.e. upregulation) of the nucleotide sequence(s) mentioned herein. In one embodiment the nucleotide sequence(s) is incorporated in the genome of the microorganism. In another embodiment, the promoter is incorporated in the genome of the microorganism. These features enable the transformed microorganism (when compared to equivalent microorganism prior to transformation) to (i) metabolise aldopentose sugars at a higher rate; and/or (ii) have a higher growth rate; and/or (iii) produce ketopentose at a higher rate; and/or (iv) produce a pentose derived compound at a higher rate; and/or (v) produce a biofuel at a higher rate.

The term "transformed microorganism" does not cover native nucleotide coding sequences in their natural environment when they are under the control of their native promoter which is also in its natural environment.

Therefore, the transformed microorganism of the present invention includes a microorganism comprising any one of or combinations of, the nucleotide sequences coding for the enzymes mentioned herein, constructs comprising said nucleotide sequences, vectors comprising said nucleotide sequences, plasmids comprising said nucleotide sequences and expression vectors comprising said nucleotide sequences.

Thus, a further embodiment of the present invention provides microorganisms transformed or transfected with a nucleotide sequence(s) that expresses the enzyme(s) mentioned herein. The microorganism will be chosen to be compatible with the vector and may be, for example, bacterial, fungal or yeast cells.

Examples of suitable bacterial host organisms are gram positive or gram negative bacterial species.

Depending on the nature of the nucleotide sequence(s) encoding the enzyme(s) mentioned herein, eukaryotic hosts such as yeasts or other fungi may be preferred. In general, yeast cells are preferred over fungal cells because they are easier to manipulate.

The use of suitable microorganisms—such as yeast and fungal host cells—may provide for post-translational modifications (e.g. myristoylation, glycosylation, truncation, lapidation and tyrosine, serine or threonine phosphorylation) as may be needed to confer optimal biological activity on recombinant expression products mentioned herein.

Suitable microorganisms include bacteria, fungi and yeasts. Preferably the microorganism is a yeast or a bacterium.

Preferably said transformed microorganism is a transformed yeast. Preferably said transformed yeast is derived from the genus *Saccharomyces*. More preferably said transformed yeast is *Saccharomyces cerevisiae*.

In another embodiment, preferably said transformed microorganism is a transformed bacterium. Preferably said transformed bacterium is derived from the genus *Zymomonas* or the genus *Zymobacter*. More preferably said transformed bacterium is *Zymomonas mobilis* or *Zymobacter palmae*.

In one embodiment, the transformed microorganism described herein metabolises aldopentose sugars at a higher rate when cultured in a culture medium comprising aldopentose than the equivalent microorganism prior to transformation.

In another aspect, the growth rate of the transformed microorganism described herein is higher when cultured in a culture medium comprising aldopentose than the equivalent microorganism prior to transformation.

In a further aspect, the transformed microorganism mentioned herein is capable of producing the ketopentose at a higher rate when cultured in a culture medium comprising aldopentose than the equivalent microorganism prior to transformation.

In another aspect, the transformed microorganism mentioned herein is capable of producing a biofuel at a higher rate when cultured in a culture medium comprising aldopentose than the equivalent microorganism prior to transformation.

Microorganism may be transformed using techniques which are routine in the art such as electroporation (Sambrook et al 1989). Further, the presence of a sequence in a transformed microorganism may be determined by growth selection on suitable media which select for the growth of the transformed microorganism. Alternatively or in addition, the presence of inserted, heterologous DNA sequences may be determined by direct colony PCR using primers specifically designed for the inserted sequence. Such techniques are well known and routine in the art (see, for example, Sambrook et al 1989 and Ausubel et al 1995).

A transformed microorganisms according to the present invention may be used in combination with one or more transformed microorganisms according to the present invention.

For example, one or more transformed microorganisms according to the present invention capable of converting D-xylose to D-xylulose may be used in combination with one or more microorganisms selected from the group consisting of: a transformed microorganism according to the present invention capable of converting L-arabinase to D-xylulose; a transformed microorganism according to the present invention capable of converting L-arabinase to L-ribulose; a transformed microorganism according to the present invention capable of converting D-lyxose to D-xylulose; and a transformed microorganism according to the present invention capable of converting D-ribose to D-ribulose.

In another example, one or more transformed microorganism according to the present invention capable of converting L-arabinase to D-xylulose may be used in combination with one or more microorganisms selected from the group consisting of: a transformed microorganism according to the present invention capable of converting D-xylose to D-xylulose; a transformed microorganism according to the present invention capable of converting L-arabinase to L-ribulose; a transformed microorganism according to the present invention capable of converting D-lyxose to D-xylulose; and a transformed microorganism according to the present invention capable of converting D-ribose to D-ribulose.

In another example, one or more transformed microorganism according to the present invention capable of converting L-arabinase to L-ribulose may be used in combination with one or more microorganisms selected from the group consisting of: a transformed microorganism according to the present invention capable of converting D-xylose to D-xylulose; a transformed microorganism according to the present invention capable of converting L-arabinase to D-xylulose; a transformed microorganism according to the present invention capable of converting D-lyxose to D-xylulose; and a transformed microorganism according to the present invention capable of converting D-ribose to D-ribulose.

In a further example, one or more transformed microorganism according to the present invention capable of converting D-lyxose to D-xylulose may be used in combination with one or more microorganisms selected from the group consisting of a transformed microorganism according to the present invention capable of converting L-arabinase to D-xylulose; a transformed microorganism according to the present invention capable of converting L-arabinase to L-ribulose; a transformed microorganism according to the present invention capable of converting D-xylose to D-xylulose; and a transformed microorganism according to the present invention capable of converting D-ribose to D-ribulose.

In another further example, one or more transformed microorganism according to the present invention capable of converting D-ribose to D-ribulose may be used in combination with one or more microorganisms selected from the group consisting of: a transformed microorganism according to the present invention capable of converting L-arabinase to D-xylulose; a transformed microorganism according to the present invention capable of converting L-arabinase to L-ribulose; a transformed microorganism according to the present invention capable of converting D-lyxose to D-xylulose; and a transformed microorganism according to the present invention capable of converting D-xylose to D-xylulose.

The transformed microorganisms according to the present invention may be used in combination with one or more further microorganisms. For example, one or more transformed microorganisms according to the present invention may cultured in combination with at least one microorganism capable of producing, under certain culture conditions, one of more components selected from the list consisting of ethanol, lactic acid, succinic acid, acetic acid, acetaldehyde, itaconic acid, cresol, 3-hydroxypropionic acid, poly-3-hydroxyalkanoates, protocatechuic acid, pyrocatechol, guaiacol, veratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione and aromatic amino acids.

In a further aspect, there is provided a combination of (i) one or more transformed microorganisms according to the present invention and (ii) at least one further microorganism capable of producing, under certain culture conditions, one of more components selected from the list consisting of: ethanol, lactic acid, succinic acid, acetic acid, acetaldehyde, itaconic acid, cresol, 3-hydroxypropionic acid, poly-3-hydroxyalkanoates, protocatechuic acid, pyrocatechol, guaiacol, veratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione and aromatic amino acids.

Additionally, the present invention provides an inoculum comprising one of the above-mentioned combinations.

Further, there is provided a culture medium comprising one of the above-mentioned combinations.

In addition, the present invention provides a kit comprising (i) an inoculum comprising one or more microorganisms according to the present invention and (ii) an inoculum comprising one or more further microorganisms mentioned herein.

Expression Vector

The term "expression vector" means a construct capable of in vivo or in vitro expression.

In one aspect, the expression vector is incorporated into the genome of a suitable microorganism. The term "incorporated" preferably covers stable incorporation into the genome.

The nucleotide sequences mentioned herein may be present in a vector in which the nucleotide sequence is operably linked to regulatory sequences capable of providing for the expression of the nucleotide sequence by a suitable host microorganism.

The vectors are transformed into a suitable host microorganisms as described herein.

The choice of vector e.g. a plasmid, cosmid, or phage vector will often depend on the microorganism into which it is to be introduced.

The vectors for use herein may contain one or more selectable marker nucleotide sequences—such as a nucleotide sequence which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example to transfect, transform, transduce or infect a host microorganism.

The vector may further comprise a nucleotide sequence enabling the vector to replicate in the host microorganism in question. Examples of such sequences are the origins of replication of plasmids pUC19, pACYC177, pUB110, pE194, pAMB1 and pIJ702.

In a preferred aspect, the microorganism capable of converting an aldopentose to a ketopentose as mentioned herein comprises a nucleotide sequence encoding an aldose-1-epimerase.

Preferably an expression vector as mentioned herein comprises the nucleotide sequence encoding an aldose-1-epimerase.

Preferably the microorganism capable of converting an aldopentose to a ketopentose as mentioned herein comprises at least one expression vector encoding xylose reductase and/or D-xylulose reductase.

In another preferred aspect, the microorganism capable of converting an aldopentose to a ketopentose as mentioned herein comprises an expression vector encoding xylose reductase and an expression vector encoding D-xylulose reductase.

In a further aspect, preferably the microorganism capable of converting an aldopentose to a ketopentose as mentioned herein comprises at least one expression vector encoding xylose isomerase.

In another aspect, preferably the microorganism capable of converting an aldopentose to a ketopentose as mentioned herein comprises at least one expression vector encoding arabinose reductase and/or L-arabitol 4-dehydrogenase and/or L-xylulose reductase and/or D-xylulose reductase.

In a further preferred aspect, the microorganism capable of converting an aldopentose to a ketopentose as mentioned herein comprises an expression vector encoding arabinose reductase, an expression vector encoding L-arabitol 4-dehydrogenase, an expression vector encoding L-xylulose reductase, and an expression vector encoding D-xylulose reductase.

In a further preferred aspect, the microorganism capable of converting an aldopentose to a ketopentose as mentioned herein comprises an expression vector encoding L-arabinose isomerase.

Preferably, in another aspect, the microorganism capable of converting an aldopentose to a ketopentose as mentioned herein comprises at least one expression vector encoding L-arabinose isomerase and/or ribulokinase and/or ribulose phosphate 4-epimerase.

In a further preferred aspect, the microorganism capable of converting an aldopentose to a ketopentose as mentioned herein comprises an expression vector encoding L-arabinose isomerase, an expression vector encoding ribulokinase, and an expression vector encoding ribulose phosphate 4-epimerase.

In another preferred aspect the microorganism capable of converting an aldopentose to a ketopentose as mentioned herein comprises at least one expression vector encoding D-lyxose isomerase.

In a further preferred aspect the microorganism capable of converting an aldopentose to a ketopentose as mentioned herein comprises an expression vector encoding D-ribose isomerase.

Preferably, in another aspect, the microorganism capable of converting an aldopentose to a ketopentose as mentioned herein may further comprise at least one expression vector encoding one or more enzymes selected from the group consisting of xylulokinase, D-ribulokinase, ribose-5-phosphate isomerase, ribulose-5-phosphate epimerase, transaldolase, transketolase and any other enzyme of the pentose phosphate pathway. Preferably said microorganism capable of converting an aldopentose to a ketopentose as mentioned herein further comprises at least one expression vector encoding xylulokinase and/or D-ribulokinase. More preferably, said microorganism capable of converting an aldopentose to a ketopentose as mentioned herein further comprises at least one expression vector encoding xylulokinase. In another embodiment, preferably the microorganism capable of converting an aldopentose to a ketopentose as mentioned herein further comprises at least one expression vector encoding ribulose-5-phosphate epimerase and/or ribose-5-phosphate isomerase and/or transaldolase and/or transketolase.

In one aspect, an expression vector as mentioned herein, may further encode one or more enzymes selected from the group consisting of an aldose-1-epimerase, xylose reductase, D-xylulose reductase, xylose isomerase, arabinose reductase, L-arabitol 4-dehydrogenase, L-xylulose reductase, L-arabinose isomerase, ribulokinase, ribulose phosphate 4-epimerase, D-lyxose isomerase, D-ribose isomerase, xylulokinase, D-ribulokinase, ribulose-5-phosphate epimerase, ribose-5-phosphate isomerase, transaldolase, and transketolase.

In one aspect, an expression vector as mentioned herein, may further encode one or more enzymes selected from the group consisting of xylulokinase, D-ribulokinase, ribose-5-phosphate isomerase, D-ribulose-5-phosphate epimerase, transaldolase, transketolase and any other enzyme of the pentose phosphate pathway. In a preferred aspect an expression vector as described herein further encodes xylulokinase and/or D-ribulokinase. More preferably, said expression vector as mentioned herein further encodes xylulokinase. In another embodiment, preferably expression vector as mentioned herein further encodes ribulose-5-phosphate epimerase and/or ribose-5-phosphate isomerase and/or transaldolase and/or transketolase. In another more preferred embodiment, preferably expression vector as mentioned herein further encodes ribose-5-phosphate isomerase and/or transaldolase and/or transketolase.

In a preferred aspect, the microorganism capable of converting an aldopentose to a ketopentose as mentioned herein further comprises at least one expression vector encoding an aldose-1-epimerase.

Preferably an expression vector as mentioned herein further comprises a nucleotide sequence encoding an aldose-1-epimerase.

Regulatory Sequences

In some applications, the nucleotide sequence(s) mentioned herein is operably linked to a regulatory sequence which is capable of providing for the expression of the nucleotide sequence, such as by the chosen microorganism. By way of example, the present invention covers the use of a vector comprising the nucleotide sequence(s) mentioned herein operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence(s) encoding the enzyme(s) mentioned herein may also be achieved by the selection of heterologous regulatory regions, e.g. promoter, secretion leader and terminator regions.

Preferably, the nucleotide sequence(s) mentioned herein is operably linked to at least a promoter.

Other promoters may even be used to direct expression of the polypeptide(s) mentioned herein.

Examples of suitable promoters for directing the transcription of the nucleotide sequence in a bacterial, fungal or yeast cell are well known in the art.

The promoter can additionally include features to ensure or to increase expression in a suitable host. For example, the features can be conserved regions such as a Pribnow Box or a TATA box.

Constructs

The term "construct"—which is synonymous with terms such as "conjugate", "cassette" and "hybrid"—includes a nucleotide sequence mentioned herein directly or indirectly attached to a promoter.

An example of an indirect attachment is the provision of a suitable spacer group such as an intron sequence, such as the Sh1-intron or the ADH intron, intermediate the promoter and the nucleotide sequence(s) mentioned herein. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct comprises at least the nucleotide sequence(s) mentioned herein operably linked to a promoter.

Promoters

As mentioned herein, in one aspect the present invention relates to a microorganism that has been transformed with a nucleotide sequence, such as a promoter, that causes the microorganism to overexpress an aldose-1-epimerase.

For instance, the promoter is inserted into the genome of a microorganism which enables the microorganism to overexpress (e.g. upregulate) an endogenous nucleotide sequence encoding an aldose-1-epimerase.

In another aspect, the promoter is operably linked to a nucleotide sequence in, for example, an expression vector.

In another aspect, the promoter is not repressed by the presence of glucose.

Examples of suitable promoters that could be used in microorganisms according to the present invention, such as *Saccharomyces cerevisiae*, include: the promoter of the glyceraldehyde-3-phosphate dehydrogenase (GPD) gene; the promoter of the alcohol dehydrogenase (ADH) gene; the promoter of the Thyrotrophic embryonic factor (TEF) gene. Examples of suitable promoters that could be used in *Zymomonas mobilis* and in *Zymobacter palmae* include the *Zymomonas* Glyceraldehyde-3-phosphate dehydrogenase promoter (Conway et al, 1987) and the *Zymomonas enolase* promoter (Burnett et al, 1992).

Preferred promoters which may be used to overexpress an aldose-1-epimerase can be any of the regulatory elements controlling the expression of nucleotide sequences encoding proteins involved in glycolysis and glucose fermentation. Examples include, but not are limited to:

the P-pgi promoter capable of expressing the PGI1 gene said promoter comprises the nucleotide sequence between this gene and the open reading frame YBR197C;

the P-tpi promoter capable of expressing the TIM gene said promoter comprises the nucleotide sequence between this gene and the open reading frame YDR051C;

the P-hxk promoter capable of expressing the HXK2 gene said promoter comprises the nucleotide sequence between this gene and the gene FZF1;

the P-pfk promoter capable of expressing the PFK1 gene said promoter comprises the nucleotide sequence between this gene and the gene YAP1802;

the P-eno promoter capable of expressing the ENO2 gene said promoter comprises the nucleotide sequence between this gene and the gene SPC97;

the P-tdh promoter capable of expressing the TDH3 gene said promoter comprises the nucleotide sequence between this gene and the gene PDX1;

the P-fba promoter capable of expressing the FBA1 gene said promoter comprises the nucleotide sequence between this gene and the gene MPE1;

the P-gpm promoter capable of expressing the GPM1 gene said promoter comprises the nucleotide sequence between this gene and the open reading frame YKL151C;

the P-pdc promoter capable of expressing the PDC1 gene said promoter comprises the nucleotide sequence between this gene and the gene STU2; and, the P-pgm promoter capable of expressing the PGM2 gene said promoter comprises the nucleotide sequence between this gene and the gene YKU80.

Biofuel

As used herein, the term "biofuel" refers to a fuel (e.g. a liquid fuel) suitable for use in (for example) combustion engines. Said biofuel is derived from biological matter comprising pentose sugars and/or from which pentose sugars can be derived by hydrolysis by enzymatic means and/or by acidic treatment. Preferably said pentose sugar is an aldopentose.

Plant materials—including plant waste comprising lignocellulosic material (for instance: cereal straw, such as wheat straw; sugar beet pulp; sugar cane bagasse; sorghum stover; Soya bean stover; maize stover; corn stover; wood-chips; and paper-pulp) and whole plants (such as those which are grown for energy purposes e.g. switchgrass)—are suitable sources for pentose sugars, in particular aldopentose sugars, for the present invention. Other suitable sources of plant material include non-waste products (in other words, food and feed sources) such as sugar cane extract, sugar beet extract, sorghum, Soya beans, wheat starch and corn starch.

Preferably the biofuel mentioned herein comprises at least one alcohol.

In a preferred aspect, the alcohol is selected from the group consisting of methanol, ethanol, propanol and butanol. More preferably the biofuel comprises ethanol.

Preferably, said biofuel is obtained (or obtainable)—in other words, extracted (or extractable)—from the culture medium in which a transformed microorganism according to the present invention has been cultured under suitable conditions. Said biofuel may be obtained (or obtainable) from the culture medium using techniques which are routine in the art such as the removal of microorganism by centrifugation, isolation of the supernatant followed by distillation, and a further dehydration step to yield 99.5% pure ethanol.

The biofuel may comprise one or more further biofuel components such as butanol.

The one or more further biofuel components may be admixed with the biofuel before and/or after the biofuel is obtained or extracted (obtainable or extractable) from a culture.

Alternatively or in addition, one or more further biofuel components may be produced by culturing a microorganism in a culture medium before and/or after and/or at the same time as a transformed microorganism according to the present invention is/has been cultured in a culture medium in order to produce the biofuel.

The present invention further provides a transportation fuel which comprises a biofuel produced using the microorganisms according to the present invention.

Ethanol used as a transportation fuel may serve two different purposes:

(i) it can act as an oxygenated additive that raises the octane value and reduces emission in ReFormulated Gasoline (RFG) (tetraethyl lead or MTBE replacement);

(ii) it can act as a partial or full substitute for Regular Gasoline (RG) to reduce dependency on gasoline supply.

Anhydrous ethanol has an octane value of 130, and can be added in concentrations of 5-10% (depending on the season) to Regular Gasoline obtained directly from refineries. Traditionally, tetra-ethyl lead has been used for octane boosting however, due to health issues, the use of lead has been banned almost worldwide. The addition of oxygenates to Regular Gasoline lowers the carbon monoxide emissions as well as other particles contributing to air pollution. Methyl tert-butyl ether (MTBE) was initially used as a oxygenate additive, however the occurrence of MTBE contamination in drinking water aquifers has prompted some states to ban the use of this oxygenate. Ethanol is increasingly used worldwide as a replacement for MTBE as an oxygenate additive for the manufacturing of RFG.

Apart from serving as an oxygenate additive in the production of ReFormulated Gasoline, ethanol can be used as a general substitute for regular gasoline. Cars can use E10 blends (10% added ethanol) without any modification of the engine.

Further, vehicles have been manufactured which can run on 100% ethanol—in other words, there is no requirement for a fossil based fuel.

The transformed microorganisms according to the present invention or the microorganisms prepared by a method according to the present invention are capable of producing a biofuel at a higher rate than the equivalent microorganism prior to transformation. As used here, the term "higher rate" refers to a transformed microorganism which is capable of producing in the culture medium at least 5%, 10%, 20%, 25%, 30% or 35% more biofuel (such as bioethanol) per cell than that of the equivalent microorganism prior to transformation when cultured under the same culture conditions for a given time period within the exponential growth phase.

Pentose Derived Compound

As used herein, the term "pentose derived compound" refers to any compound derived from a pentose sugar. The pentose derived compound may be derived from an aldopentose. The pentose derived compound may be derived from a ketopentose.

Examples of pentose derived compounds include, but are not limited to: ethanol, aromatic amino acids, cresol, itaconic acid, lactic acid, succinic acid, acetic acid, acetaldehyde, poly-3-hydroxyalkanotes, and 3-hydroxypropionic acid. FIG. 1 shows other pentose derived compounds such as ketopentoses derived from aldopentoses. A pentose derived product may be converted to another product. For example, the ketopentose D-xylulose, derived from the aldopentose D-xylose, may be converted via the pentose phosphate pathway into ethanol.

Preferably said pentose derived compound is ethanol, lactic acid, succinic acid, acetic acid, acetaldehyde, itaconic acid, cresol, 3-hydroxypropionic acid, poly-3-hydroxyalkanoates, protocatechuic acid, pyrocatechol, guaiacol, veratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione and aromatic amino acids.

Preferably said pentose derived compound is ethanol, cresol, itaconic acid, lactic acid, succinic acid, and 3-hydroxypropionic acid.

More preferably said pentose derived compound is ethanol.

Culture Medium

The culture medium comprises at least one pentose. In a preferred aspect the culture medium comprises at least one aldopentose.

Preferably the transformed microorganisms are grown in the optimal culture medium for said microorganism. Using routine techniques, the optimal culture medium can be determined; in addition, the optimal growth conditions can be determined.

In one aspect said culture medium comprises about 1%, about 2%, about 4%, about 8%, about 15% or about 25% aldopentose before inoculation with the microorganism (i.e. at time zero).

Preferably said culture medium comprises the optimal amounts of salts, vitamins and other nutrients necessary for the microorganism.

The microorganisms are preferably cultured at their optimal growth temperature. The skilled person would have readily been able to determine the optimal temperature at which to culture microorganisms mentioned herein.

In one embodiment the microorganisms are cultured at about 20° C., 25° C., 30° C., 35° C., or 37° C.

In one embodiment the microorganisms are cultured at about 35° C. to 39° C., preferably about 36° C. to 38° C., more preferably at about 35.5° C. to 37.5° C.

Preferably the microorganisms are cultured for about 3 hours, about 6 hours, about 15 hours, about 24 hours, about 48 hours or about 96 hours.

In one aspect, the microorganism, in particular the transformed microorganism, is alcohol tolerant and/or acid tolerant.

The term "alcohol tolerant" in relation to the present invention refers to microorganisms which are capable of growth in a culture medium which comprises at least 2%, 5%, 10% or 15% alcohol.

As mentioned herein, the term "acid tolerant" refers to microorganisms which are capable of growth in a culture medium which has a pH equal to or less than 6.5, 6.0, 5.0, 4.0 or 3.0.

In a preferred aspect, the culture medium is inoculated with at least $5 \times 10^7$ to $5 \times 10^{11}$ cells per kg of culture medium, preferably $5 \times 10^8$ to $5 \times 10^{10}$ cells per kg of culture medium, preferably $1 \times 10^9$ to $1 \times 10^{10}$ cells per kg of culture medium and more preferably about $5 \times 10^9$ cells per kg of culture medium.

The terms "inoculum" and "starter culture" are interchangeable.

Sources of Pentose Sugars

Pentose sugars (in particular aldopentose sugars) are derived or derivable from plants.

Pentose sugars (in particular aldopentose sugars) may be derived from: plant materials typically used as food or feed sources (such as: sugar cane, sugar beet, sorghum, wheat and corn—which are starch-rich and sugar-rich plant materials); whole plants (such as those which are grown for energy purposes e.g. switchgrass); and, in particular, waste agricultural (plant) materials (such as: cereal straw, for instance, wheat straw; sugar beet pulp; bagasse, for instance, sugar cane bagasse; stovers, for instance, sorghum, Soya bean, maize or corn stovers; and wood chips).

Sources of pentose sugars for the culture medium described herein include lignocellulosic materials normally regarded as agricultural waste material. Stems, stalks and leaves contain lignocellulosic material. Sugar cane bagasses, corn stovers and wood chips (hemicellulose only) are three easily accessible sources of lignocellulosic material as these are already collected or stocked in large amounts for various reasons.

Lignocellulosic material consists primarily of long sugar chains. On average, two thirds of these sugars are hexose sugars, which are mainly present in cellulose, and one third of the sugars are pentose sugars present mainly in arabinoxylan polymers.

A significant amount of hemicellulose derived pentose sugar is xylose.

Lignocellulosic materials can be hydrolysed in order to release the hexose and/or pentose sugars in the long-chain sugars of the cellulose, hemicellulose and lignin.

Hydrolysis of lignocellulosic materials can be carried out by acidic treatment at elevated temperature. However, this treatment may generate sugar derived by-products that are toxic to the majority of microorganisms and prevent the conversion of the sugars to ethanol. Such toxic by-products (if generated) can be removed but this is generally uneconomical.

Alternatively, lignocellulosic materials can be hydrolysed using cellulose and hemicellulose hydrolyzing enzymes. Advantageously, this process avoids the generation of toxic side-products.

In a preferred aspect, the culture medium comprises material derived from one or more lignocellulosic materials which have been treated (examples of such treatment techniques include: steam treatment, steam explosion, wet oxidation, acid hydrolysis, alkaline wet oxidation and ammonia fibre expansion) to release hexose and/or pentose sugars. Preferably the lignocellulosic material is treated by an enzymatic hydrolysis process. Said hydrolysed lignocellulosic material may be further treated in order to extract the sugars before the use of said extract in a culture medium.

Hydrolysis of Lignocellulosic Material

Initial Mechanical Treatment:

The lignocellulosic material is chopped into smaller pieces as and when deemed necessary. For example, wheat straw is cut into pieces of approximately 5 cm in length.

Subsequent Hydrothermal Pretreatment:

The hydrothermal pretreatment of the lignocellulosic material may be carried out as a steam pretreatment followed by a washing step, thereby producing a fibre fraction and a liquid fraction. The fibre fraction contains more than 90% of the cellulose, the lignin originally present in the cellulosic material, and some of the hemicelluloses. The liquid fraction contains sugars from the hemicelluloses (C5 sugars), more than 90% of alkali chlorides comprised in the lignocellulosic biomass, and the majority of fermentation inhibitors arising from pretreatment of lignocellulosic feedstock.

Typically, wheat straw is heated by steam to a temperature between 180 and 200° C. with a residence time of 5-15 min. The pretreated biomass is unloaded from the pressure reactor and washed and pressed. Released steam is collected and reused for evaporation of the liquid fraction to feed molasses.

Enzymatic Hydrolysis:

Subsequent hydrolysis of sugar polymers may be carried out by the addition of cellulases and hemicellulases, either prior to fermentation or during fermentation or both inter alia a simultaneous saccharification and fermentation process.

Hexose

Hexose sugars have 6 carbon atoms. Aldohexoses have an aldehyde at position 1, and ketohexoses having a ketone at position 2. Glucose is an example of an aldohexose. Fructose is an example of a ketohexose.

Pentose

Pentose sugars have 5 carbon atoms. Pentoses either have an aldehyde functional group in position 1 (aldopentoses) or a ketone functional group in position 2 (ketopentoses).

Aldopentose

Preferably said aldopentose is selected from the group consisting of xylose, arabinose, ribose and lyxose. More preferably the aldopentose is xylose or arabinose.

In a preferred aspect said aldopentose is xylose. More preferably said aldopentose is D-xylose.

Ketopentose

Preferably said ketopentose is xylulose or ribulose.

In one preferred aspect said ketopentose is xylulose. More preferably said ketopentose is D-xylulose.

In one preferred aspect said ketopentose is ribulose. More preferably said ribulose is D-ribulose.

Conversion of an Aldopentose a Ketopentose

Examples of an aldopentose which is converted to a ketopentose include but are not limited to: the conversion of xylose to xylulose; the conversion of arabinose to xylulose; the conversion of arabinose to ribulose; the conversion of lyxose to xylulose; the conversion of ribose to ribulose; the conversion of D-xylose to D-xylulose; the conversion of L-arabinose to L-xylulose or D-xylulose; the conversion of L-arabinose to L-ribulose; the conversion of D-lyxose to D-xylulose; and the conversion of D-ribose to D-ribulose.

Without wishing to be bound by theory, typically the enzymes involved in the conversion of D-xylose to D-xylulose in fungi are xylose reductase and D-xylulose reductase.

In bacteria, without wishing to be bound by theory, the enzyme which is typically involved in the conversion of D-xylose to D-xylulose is xylose isomerase.

Without wishing to be bound by theory, the enzymes which are generally involved in the conversion of L-arabinose to L-xylulose in fungi are arabinose reductase, L-arabinitol 4-dehydrogenase, L-xylulose reductase and D-xylulose reductase.

In bacteria, without wishing to be bound by theory, typically the enzyme involved in the conversion of L-arabinose to L-ribulose is L-arabinose isomerase.

Without wishing to be bound by theory, the enzyme which may be involved in the conversion of D-lyxose to D-xylulose in bacteria is lyxose isomerase.

Without wishing to be bound by theory, the enzyme which may be involved in the conversion of D-ribose to D-ribulose is D-ribose isomerase.

Enzymes

The enzyme nomenclature numbers (EC numbers) mentioned herein refer to the recommendations of the Nomenclature Committee of the International Union of Biochemistry and Molecular Biology on the nomenclature and classification of enzymes published in 1992.

The enzymes mentioned herein can be produced by nucleotide sequences derived from a wide variety of sources. In one aspect, the nucleotide sequences encoding the enzymes mentioned herein may be derived or derivable from *Lactococcus lactis* subsp. *lactis*, *Geobacillus stearothermophilus*, *Enterococcus faecalis*, *Piromyces* sp, *Thermoanaerobacter thermohydrosulfuricus*, *Pichia stipitis*, or *Saccharomyces cerevisiae*.

Aldose-1-Epimerase (EC 5.1.3.3)

An aldose-1-epimerase mentioned herein is capable of acting on the aldopentose.

Aldose-1-epimerase has the EC nomenclature number 5.1.3.3. Aldose-1-epimerase may be referred to as a mutarotase or an aldose mutarotase.

The term aldose-1-epimerase refers to an enzyme which is capable of converting an α-aldopentose to a β-aldopentose and vice versa.

In a preferred embodiment the aldose-1-epimerase is encoded by a nucleotide sequence selected from the group consisting of: AAD20257 version 1, ABX75760 version 1, AAK05605 version 1, AAD20245 version 1, AAD20251 version 1, ABJ73095 version 1, ABI49935 version 1 and AAO80762 version 1 (NCBI accession numbers). More preferably the aldose-1-epimerase is selected from the group consisting of AAD20257, ABX75760, AAK05605, AAD20245 and AAD20251.

Examples of aldose-1-epimerases suitable for use as described herein include aldose-1-epimerase encoded by: the nucleotide sequence of the *Lactococcus lactis* aldose-1-epimerase gene (NCBI accession number AAD20245 version 1); the nucleotide sequence of the *Saccharomyces cerevisiae* GAL10 gene (in particular, the part encoding an amino acid sequence having mutarotase activity); and the nucleotide sequence of the *Saccharomyces cerevisiae* strain D0002 GAL10 gene (in particular, the part encoding an amino acid sequence having mutarotase activity).

Aldose Reductase (EC 1.1.1.21)

Aldose reductase has the EC nomenclature number 1.1.1.21. Aldose reductase may be referred to as: polyol dehydrogenase, aldehyde reductase, ALR2, NADPH-aldopentose reductase, NADPH-aldose reductase, alditol:NADP oxidoreductase or alditol:NADP$^+$ 1-oxidoreductase.

The term aldose reductase refers to an enzyme which is capable of converting an alditol to an aldose and vice versa.

An aldose reductase may reduce more than one type of aldose. For example, the same enzyme may be capable of reducing both D-xylose and L-arabinose such an enzyme may thus be called aldose reductase or, it may be called more specifically after one of the substrates, e.g. xylose reductase.

Xylose Reductase (EC 1.1.1.21)

In one embodiment, the aldose reductase is a xylose reductase. Xylose reductase has the EC nomenclature number 1.1.1.21.

The term xylose reductase refers to an enzyme which is capable of converting D-xylose to xylitol and vice versa.

A xylose reductase mentioned herein is capable of acting on D-xylose.

Examples of xylose reductases suitable for use as described herein include xylose reductase encoded by: the nucleotide sequence of *Pichia stipitis* xylose reductase gene (PsXR); the nucleotide sequence of *Pichia stipitis* strain DSM3651 xylose reductase gene (PsXR)—NCBI accession number X59465 version 1; the nucleotide sequence of *Candida tenuis* (said nucleotide sequence encoding xylose reductase can be obtained as described by Kavanagh et al, 2003); and the nucleotide sequence of *Neurospora crassa* (said nucleotide sequence encoding xylose reductase can be obtained as described by Woodyer et al, 2005).

Arabinose Reductase (EC 1.1.1.21)

In another embodiment, the aldose reductase is an arabinose reductase. Arabinose reductase has the EC nomenclature number 1.1.1.21.

The term arabinose reductase refers to an enzyme which is capable of converting L-arabinose to L-arabitol and vice versa.

An arabinose reductase mentioned herein is capable of acting on L-arabinose.

D-xylose reductases currently known in the art may also act on L-arabinose as a substrate with similar activity. Hence, the term L-arabinose reductase may also refer to enzymes which are classified as being D-xylose reductases, and the xylose reductases mentioned herein as suitable for introducing xylose metabolism are similarly suitable for use in introducing arabinose metabolism to a microorganism.

In a further embodiment, the aldose reductase may be capable of converting L-lyxose to L-arabitol and vice versa. In another embodiment, the aldose reductase may be capable of converting D-lyxose to D-arabitol and vice versa.

In another embodiment, the aldose reductase may be capable of converting ribose to ribitol (in particular D-ribose to D-ribitol) and vice versa.

Xylulose Reductase (EC 1.1.1.9 and EC 1.1.1.10)

The term xylulose reductase encompasses D-xylulose reductase and L-xylulose reductase.

D-xylulose reductase (EC 1.1.1.9)

D-xylulose reductase has the EC nomenclature number 1.1.1.9. D-xylulose reductase may be referred to as xylitol dehydrogenase, xylitol-2-dehydrogenase, 2,3-cis-polyol (DPN)dehydrogenase (C3-5), NAD-dependent xylitol dehydrogenase, erythritol dehydrogenase or pentitol-DPN dehydrogenase.

The term D-xylulose reductase refers to an enzyme which is capable of converting xylitol to D-xylulose and vice versa.

A D-xylulose reductase mentioned herein is capable of acting on xylitol.

Examples of D-xylulose reductases suitable for use as described herein include D-xylulose reductase encoded by: the nucleotide sequence of *Pichia stipitis* D-xylulose gene (PsXDH); and the nucleotide sequence of *Pichia stipitis* strain DSM3651 D-xylulose reductase gene (PsXDH)—NCBI accession number X55392 version 1.

L-Xylulose Reductase (EC 1.1.1.10)

L-xylulose reductase has the EC nomenclature number 1.1.1.10. L-xylulose reductase may be referred to as L xylitol dehydrogenase.

The term L-xylulose reductase refers to an enzyme which is capable of converting L-xylulose to xylitol and vice versa.

An L-xylulose reductase mentioned herein is capable of acting on L-xylulose.

A nucleotide sequence encoding L-xylulose reductase may be obtained from *Aspergillus niger* as described by Witteveen et al (1994) or from the yeast *Ambrosiozyma monospora* (Verho et al, 2004).

Xylulokinase (EC 2.7.1.17)

Xylulokinase has the EC nomenclature number 2.7.1.17. Xylulokinase may be referred to as D-xylulokinase.

The term xylulokinase refers to an enzyme which is capable of converting D-xylulose to D-xylulose 5-phosphate and vice versa.

A xylulokinase mentioned herein is capable of acting on D-xylulose.

Examples of xylulokinases suitable for use as described herein include xylulokinase encoded by: the nucleotide sequence of *Pichia stipitis* xylulokinase gene (PsXKS); the nucleotide sequence of *Pichia stipitis* strain DSM3651 xylulokinase gene (PsXKS)—NCBI accession number AF127802 version 1; the nucleotide sequence of *S. cerevisiae* xylulokinase gene (ScXKS); and the nucleotide sequence of *S. cerevisiae* strain D0002 xylulokinase gene (ScXKS)—NCBI accession number X61377 version 1.

Xylose Isomerase (EC 5.3.1.5)

Xylose isomerase has the EC nomenclature number EC 5.3.1.5. Xylose isomerase may be referred to as D-xylose isomerase, D-xylose ketoisomerase, or D-xylose ketol-isomerase.

The term xylose isomerase refers to an enzyme which is capable of converting D-xylose to D-xylulose and vice versa.

A xylose isomerase mentioned herein is capable of acting on D-xylose.

Examples of xylose isomerases suitable for use as described herein include xylose isomerase encoded by: the nucleotide sequence of *Piromyces* xylose isomerase gene (PmXI); the nucleotide sequence of *Piromyces* sp E2 xylose isomerase gene (PmXI)—NCBI accession number AJ1249909 version 1; and the nucleotide sequence of *Thermoanaerobacter thermohydrosulfuricus* xylose isomerase gene (ThXI)—NCBI accession number D00756 version 1; SEQ ID No 2 and SEQ ID No 3.

D-arabinitol 4-dehydrogenase (EC 1.1.1.11)

D-arabinitol 4-dehydrogenase has the EC nomenclature number 1.1.1.11. D-arabinitol 4-dehydrogenase may be referred to as D-arabitol dehydrogenase or arabitol dehydrogenase.

The term D-arabinitol 4-dehydrogenase refers to an enzyme which is capable of converting D-arabinitol to D-xylulose and vice versa.

A D-arabinitol 4-dehydrogenase mentioned herein is capable of acting on D-arabinitol.

A suitable D-arabinitol 4-dehydrogenase and the corresponding gene is described by Cheng et al 2005.

L-Arabinitol 4-Dehydrogenase (EC 1.1.1.12)

L-arabinitol 4-dehydrogenase has the EC nomenclature number 1.1.1.12. L-arabinitol 4-dehydrogenase may be referred to as L-arabitol 4-dehydrogenase or pentitol-DPN dehydrogenase.

The term L-arabinitol 4-dehydrogenase refers to an enzyme which is capable of converting L-arabinitol to L-xylulose and vice versa.

An L-arabinitol 4-dehydrogenase mentioned herein is capable of acting on L-arabinitol.

A suitable L-arabinitol 4-dehydrogenase and the corresponding gene is described in Richard et al (2001).

L-Arabinose Isomerase (EC 5.3.1.4)

L-arabinose isomerase has the EC nomenclature number 5.3.1.4. L-arabinose isomerase may be referred to as L-arabinose ketol-isomerase.

The term L-arabinose isomerase refers to an enzyme which is capable of converting L-arabinose to L-ribulose and vice versa.

An L-arabinose isomerase mentioned herein is capable of acting on L-arabinose.

An example of a nucleotide sequence encoding L-arabinose isomerase is the nucleotide sequence which may be obtained from *Lactobacillus plantarum* strain NCIMB8826 (ATCC 14917) (gene described in NCBI accession code NC_004567 version 1).

Ribulokinase (EC 2.7.1.16)

Ribulokinase has the EC nomenclature number 2.7.1.16. Ribulokinase may be referred to as L-ribulokinase.

The term ribulokinase refers to an enzyme which is capable of converting (i) L-ribulose to L-ribulose 5-phosphate and vice versa; and/or (ii) D-ribulose to D-ribulose 5-phosphate and vice versa.

A ribulokinase mentioned herein is capable of acting on L-ribulose and/or D-ribulose.

A suitable nucleotide sequence encoding ribulokinase may be obtained from *Lactobacillus plantarum* strain NCIMB8826 (ATCC 14917) (gene described in NCBI accession code NC_004567 version 1).

L-ribulose phosphate 4-epimerase (EC 5.1.3.4)

L-ribulose phosphate 4-epimerase has the EC nomenclature number 5.1.3.4. L-ribulose phosphate 4-epimerase may be referred to as ribulose phosphate 4-epimerase, phosphoribulose isomerase, L-ribulose 5-phosphate 4-epimerase, AraD or L-Ru5P.

The term L-ribulose phosphate 4-epimerase refers to an enzyme which is capable of converting L-ribulose 5-phosphate to D-xylulose 5-phosphate and vice versa.

An L-ribulose phosphate 4-epimerase mentioned herein is capable of acting on L-ribulose 5-phosphate.

A suitable nucleotide sequence encoding L-ribulose phosphate 4-epimerase may be obtained from *Lactobacillus plantarum* strain NCIMB8826 (ATCC 14917) (gene described in NCBI accession code NC_004567 version 1).

D-Ribitol 4-Dehydrogenase

D-ribitol 4-dehydrogenase has the EC nomenclature number 1.1.1.56. This enzyme may also be referred to as ribitol 2-dehydrogenase, adonitol dehydrogenase or ribitol dehydrogenase.

The term D-ribitol 4-dehydrogenase refers to an enzyme which is capable of converting ribitol to D-ribulose and vice versa.

A D-ribitol 4-dehydrogenase mentioned herein is capable of acting on D-ribitol.

A suitable D-ribitol 4-dehydrogenase and the corresponding gene is described by Dothie et al, 1985.

D-lyxose Isomerase (EC 5.3.1.15)

D-lyxose isomerase has the EC nomenclature number 5.3.1.15. This enzyme may also be referred to as D-lyxose ketol-isomerase.

The term D-lyxose isomerase refers to an enzyme which is capable of converting D-lyxose to D-xylulose and vice versa.

A D-lyxose isomerase mentioned herein is capable of acting on D-lyxose.

A nucleotide sequence encoding a D-lyxose/L-ribose isomerase may be cloned from the organism *Acinetobacter* sp. strain DL-28 (Shimonishi and Izumori, 1996) or from *Aerobacter aerogenes* (Anderson and Allison, 1965).

Ribose Isomerase (EC 5.3.1.20)

Ribose isomerase has the EC nomenclature number 5.3.1.20. This enzyme may also be referred to as D-ribose isomerase or D-ribose ketol-isomerase.

The term ribose isomerase refers to an enzyme which is capable of converting D-ribose to D-ribulose and vice versa.

A ribose isomerase mentioned herein is capable of acting on D-ribose.

D-ribose isomerase has been found in the organism *Mycobacterium smegmatis* (Izumori et al, 1975), from where it may be cloned.

Ribulose-5-phosphate 3-epimerase (EC 5.1.3.1)

Ribulose-5-phosphate 3-epimerase has the EC nomenclature number 5.1.3.1. This enzyme may also be referred to as: pentose-5-phosphate 3-epimerase, phosphoketopentose 3-epimerase, phosphoketopentose epimerase, phosphoribulose epimerase, ribulose-phosphate 3-epimerase; D-ribulose 5-phosphate epimerase; D-ribulose phosphate-3-epimerase; D-ribulose-5-P 3-epimerase; D-xululose-5-phosphate 3-epimerase; erythrose-4-phosphate isomerase; ribulose 5-phosphate 3-epimerase; and xylulose phosphate 3-epimerase.

The term ribulose-5-phosphate 3-epimerase refers to an enzyme which is capable of converting D-ribulose 5-phosphate to D-xylulose 5-phosphate and vice versa.

Examples of ribulose-5-phosphate 3-epimerase suitable for use as described herein include ribulose-5-phosphate 3-epimerase encoded by: the nucleotide sequence of the *S. cerevisiae* RPE1 gene; the nucleotide sequence of the *S. cerevisiae* strain D0002 RPE1 gene; the nucleotide sequence of NCBI accession code NP_012414 version 1; and the ribulose-5-phosphate isomerase from *P. stiptitis* that can be found in NCBI accession number NP_012414 version 1.

Ribose-5-Phosphate Isomerase (EC 5.3.1.6)

Ribose-5-phosphate isomerase has the EC nomenclature number 5.3.1.6. This enzyme may also be referred to as phosphopentoisomerase, phosphopentoseisomerase, phosphopentosisomerase, phosphoriboisomerase, ribose 5-phosphate epimerase, ribose phosphate isomerase, 5-phosphoribose isomerase, or D-ribose-5-phosphate ketol-isomerase.

The term ribose-5-phosphate isomerase refers to an enzyme which is capable of converting D-ribose 5-phosphate to D-ribulose 5-phosphate and vice versa.

Examples of ribose-5-phosphate isomerase suitable for use as described herein include ribose-5-phosphate ketol-isomerase encoded by: the nucleotide sequence of the *S. cerevisiae* RKI1 gene; the nucleotide sequence of the *S. cerevisiae* strain D0002 RKI1 gene; the nucleotide sequence of NCBI accession code X94335 version 1; the nucleotide sequence of NCBI accession code NP_014738 version 1, and the ribose-5-phosphate isomerase from *P. stiptitis* that can be found in accession NC_009043 version 1.

Transketolase (EC 2.2.1.1)

Transketolase has the EC nomenclature number 2.2.1.1. This enzyme may also be referred to as glycolaldehydetransferase.

The term transketolase refers to an enzyme which is capable of converting sedoheptulose 7-phosphate+D-glyceraldehyde 3-phopshate to D-ribose 5-phospate+D-xylulose 5-phosphate and vice versa.

Examples of transketolases suitable for use as described herein include transketolase encoded by: the nucleotide sequence of the *Saccharomyces cerevisiae* TKL1 gene; the nucleotide sequence of the *Saccharomyces cerevisiae* strain D0002 TKL1 gene; the nucleotide sequence of NCBI accession code X73224 version 1; the nucleotide sequence of NCBI accession code NP_015399 version 1, and the transketolase from *P. stiptitis* that can be found in accession CP000496 version 1.

Transaldolase (EC 2.2.1.2)

Transaldolase has the EC nomenclature number 2.2.1.2. This enzyme may also be referred to as dihydroxyacetonetransferase, dihydroxyacetone synthase, formaldehyde transketolase or glycerone transferase.

The term transaldolase refers to an enzyme which is capable of converting sedoheptulose 7-phosphate+D-glyceraldehyde 3-phopshate to D-erythrose 4-phospate+D-fructose 6-phosphate and vice versa.

Examples of transaldolases suitable for use as described herein include transaldolase encoded by: the nucleotide sequence of the *Saccharomyces cerevisiae* TAL1 gene; the nucleotide sequence of the *Saccharomyces cerevisiae* strain D0002 TAL1 gene; the nucleotide sequence of NCBI accession code X15953 version 1; the nucleotide sequence of NCBI accession code NP_013458 version 1, and the transaldolase from *P. stiptitis* that can be found in accession CP000502 version 1.

Aldopentose Assay

The amount of an aldopentose in a solution (such as a culture medium) may be determined colorimetrically by the phloroglucinol method, as described by Ebert et al (A Simplified, calorimetric Micromethod for Xylose in Serum or Urine, with Phloroglucinol, 1979, *Clin. Chem.* 25, no. 8, pp. 1440-1443).

The colour reagent consists of 0.5 g phloroglucinol (1,3,5 trihydroxybenzene), 100 ml glacial acetic acid and 10 ml conc. HCl. 50 µl of sample is added 950 µl of the colour reagent. The mixture is heated to 100° C. for 4 minutes, and the absorbance of the mixture is read at 554 nm. The amount of an aldopentose in the sample is determined according to a standard curve made with the same aldopentose as standard. This method may be used to determine the amount of xylose, arabinose, lyxose and ribose in a culture medium.

Interconversion Assay

The ability of microorganisms to catalyse the conversion between α-aldopentose and β-aldopentose can be assayed by various methods. For example, the interconversion between the alpha and the beta anomer of aldoses may be followed by NMR, for example as explained by Ryu et al (2004), or by a coupled assay, where the activity of an enzyme, specific for one of the anomers, is followed, as described by Brahma and Bhattacharyya (2004).

Ketopentose Assay

The amount of a ketopentose in a solution (such as a culture medium) may be determined colorimetrically by the cysteine-carbazole method as described by Zacharias Dische and Ellen Borenfreund (1951; J. Biol. Chem. 192 (2): 583).

Ethanol Assay

The amount of the biofuel as ethanol, in a solution (such as a culture medium) may be determined by the use of a commercially available ethanol assay, the K-ETOH Kit, manufactured and sold by Megazyrne International, Bray Business Park, Bray, Co. Wicklow, Ireland; or it may be determined by, for example, the use of gas chromatography.

Pentose Phosphate Pathway

Ketopentoses are converted into ethanol via the pentose phosphate pathway. An example of this is shown in FIG. 4.

Examples of enzymes involved in the pentose phosphate pathway include: transketolase, transaldolase, ribose-5-phosphate ketol-isomerase and ribulose-5-phosphate 3-epimerase.

In one embodiment the microorganism according to the present invention has also been transformed to express or overexpress one or more enzymes involved in the pentose phosphate pathway.

In one embodiment the microorganism according to the present invention has also been transformed with one or more nucleotide sequences that cause the microorganism to overexpress one or more enzymes involved in the pentose phosphate pathway. For example, a promoter is inserted into the genome of a microorganism which enables the microorganism to overexpress an endogenous nucleotide sequence encoding an enzyme involved in the pentose phosphate pathway.

In another embodiment the microorganism has been transformed with one or more nucleotide sequences encoding one or more enzymes involved in the pentose phosphate pathway. For example, the microorganism is transformed with an expression vector comprising a nucleotide sequence encoding one or more enzymes involved in the pentose phosphate pathway.

Preferably the expression vector mentioned herein comprises one or more promoters capable of overexpressing one or more nucleotide sequences encoding one or more enzymes involved in the pentose phosphate pathway. Examples of such promoters include the GPD promoter, the TEF promoter and the ADP promoter. Preferred promoters which may be used to overexpress one or more nucleotide sequences encoding one or more enzymes involved in the pentose phosphate pathway can be any of the regulatory elements controlling the expression of nucleotide sequences encoding proteins involved in glycolysis and glucose fermentation.

As used herein, the term "overexpress" in the phrase "one or more nucleotide sequences that cause the microorganism to overexpress one or more enzymes involved in the pentose phosphate pathway" and "one or more promoters capable of overexpressing one or more nucleotide sequences encoding one or more enzymes involved in the pentose phosphate pathway" refers to an increase in expression from zero to a level of expression or going from a lower level of expression to a higher level of expression (e.g. upregulation) when the transformed microorganism is compared to the equivalent microorganism prior to transformation. Microorganisms overexpressing one or more enzymes involved in the pentose phosphate pathway have an increased ability to catalyse the conversion of a ketopentose (such as xylulose 5-phosphate) to a biofuel (such as ethanol).

Preferably said transformed microorganism which overexpresses one or more enzymes involved in the pentose phosphate pathway is able to catalyse the conversion of a ketopentose (such as xylulose 5-phosphate) to a biofuel (such as ethanol) by a rate which is at least 10%, 15%, 20% or 25% higher than an untransformed microorganism.

Examples of microorganisms overexpressing one or more enzymes involved in the pentose phosphate pathway include: (i) microorganisms transformed with one or more expression vectors encoding one or more of transketolase, transaldolase, ribose-5-phosphate ketol-isomerase and ribulose-5-phosphate 3-epimerase; and (ii) microorganisms transformed to upregulate the expression of one or more endogenous nucleotide sequences encoding one or more of transketolase, transaldolase, ribose-5-phosphate ketol-isomerase and ribulose-5-phosphate 3-epimerase (prior to transformation said microorganism was capable of expressing one or more of these enzymes for a given set of culture conditions during exponential growth but after transformation said microorganism is capable of expressing one or more of these enzymes at a higher level, in the same culture conditions, during exponential growth).

The invention will now be further described by way of Examples, which are meant to serve to assist one of ordinary skill in the art in carrying out the invention and are not intended in any way to limit the scope of the invention.

EXAMPLES

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example Sambrook et al, 1989; Ausubel, F. M. et al. 1995; Roe et al 1996; Gait, 1984; and Lilley and Dahlberg, 1992. Each of these general texts is herein incorporated by reference.

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in*

Example 1a

Construction of Synthetic Mutarotase Gene (Aldose-1-Epimerase) of *Lactococcus lactis* Based on NCBI Accession Code AAD20245 Version 1

The entire *L. lactis* aldose-1-epimerase gene (LlMR) was synthesized and assembled by Geneart AG (Regensburg, Germany). Codon usage in the sequence was optimised based on the yeast codon usage table from the Kazusa codon usage database (Nakamura et al., 2000). Flanking the open reading frame, a restriction-site for NheI, proximal to the ATG-start codon and a restriction-site for XhoI, distal to the stop-codon, were included in the synthetic construct. The integrity of the LlMR synthetic gene was determined by sequencing of both strands. The nucleotide sequence of LlMR including the flanking restriction-sites is identified as SEQ.ID.NO. 1 (i.e. AAD20245) and the amino acid sequence encoded by this nucleotide sequence is identified as SEQ ID No 47. The harbouring plasmid was named 0717050pGA14.

Example 1b

Construction of Synthetic Xylose Isomerase Gene of *Piromyces* sp. E2 Based on NCBI Accession Code AJ249909 Version 1

The entire *Piromyces* xylose isomerase gene (PmXI) was synthesized and assembled by Geneart AG (Regensburg, Germany). Codon usage in the sequence was optimised based on the yeast codon usage table from the Kazusa codon usage database (Nakamura et al., 2000). Flanking the open reading frame, a restriction-site for NheI, proximal to the ATG-start codon and a restriction-site for XhoI, distal to the stop-codon, were included in the synthetic construct. The integrity of the PmXI synthetic gene was determined by sequencing of both strands. The nucleotide sequence of PmXI including flanking restriction-sites is identified as SEQ.ID.NO. 2 and the amino acid sequence encoded by this nucleotide sequence is identified as SEQ ID No 48. The harbouring plasmid was named 0717049pGA15.

Example 1c

Construction of Synthetic Xylose Isomerase (XyIA) Gene of *Thermoanaerobacter thermohydrosulfuricus* Based on NCBI Accession Code D00756 Version 1

The entire *T. thermohydrosulfuricus* xylose isomerase gene (ThXI) was synthesized and assembled by Geneart AG (Regensburg, Germany). Codon usage in the sequence was optimised based on the yeast codon usage table from the Kazusa codon usage database (Nakamura et al., 2000). Flanking the open reading frame, a restriction-site for NheI, proximal to the ATG-start codon and a restriction-site for XhoI, distal to the stop-codon, were included in the synthetic construct. The integrity of the ThXI synthetic gene was determined by sequencing of both strands. The nucleotide sequence of ThXI including flanking restriction-sites is identified as SEQ.ID.NO. 3 and the amino acid sequence encoded by this nucleotide sequence is identified as SEQ ID No 49. The harbouring plasmid was named 0717046pGA14.

Example 2a

TOPO Cloning of the D-Xylulolkinase Gene from the *Pichia stipitis* Strain DSM3651 Based on NCBI Accession Code AF127802 Version 1

The entire *P. stipitis* D-xylulokinase gene (PsXKS) was PCR amplified from DNA obtained from the strain DSM3651 using the primers identified by SEQ.ID.NO. 4 and SEQ.ID.NO. 5. A restriction-site for NheI, proximal to the ATG-start codon and a restriction-site for XhoI, distal to the stop-codon was introduced flanking the PsXKS gene. As template, DNA from the *P. stipitis* strain was used in a concentration of 0.2 ng/µl PCR-reaction. PCR was performed at 30 cycles of 30 seconds at 96° C., 30 seconds at 50° C., and 150 seconds at 72° C., followed by a final incubation of 10 minutes at 72° C. using Phusion High Fidelity DNA polymerase (Finnzymes Oy, Finland). The PCR product was electrophoretically separated on a 1% low melt agarose gel and a 1891 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named pCR-Blunt 2 P.stip XKS.

Example 2b

TOPO Cloning of the D-Xylose Reductase Gene from the *Pichia stipitis* Strain DSM3651 Based on NCBI Accession Code X59465 Version 1

The entire *P. stipitis* xylose reductase gene (PsXR) was PCR amplified from DNA obtained from the strain DSM3651, using the primers identified by SEQ.ID.NO. 6 and SEQ.ID.NO. 7. A restriction-site for NheI, proximal to the ATG-start codon and a restriction-site for XhoI, distal to the stop-codon was introduced flanking the PsXR gene. As template, DNA from the *P. stipitis* strain was used in a concentration of 0.2 ng/µl PCR-reaction. PCR was performed at 30 cycles of 30 seconds at 96° C., 30 seconds at 50° C., and 150 seconds at 72° C., followed by a final incubation of 10 minutes at 72° C. using Phusion High Fidelity DNA polymerase (Finnzymes Oy, Finland). The PCR product was electrophoretically separated on a 1% low melt agarose gel and a 976 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named pCR-Blunt 2 P.stip XR.

Example 2c

TOPO Cloning of the Xylitol Dehydrogenase (D-Xylulose Reductase Gene from the *Pichia stipitis* Strain DSM3651 Based on NCBI Accession Code X55392 Version 1

The entire *P. stipitis* xylitol dehydrogenase gene (PsXDH) was PCR amplified from DNA obtained from the strain DSM3651, using the primers identified by SEQ.ID.NO. 8 and SEQ.ID.NO. 9. A restriction-site for NheI, proximal to the ATG-start codon and a restriction-site for XhoI, distal to the stop-codon was introduced flanking the PsXDH gene. As template, DNA from the *P. stipitis* strain was used in a concentration of 0.2 ng/µl PCR-reaction. PCR was performed at 30 cycles of 30 seconds at 96° C., 30 seconds at 50° C., and 150 seconds at 72° C., followed by a final incubation of 10 minutes at 72° C. using Phusion High Fidelity DNA polymerase (Finnzymes Oy, Finland). The PCR product was electrophoretically separated on a 1% low melt agarose gel and a 1108 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named pCR-Blunt 2 P.stip XDH.

Example 2d

TOPO Cloning of the L-Arabinose Isomerase Gene (EC 5.3.1.4) from the *Lactobacillus plantarum* Strain NCIMB8826 (ATCC 14917) Based on NCBI Accession Code NC_004567 Version 1

The entire *L. plantarum* L-arabinose isomerase gene (LpAraA) is PCR amplified from DNA obtained from the strain ATCC 14917, using the primers identified by SEQ.ID.NO. 10 and SEQ.ID.NO. 11. A restriction-site for NheI, proximal to the ATG-start codon and a restriction-site for XhoI, distal to the stop-codon are introduced flanking the LpAraA gene. As template, DNA from the *L. plantarum* strain is used in a concentration of 0.2 ng/µl PCR-reaction. PCR is performed at 30 cycles of 30 seconds at 96° C., 30 seconds at 55° C., and 60 seconds at 72° C., followed by a final incubation of 10 minutes at 72° C. using Phusion High Fidelity DNA polymerase (Finnzymes Oy, Finland). The PCR product is electrophoretically separated on a 0.7% low melt agarose gel and a 1444 bp fragment is isolated. The DNA fragment is TOPO cloned into the pCR-Blunt II-TOPO vector (Invitrogen, USA) according to the manufacturer's instructions and the resulting plasmid is used for the transformation of *E. coli* TOP10.

Example 2e

TOPO Cloning of the L-Ribulokinase Gene (EC 2.7.1.16) from the *Lactobacillus plantarum* Strain NCIMB8826 (ATCC 14917) Based on NCBI Accession Code NC_004567 Version 1

The entire *L. plantarum* L-ribulokinase gene (LpAraB) is PCR amplified from DNA obtained from the strain ATCC14917, using the primers identified by SEQ.ID.NO. 12 and SEQ.ID.NO. 13. A restriction-site for NheI, proximal to the ATG-start codon and a restriction-site for XhoI, distal to the stop-codon are introduced flanking the LpAraB gene. As template, DNA from the *L. plantarum* strain is used in a concentration of 0.2 ng/µl PCR-reaction. PCR is performed at 30 cycles of 30 seconds at 96° C., 30 seconds at 55° C., and 60 seconds at 72° C., followed by a final incubation of 10 minutes at 72° C. using Phusion High Fidelity DNA polymerase (Finnzymes Oy, Finland). The PCR product is electrophoretically separated on a 0.7% low melt agarose gel and a 1618 bp fragment is isolated. The DNA fragment is TOPO cloned into the pCR-Blunt II-TOPO vector (Invitrogen, USA) according to the manufacturer's instructions and the resulting plasmid is used for the transformation of *E. coli* TOP10.

Example 2f

TOPO Cloning of the L-Ribulose-5-Phosphate 4-Epimerase Gene (EC 5.1.3.4) from the *Lactobacillus plantarum* Strain NCIMD38826 (ATCC 14917) Based on NCBI Accession Code NC_004567 Version 1

The entire *L. plantarum* L-ribulose-5-phosphate 4-epimerase gene (LpAraD) is PCR amplified from DNA obtained from the strain ATCC 14917, using the primers identified by SEQ.ID.NO. 14 and SEQ.ID.NO. 15. A restriction-site for NheI, proximal to the ATG-start codon and a restriction-site for XhoI, distal to the stop-codon are introduced flanking the LpAraD gene. As template, DNA from the *L. plantarum* strain was used in a concentration of 0.2 ng/µl PCR-reaction. PCR was performed at 30 cycles of 30 seconds at 96° C., 30 seconds at 55° C., and 60 seconds at 72° C., followed by a final incubation of 10 minutes at 72° C. using Phusion High Fidelity DNA polymerase (Finnzymes Oy, Finland). The PCR product is electrophoretically separated on a 0.7% low melt agarose gel and a 745 bp fragment is isolated. The DNA fragment is TOPO cloned into the pCR-Blunt II-TOPO vector (Invitrogen, USA) according to the manufacturer's instructions and the resulting plasmid is used for the transformation of *E. coli* TOP10.

Example 2g

TOPO Cloning of the GAL10 Gene from the *Saccharomyces cerevisiae* Strain D0002 Based on NCBI Accession Number Code 235888 Version 1

The entire *S. cerevisiae* GAL10 gene (ScGAL10) was PCR amplified from DNA obtained from the *S. cerevisiae* strain D0002 using the primers identified by SEQ.ID.NO. 16. and SEQ.ID.NO. 17. A restriction-site for NheI, proximal to the ATG-start codon and a restriction-site for XhoI, distal to the stop-codon were introduced flanking the ScGAL10 gene. As template, DNA from the *S. cerevisiae* strain was used in a concentration of 0.2 ng/µl PCR-reaction. PCR was carried out for 35 cycles of 30 seconds at 96° C., 30 seconds at 57° C., and 120 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 2116 bp fragment isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named ScGAL-a23a.

Example 2h

TOPO Cloning of a Truncated GAL10 Gene [Nucleotides 1084-2100] from the *Saccharomyces cerevisiae* Strain D0002 Based on NCBI Accession Code 235888 Version 1

The N-terminal truncated *S. cerevisiae* GAL10 gene (ScGAL10Δ) was PCR amplified from DNA obtained from the *S. cerevisiae* strain D0002 using the primers identified by SEQ.ID.NO. 18, and SEQ.ID.NO. 17. A restriction-site for NheI, proximal to a ATG-start codon encoded by the primer and a restriction-site for XhoI, distal to the stop-codon were introduced flanking the ScGAL10Δ gene. As template, DNA from the *S. cerevisiae* strain was used in a concentration of 0.2 ng/µl PCR-reaction. PCR was carried out for 35 cycles of 30 seconds at 96° C., 30 seconds at 57° C., and 120 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 1036 bp fragment isolated. The DNA fragment was TOPO cloned into the pCR-Blunt II-TOPO vector (Invitrogen, USA) according to the manufacturer's instructions and the resulting plasmid used for the transformation of *E. coli* TOP10. The plasmid was named ScGALΔ-a24a.

Example 3a

Construction of Plasmid PmXI-8a Containing the *Piromyces* Xylose Isomerase (PmXI) Gene Under Control of the GPD Promoter and the CYC1 Terminator from *S. cerevisiae*

The *E. coli/S. cerevisiae* high-copy shuttle vector P426-GPD (Mumberg et al., 1995) was digested with SpeI and XhoI and the resulting termini were dephosphorylated with alkaline phosphatase. Similarly, the DNA fragment encoding the *Piromyces* xylose isomerase gene was released from the vector 0717049pGA15 (described in Example 1b) by digestion with NheI and XhoI. The resulting linearized plasmid P426-GPD and the DNA fragment encoding PmXI were electrophoretically separated on a 1% low melt agarose gel and isolated. The two DNA fragments were ligated together resulting in the plasmid named PmXI-8a.

Example 3b

Construction of Plasmid ThXI-5a Containing the *T. thermohydrosulfuricus* Xylose Isomerase (ThXI) Gene Under Control of the GPD Promoter and the CYC1 Terminator from *S. cerevisiae*

The *E. coli/S. cerevisiae* high-copy shuttle vector P426-GPD (Mumberg et al., 1995) was digested with SpeI and XhoI and the resulting termini were dephosphorylated with alkaline phosphatase. Similarly, the DNA fragment encoding the *T. thermohydrosulfuricus* xylose isomerase gene was released from the vector 0717046pGA14 (described in Example 1c) by digestion with NheI and XhoI. The resulting linearized plasmid P426-GPD and the DNA fragment encoding ThXI were electrophoretically separated on a 1% low melt agarose gel and isolated. The two DNA fragments were ligated together resulting in the plasmid named ThXI-5a.

Example 3c

Construction of Plasmid PsXKS-14a Containing the *P. stipitis* D-xylulokinase (PsXKS) Gene Under Control of the GPD Promoter and the CYC1 Terminator from *S. cerevisiae*

The *E. coli/S. cerevisiae* high-copy shuttle vector P425-GPD (Mumberg et al., 1995) was digested with SpeI and XhoI and the resulting termini were dephosphorylated with alkaline phosphatase. Similarly, the DNA fragment encoding the *P. stipitis* xylulose kinase gene was released from the vector pCR-Blunt 2 P.stip XKS (described in Example 2a), by digestion with NheI and XhoI. The resulting linearized plasmid P425-GPD and the DNA fragment encoding PsXKS were electrophoretically separated on a 1% low melt agarose gel and isolated. The two DNA fragments were ligated together resulting in the plasmid named POCKS-14a.

Example 3d

Construction of Plasmids PsXR-24a and PsXR-25 Containing the *P. stipitis* Xylose Reductase (PsXR) Gene Under Control of the GPD Promoter and the CYC1 Terminator from *S. cerevisiae*

The *E. coli/S. cerevisiae* high-copy shuttle vector P424-GPD and the similar low-copy shuttle vector P414-GPD (Mumberg et al., 1995) were digested with SpeI and XhoI and the resulting termini were dephosphorylated with alkaline phosphatase. Similarly, the DNA fragment encoding the *P. stipitis* xylose reductase gene was released from the vector pCR-Blunt 2P.stip XR (described in Example 2b), by digestion with NheI and XhoI. The resulting linearized plasmids P424-GPD and P414-GPD and the DNA fragment encoding PsXR were electrophoretically separated on a 1% low melt agarose gel and isolated. The linearized plasmid P424-GPD was ligated together with the PsXR fragment resulting in the plasmid named PsXR-24a. Likewise, the linearized plasmid P414-GPD was ligated together with the PsXR fragment resulting in the plasmid named PsXR-25a.

Example 3e

Construction of Plasmid PsXDH-11a Containing the *P. Stipitis* Xylitol Dehydrogenase (PsXDH) Gene (Xylulose Reductase) Under Control of the GPD Promoter and the CYC1 Terminator from *S. cerevisiae*

The *E. coli/S. cerevisiae* high-copy shuttle vector P426-GPD (Mumberg et al., 1995) was digested with SpeI and XhoI and the resulting termini were dephosphorylated with alkaline phosphatase. Similarly, the DNA fragment encoding the *P. stipitis* xylulose dehydrogenase gene was released from the vector pCR-Blunt 2 P.stip XDH (described in Example 2c), by digestion with NheI and XhoI. The resulting linearized plasmid P426-GPD and the DNA fragment encoding PsXDH were electrophoretically separated on a 1% low melt agarose gel and isolated. The two DNA fragments were ligated together resulting in the plasmid named PsXDH-11a.

Example 3f

Construction of Plasmids LlMR-36a, LlMR-38a and LlMR-40a Containing the *L. lactis* Mutarotase Gene (LlMR) Gene (Aldose-1-Epimerase) Under Control of Various Promoters and the CYC1 Terminator from *S. cerevisiae*

The *E. coli/S. cerevisiae* low-copy shuttle vectors P413-GPD, P413-ADH and P413-TEF (Mumberg et al., 1995) were digested with SpeI and XhoI and the resulting termini were dephosphorylated with alkaline phosphatase. Similarly, the DNA fragment encoding the *L. lactis* aldose-1-epimerase gene (LlMR) gene was released from the vector 0717050pGA14 (described in Example 1a) by digestion with NheI and XhoI. The resulting linearized plasmids P413-GPD, P413-ADH and P413-TEF and the DNA fragment encoding LlMR were electrophoretically separated on a 1% low melt agarose gel and isolated. The linearized plasmid P413-GPD was ligated together with the LlMR fragment resulting in the plasmid named LlMR-36a. Likewise, the linearized plasmid P413-ADH was ligated together with the LlMR fragment resulting in the plasmid named LlMR38a. Finally, the linearized plasmid P413-TEF was ligated together with the LlMR fragment resulting in the plasmid named LlMR-40a.

P413-GPD comprises the promoter from the gene TDH3 encoding Glyceraldehyde-3-phosphate dehydrogenase, (also known as GAPDH) isozyme 3; P413-ADH comprises the promoter from the gene ADH1 encoding Alcohol dehydrogenase I; and P413-TEF comprises the promoter from the gene TEF2 encoding Translational elongation factor EF-1 alpha.

Example 3g

Construction of a Yeast Expression Plasmid Containing the *L. plantarum* L-Arabinose Isomerase Gene (LpAraA) Gene Under Control of the GPD Promoter and the CYC1 Terminator from *S. cerevisiae*

The *E. coli/S. cerevisiae* high-copy shuttle vector P426-GPD (Mumberg et al., 1995) is digested with SpeI and XhoI and the resulting termini is dephosphorylated with alkaline phosphatase. Similarly, the DNA fragment encoding the *L. plantarum* L-arabinose isomerase gene (LpAraA) is released from the vector described in Example 2d, by digestion with NheI and XhoI. The resulting linearized plasmid P426-GPD and the DNA fragment encoding LpAraA are electrophoretically separated on a 0.7% low melt agarose gel and isolated. The two DNA fragments are ligated together and the resulting plasmid is used for the transformation of *E. coli* TOP10.

Example 3h

Construction of a Yeast Expression Plasmid Containing the *L. plantarum* L-Ribulokinase Gene (LpAraB) Gene Under Control of the ADH Promoter and the CYC1 Terminator from *S. cerevisiae*

The *E. coli/S. cerevisiae* high-copy shuttle vector P425-ADH (Mumberg et al., 1995) is digested with SpeI and XhoI and the resulting termini is dephosphorylated with alkaline phosphatase. Similarly, the DNA fragment encoding the *L. plantarum* L-ribulokinase gene (LpAraB) is released from the vector described in Example 2e, by digestion with NheI and XhoI. The resulting linearized plasmid P425-ADH and the DNA fragment encoding LpAraB are electrophoretically separated on a 0.7% low melt agarose gel and isolated. The two DNA fragments are ligated together and the resulting plasmid is used for the transformation of *E. coli* TOP10.

Example 3i

Construction of a Yeast Expression Plasmid Containing the *L. plantarum* L-Ribulose-5-phosphate 4-epimerase Gene (LpAraD) Gene Under Control of the GPD Promoter and the CYC1 Terminator from *S. cerevisiae*

The *E. coli/S. cerevisiae* high-copy shuttle vector P424-GPD (Mumberg et al., 1995) is digested with SpeI and XhoI and the resulting termini is dephosphorylated with alkaline phosphatase. Similarly, the DNA fragment encoding the *L. plantarum* L-ribulose-5-phosphate 4-epimerase gene (LpAraD) is released from the vector described in Example 2f, by digestion with NheI and XhoI. The resulting linearized plasmid P424-GPD and the DNA fragment encoding LpAraD are electrophoretically separated on a 0.7% low melt agarose gel and isolated. The two DNA fragments are ligated together and the resulting plasmid is used for the transformation of *E. coli* TOP10.

Example 3j

Construction of a Yeast Expression Plasmid Containing the *S. cerevisiae* Bifunctional Aldose-1-Epimerase/UDP Galactose 4-Epimerase Gene (ScGAL10) Gene Under Control of the ADH Promoter and the CYC1 Terminator from *S. cerevisiae* for Overexpression of Aldose-1-Epimerase The *E. coli/S. cerevisiae* low-copy shuttle vector P413-ADH (Mumberg et al. (1995) Gene 156, p. 119-122) is digested with SpeI and XhoI and the resulting termini subsequently dephosphorylated with alkaline phosphatase. Similarly, the DNA fragment encoding the *S. cerevisiae* bifunctional aldose-1-epimerase/UDP galactose 4-epimerase gene (ScGAL10) is released from the vector ScGAL-a23a (described in Example 2g) by digestion with NheI and XhoI. The resulting linearized plasmid P413-ADH and the DNA fragment encoding ScGAL10 are electrophoretically separated on a 0.7% low melt agarose gel and thereafter isolated. The linearized plasmid P413-ADH is ligated together with the ScGAL10 fragment resulting in the yeast expression plasmid.

Example 3k

Construction of a Yeast Expression Plasmid Containing the Mutarotase Part of the *S. cerevisiae* Aldose-1-Epimerase/UDP Galactose 4-Epimerase Gene (ScGAL10Δ) Gene Under Control of the ADH Promoter and the CYC1 Terminator from *S. cerevisiae* for Overexpression of Aldose-1-Epimerase The gene GAL10 is known to be a bifunctional enzyme containing an epimerase part catalysing the conversion of UDP-galactose to UDP-glucose as well as a mutarotase part catalysing the conversion of α-galactose to β-galactose and vice versa Majumdar et al, 2004.

The *E. coli/S. cerevisiae* low-copy shuttle vector P413-ADH (Mumberg et al. (1995) Gene 156, p. 119-122) is digested with SpeI and XhoI and the resulting termini subsequently dephosphorylated with alkaline phosphatase. Similarly, the DNA fragment encoding the *S. cerevisiae* mutarotase part of the bifunctional aldose-1-epimerase/UDP galactose 4-epimerase gene (ScGAL10Δ) is released from the vector ScGALΔ-a24a (described in Example 2h) by digestion with NheI and XhoI. The resulting linearized plasmid P413-ADH and the DNA fragment encoding ScGAL10Δ are electrophoretically separated on a 0.7% low melt agarose gel and thereafter isolated. The linearized plasmid P413-ADH is ligated together with the ScGAL10Δ fragment resulting in the yeast expression plasmid.

Example 4a

Construction of *S. cerevisiae* Strains Containing the PmXI-8a and the PsXKS-14a Plasmids Together with, Either the LlMR-36a, Limb-38a, LlMR-40a or the Empty P413-CYC Plasmids (Mumberg et al., 1995)

200 ng each of the plasmids were combined and used for the transformation of *S. cerevisiae* yeast strain BY4741 (Euroscaif, Germany) by means of electroporation using the Biorad Gene Pulser II system (Biorad, USA) according to the manufacturer's instructions. Yeast cells were made competent according to a standard protocol (Becker, D. M. and Guarente, 1991). Selection for clones transformed with all three plasmids was done on solid synthetic complete dropout media omitting uracil, histidine and leucine and supplemented with 2% D-glucose (SC-Ura, His, Leu) (Rose et al., 1990). Medium-size primary clones were restreaked on SC-Ura, His, Leu and one colony each of the following was isolated: strain T0062 transformed with the plasmids LlMR-36a, PmXI-8a and PsXKS-14a; strain T0063 with the plasmids LlMR-38a, PmXI-8a and PsXKS-14a; strain T0065 with the plasmids LlMR-40a, PmXI-8a and PsXKS-14a; and finally strain T0067 with the plasmids P413-CYC, PmXI-8a and PsXKS-14a (these plasmid are described in Example 3; P413-CYC is the empty plasmid described in Mumberg et al 1995).

Example 4b

Measurements of D-Xylose Metabolism by Growth Curves of the Yeast Strains T0062, T0063, T0065 and T0067

Changes in the rate of D-xylose metabolism were measured as alterations in the growth rate of the xylose metabolising yeast strains. The four strains were initially adapted to D-xylose metabolism. Each strain was inoculated individually in liquid Synthetic Complete dropout media omitting uracil, histidine and leucine supplemented with 2% D-xylose and 0.2% D-glucose (SCX(+0.2% D-glc)—Ura, His, Len). The cultures were incubated for one week at 30° C. in a shaker running at 225 RPM. After one week, each culture was used to re-inoculate new cultures with liquid Synthetic Complete dropout media omitting uracil, histidine and leucine supplemented with 2% D-xylose and 0.02% D-glucose (SCX(+0.02% D-glc)—Ura, His, Leu). These cultures were incubated for a further week as described above. Growth experiments were initiated by inoculation of SCX-Ura, His, Leu supplemented with 2% D-xylose at an initial cell titre of OD600=0.006/ml. These cultures were incubated as described above. Aliquots were sampled four times with intervals of 24 hours, the optical density, OD600 was measured and a growth curve was determined for each of the four strains. The doubling time (i.e. the time taken for a doubling in the number of microorganisms per ml during the exponential growth phase) was determined, using the time interval of 24-96 hours following the initial lag phase. The following growth data could be determined for the four strains:

| Yeast strain | Specific growth rate ($\mu$) h$^{-1}$ | Final OD600 ml$^{-1}$ |
|---|---|---|
| T0067 | 0.058 | 0.110 |
| T0065 | 0.070 | 0.215 |
| T0063 | 0.079 | 0.441 |
| T0062 | 0.088 | 0.524 |

These results show an increase in the growth rate of about 20% or more in the strains when the aldose-1-epimerase is co-expressed together with the xylose isomerase and D-xylulokinase compared to the isogenic strain not express mutarotase. Compare strains T0056, 10063 and T0062 with 10067 that does not expressing the mutarotase.

In particular, strain 10062 showed an increase in the growth rate of more than 50%. In terms of assimilated carbon, more than 4 fold increase in biomass was achieved in that recombinant yeast strain. Furthermore, the use of different promoters controlling the aldose-1-epimerase, in otherwise isogenic strains, demonstrates an increase carbon flux as a result of an increased promoter strength. This shows that a bottleneck exist prior to the isomerisation of D-xylose in the metabolic pathway of D-xylose catabolism.

Example 5a

Construction of S. cerevisiae Strains Containing the ThXI-5a and the Pocks-14a Plasmids Together with, Either the L1MR-36a, or the Empty P413-CYC Plasmids (Mumberg et al., 1995)

200 ng each of the plasmids were combined and used for the transformation of S. cerevisiae yeast strain BY4741 (Euroscarf, Germany) by means of electroporation using the Biorad Gene Pulser II system (Biorad, USA) according to the manufacturer's instruction. Yeast cells were made competent according to a standard protocol (Becker, D. M. and Guarente, 1991). Selection for clones transformed with all three plasmids was done on solid synthetic complete dropout media omitting uracil, histidine and leucine and supplemented with 2% D-glucose (SC-Ura, His, Leu) (Rose et al., 1990). Medium-size primary clones were restreaked on SC-Ura, His, Leu and one colony each of the following was isolated: strain T0085 transformed with the plasmids L1MR-36a, ThXI-5a and PsXKS-14a; and strain T0086 with the plasmids P413-CYC, ThXI-5a and PsXKS-14a.

Example 5b

Measurements of D-Xylose Metabolism by Growth Curves of the Yeast Strains T0085, and T0086

Changes in the rate of D-xylose metabolism were measured as alterations in the growth rate of the xylose metabolising yeast strains. The two strains were initially adapted to D-xylose metabolism. Each strain was inoculated individually in liquid Synthetic Complete dropout media omitting uracil, histidine and leucine supplemented with 2% D-xylose and 0.2% D-glucose (SCX(+0.2% D-glc)—Ura, His, Leu). The cultures were incubated for one week at 30° C. in a shaker running at 225 RPM. After one week, each culture was used to re-inoculate new cultures with liquid Synthetic Complete dropout media omitting uracil, histidine and leucine supplemented with 2% D-xylose and 0.02% D-glucose (SCX(+0.02% D-glc)—Um, His, Leu). These cultures were incubated for a further week as described above. Growth experiments were initiated by inoculation of SCX-Ura, His, Len supplemented with 2% D-xylose at an initial cell titre of OD600=0.006/ml. These cultures were incubated as described above. Aliquots were sampled four times with intervals of 24 hours, the optical density, OD600 was measured and a growth curve was determined for each of the four strains. The doubling time was determined, using the time interval of 24-96 hours following the initial lag phase. The following growth data could be determined for the two strains:

| Yeast strain | Specific growth rate ($\mu$) h$^{-1}$ | Final OD600 ml$^{-1}$ |
|---|---|---|
| T0086 | 0.056 | 0.101 |
| T0085 | 0.067 | 0.172 |

This demonstrates that an increase in the growth-rate of about 20% can be achieved when the aldose-1-epimerase is co-expressed together with xylose isomerase and D-xyluloki-nase compared to the isogenic strain not express mutarotase. Compare strain T0085 with strain T0086 which does not express the mutarotase.

Example 6a

Construction of S. cerevisiae Strains Containing the PsXR-24a (or the PsXR-25), the PsXDH-11a, and the PsXKS-14a Plasmids Together with, Either the L1MB-38a, or the Empty P423-CYC Plasmids (Mumberg et al., 1995)

200 ng each of the plasmids were combined and used for the transformation of S. cerevisiae yeast strain Y07202 (Eurosearf; Germany) by means of electroporation using the Biorad Gene Pulser II system (Biorad, USA) according to the manufacturer's instruction. Yeast cells were made competent according to a standard protocol (Becker and Guarente, 1991). Selection for clones transformed with all four plasmids simultaneous was done on solid synthetic complete dropout media omitting uracil, histidine, leucine and tryptophan and supplemented with 2% D-glucose (SC-Ura, His, Leu, Trp) (Rose et al., 1990). Medium-size primary clones were restreaked on SC-Ura, His, Leu, Trp and one colony each of the following were isolated: strain T0114 transformed with the plasmids LlMR-38a, PsXR-24a, PsXDH-11a and PsXKS-14a; strain T0117 with the plasmids P423-CYC, PsXR-24a, PsXDH-11a and PsXKS-14a; strain T0123 with the plasmids LlMR-38a, PsXR-25a, PsXDH-11a and PsXKS-14a; and strain T0126 with the plasmids P423-CYC, PsXR-25a, PsXDH-11a and PsXKS-14a.

Example 6b

Measurements of D-Xylose Metabolism by Growth Curves of the Yeast Strains T0114, T0117, T0123 and T0126

Changes in the rate of D-xylose metabolism were measured as alterations in the growth rate of the xylose metabolising yeast strains. The four strains were initially adapted to D-xylose metabolism. Each strain was inoculated individually in liquid Synthetic Complete dropout media omitting uracil, histidine, leucine and tryptophan supplemented with 2% D-xylose and 0.2% D-glucose (SCX(+0.2% D-glc)—Ura, His, Len, Trp). The cultures were incubated for one week at 30° C. in a shaker running at 225 RPM. After one week, each culture was used to re-inoculate new cultures with liquid Synthetic Complete dropout media omitting uracil, histidine, leucine and tryptophan supplemented with 2% D-xylose and 0.02% D-glucose (SCX(+0.02% D-glc)—Ura, His, Leu, Trp). These cultures were incubated for a further week as described above. Growth experiments was initiated by inoculation of SCX-Ura, His, Leu, Trp supplemented with 2% D-xylose at an initial cell titre of OD600=0.006/ml. These cultures were incubated as described above. Aliquots were sampled five times with intervals of 24 hours, the optical density, OD600 was measured and a growth curve was determined for each of the four strains. The doubling time was determined, using the time interval of 24-120 hours following the initial lag phase. The following growth data could be determined for the four strains:

| Yeast strain | Specific growth rate ($\mu$) h$^{-1}$ | Final OD600 ml$^{-1}$ |
|---|---|---|
| T0114 | 0.040 | 0.089 |
| T0117 | 0.033 | 0.055 |
| T0123 | 0.039 | 0.084 |
| T0126 | 0.034 | 0.059 |

This demonstrates that an increase in growth-rate of more than 10% can be achieved when the aldose-1-epimerase is co-expressed together with xylose reductase, xylulose dehydrogenase and D-xylulokinase compared to the isogenic strain not expressing mutarotase. Compare strain T0114 with strain T0117 which does not express the mutarotase and strain T0123 with strain T126 which does not express the mutarotase.

No significant differences between the strains expressing the P. stipitis xylose reductase on either a high copy (strain T0114) or a low copy plasmid (strain T0123) could be measured.

Example 7a

Construction of S. cerevisiae Strains Containing the LpAraA, LpAraB and LpAraD Plasmids Together with, Either the LlMR-36a or the Empty P413-CYC Plasmid (Mumberg et 1995)

200 ng each of the plasmids LpAraA, LpAraB and LpAraD (described in Example 3g, 3h and 3i) are combined with either LlMR-36a (described in Example 3f) or with the empty plasmid P413-CYC (Mumberg et al., 1995) and used for the transformation of S. cerevisiae yeast strain Y07202 (Euroscarf, Germany) by means of electroporation using the Biorad Gene Pulser II system (Biorad, USA) according to the manufacturer's instruction. Yeast cells are made competent according to a standard protocol (Becker, D. M. and Guarente, 1991). Selection for clones transformed with all four plasmids is carried out on solid synthetic complete dropout media omitting uracil, histidine, leucine and tryptophan and supplemented with 2% D-glucose (SC-Ura, His, Leu, Trp) (Rose et al., 1990). Medium-size primary clones are restreaked on SC-Ura, His, Len, Trp and one colony each of the yeast strains carrying either the aldose-1-epimerase (LlMR) gene or the empty vector P413-CYC is isolated.

Example 7b

Measurements of L-Arabinose Metabolism by Growth Curves of the Yeast Strains Described in Example 7a Changes in the rate of L-arabinose metabolism are measured as alterations in the growth rate of the arabinose metabolising yeast strains. The two strains (described in Example 7a) are initially adapted to L-arabinose metabolism. Each strain is inoculated individually in liquid Synthetic Complete dropout media omitting uracil, histidine, leucine and tryptophan supplemented with 2% L-arabinose and 0.2% D-glucose (SCA(+0.2% D-glc)—Ura, His, Leu, Trp). The cultures are incubated for one week at 30° C. in a shaker running at 225 RPM. After one week, each culture is used to re-inoculate new cultures with liquid Synthetic Complete dropout media omitting uracil, histidine, leucine and tryptophan supplemented with 2% L-arabinose and 0.02% D-glucose (SCA(+0.02% D-glc)—Ura, His, Leu, Trp). These cultures are incubated for a further week as described above. Growth experiments are initiated by inoculation of SCA-Ura, His, Leu, Trp supplemented with 2% L-arabinose at an initial cell titre of OD600=0.006/ml. These cultures are incubated as described above. Aliquots are sampled five times with intervals of 24 hours, the optical density, OD600 are measured and growth curves are determined for the two strains. The doubling times are determined, using the time interval of 24-120 hours following the initial lag phase.

An increase in growth-rate and in accumulated yeast biomass is achieved when the aldose-1-epimerase is co-expressed together with L-arabinose isomerase, (LpAraA) L-ribulokinase (LpAraB) and L-ribulose-5-phosphate 4-epimerase (LpAraD) compared to the isogenic strain not expressing a mutarotase.

Example 8a

Construction of a S. cerevisiae Strain Containing the PmXI-8a and the PsXKS-14a Plasmids Together with the Plasmid Encoding ScGAL10 Under Control of the ADH Promoter for Overexpression of Aldose-1-Epimerase 200 ng each of the three plasmids is combined and used for the transformation of S. cerevisiae yeast strain BY4741 (Euroscarf, Germany) by means of electroporation using the Biorad Gene Pulser II system (Biorad, USA) according to the manufacturer's instruction. Yeast cells are made competent according to a standard protocol (Becker and Guarente 1991). Selection for clones transformed with all three plasmids is accomplished on solid synthetic complete dropout media omitting uracil, histidine and leucine and supplemented with 2% D-glucose (SC-Ura, His, Leu) (Rose. et. al. 1990). Clones comprising all three plasmids will grow on SC-Ura, His, Leu.

Example 8b

Construction of a S. cerevisiae Strain Containing the PmXI-8a and the PsXKS-14a Plasmids Together with the Plasmid Encoding ScGAL10Δ Under Control of the ADH Promoter for Overexpression of Aldose-1-Epimerase 200 ng each of the three plasmids is combined and used for the transformation of S. cerevisiae yeast strain BY4741 (Euroscarf, Germany) by means of electroporation using the Biorad Gene Pulser II system (Biorad, USA) according to the manufacturer's instruction. Yeast cells are made competent according to a standard protocol (Becker and Guarente 1991). Selection for clones transformed with all three plasmids is accomplished on solid synthetic complete dropout media omitting uracil, histidine and leucine and supplemented with 2% D-glucose (SC-Ura, His, Leu) (Rose et. al. (1990). Clones comprising all three plasmids will grow on SC-Ura, His, Leu.

Example 8c

Measurements of D-Xylose Metabolism by Growth Curves of the Yeast Strains Described in Example 8a and 8b Changes in the rate of D-xylose metabolism are measured as alterations in the growth rate of the xylose metabolising yeast strains. The two strains are initially adapted to D-xylose metabolism. First, by individual inoculation in liquid Synthetic Complete dropout media omitting uracil, histidine and leucine supplemented with 2% D-xylose and 0.2% D-glucose (SCX(+0.2% D-glc)—Ura, His, Leu) and incubation for one week at 30° C. in a shaker running at 225 RPM. Thereafter, each culture is used for re-inoculation of new cultures in liquid Synthetic Complete dropout media omitting uracil, histidine and leucine supplemented with 2% D-xylose and 0.02% D-glucose (SCX(+0.02% D-glc)—Ura, His, Leu). Again, each culture is incubated for one week at 30° C. in a shaker running at 225 RPM. Growth experiments are initiated by inoculation of SCX-Ura, His, Leu supplemented with 2% D-xylose at an initial cell titre of OD600=0.006/ml. Strain T0067 (transformed with the plasmids P413-CYC, PmXI-8a and POCKS-14a), described in Example 4a, may be included in the experiment, serving as an isogenic control for the measurement of growth without the ScGAL10 or the ScGAL10Δ gene present. Each of the three cultures is incubated as described above and aliquots are sampled four times with intervals of 24 hours. The optical density, OD600 is measured and, based on that, the growth curve for each strain is determined. The doubling time is determined, using the time interval of 24-96 hours following the initial lag phase. The increase in specific growth rate and in accumulated yeast biomass are demonstrated in these two yeast strains, expressing either ScGAL10 or ScGAL10Δ, compared to the isogenic T0067 strain not transformed with a heterologous yeast GAL10 expression derivative (e.g. ScGAL10 or ScGAL10Δ).

Example 9a

TOPO Cloning of a Left Flanking Region for the Stable Integration of Expression Construct into the Yeast Rdn1 Locus ($LFR_{Rdn1}$) Based on NCBI Accession Code DQ130086 Version 1

The S. cerevisiae DNA fragment allowing for the stable integration into the RDN37-2 part of RDN1 ($LFR_{Rdn1}$) was PCR amplified from DNA obtained from the S. cerevisiae strain D0002 using the primers identified by SEQ.ID.NO. 19 and SEQ.ID.NO. 20. A restriction-site for PmeI, proximal to the DNA fragment and a restriction-site for SalI, distal to DNA fragment was introduced flanking the $LFR_{Rdn1}$ piece. As template, DNA from the S. cerevisiae strain was used in a concentration of 0.2 ng/µl PCR-reaction. PCR was performed at 35 cycles of 30 seconds at 96° C., 30 seconds at 57° C., and 20 seconds at 72° C., followed by a final incubation of 10 minutes at 72° C. using Phusion High Fidelity DNA polymerase (Finnzymes Oy, Finland). The PCR product was electrophoretically separated on a 1.0% low melt agarose gel and a 433 bp fragment was isolated. The DNA fragment was TOPO cloned into the pCR-Blunt II-TOPO vector (Invitrogen, USA) according to the manufacturer's instructions and the resulting plasmid was used for the transformation of E. coli TOP10. The plasmid was named Rdn1-L-a15c(+).

Example 9b

TOPO Cloning of a Right Flanking Region for the Stable Integration of Expression Construct into the Yeast Rdn1 Locus ($RFR_{Rdn1}$) Based on NCBI Accession Code DQ130089 Version 1

The S. cerevisiae DNA fragment allowing for the stable integration into the RDN37-2 part of RDN1 ($RFR_{Rdn1}$) was PCR amplified from DNA obtained from the S. cerevisiae strain D0002 using the primers identified by SEQ.ID.NO. 21 and SEQ.ID.NO. 22. A restriction-site for XhoI, proximal to the DNA fragment and a restriction-site for PmeI, distal to DNA fragment was introduced flanking the $RFR_{Rdn1}$ piece. As template, DNA from the S. cerevisiae strain was used in a concentration of 0.2 ng/µl PCR-reaction. PCR was performed at 35 cycles of 30 seconds at 96° C., 30 seconds at 57° C., and 20 seconds at 72° C., followed by a final incubation of 10 minutes at 72° C. using Phusion High Fidelity DNA polymerase (Finnzymes Oy, Finland). The PCR product was electrophoretically separated on a 1.0% low melt agarose gel and a 503 bp fragment was isolated. The DNA fragment was TOPO cloned into the pCR-Blunt II-TOPO vector (Invitrogen, USA) according to the manufacturer's instructions and the resulting plasmid was used for the transformation of E. coli TOP10. The plasmid was named Rdn1-R-a16b(+).

Example 9c

TOPO Cloning of a Left Flanking Region for the Stable Integration of Expression Construct into the Yeast Mig1 Locus (LFR$_{Mig1-2}$) Based on NCBI Accession Code Z72557 Version 1

The *S. cerevisiae* DNA fragment allowing for the stable integration into the MIG1 locus (LFR$_{Mig1-2}$) was PCR amplified from DNA obtained from the *S. cerevisiae* strain D0002 using the primers identified by SEQ.ID.NO. 23 and SEQ.ID.NO. 24. A restriction-site for PmeI, proximal to the DNA fragment and a restriction-site for SalI, distal to DNA fragment was introduced flanking the LFR$_{Mig1-2}$ piece. As template, DNA from the *S. cerevisiae* strain was used in a concentration of 0.2 ng/μl PCR-reaction. PCR was performed at 35 cycles of 30 seconds at 96° C., 30 seconds at 57° C., and 20 seconds at 72° C., followed by a final incubation of 10 minutes at 72° C. using Phusion High Fidelity DNA polymerase (Finnzymes Oy, Finland). The PCR product was electrophoretically separated on a 1.0% low melt agarose gel and a 507 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named Mig1-L2-a19h(+).

Example 9d

TOPO Cloning of a Right Flanking Region for the Stable Integration of Expression Construct into the Yeast MIG1 Locus (RFR$_{Mig1-2}$) Based on NCBI Accession Code Z72556 Version 1

The *S. cerevisiae* DNA fragment allowing for the stable integration into the MIG1 locus (RFR$_{Mig1-2}$) was PCR amplified from DNA obtained from the *S. cerevisiae* strain D0002 using the primers identified by SEQ.ID.NO. 25 and SEQ.ID.NO. 26. A restriction-site for XhoI, proximal to the DNA fragment and a restriction-site for PmeI, distal to DNA fragment was introduced flanking the RFR$_{Mig1-2}$ piece. As template, DNA from the *S. cerevisiae* strain was used in a concentration of 0.2 ng/μl PCR-reaction. PCR was performed at 35 cycles of 30 seconds at 96° C., 30 seconds at 57° C., and 20 seconds at 72° C., followed by a final incubation of 10 minutes at 72° C. using Phusion High Fidelity DNA polymerase (Finnzymes Oy, Finland). The PCR product was electrophoretically separated on a 1.0% low melt agarose gel and a 500 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named Mig1-R2-a20a(−).

Example 10a

Construction of a Yeast Integrative Plasmid Containing the *S. cerevisiae* Left and Right Flanking Regions of the Rdn1 Locus (LFR$_{Rdn1}$+RFR$_{Rdn1}$) Allowing for Homologous Recombination into the Yeast Genome The plasmid Rdn1-L-a15c(+) (described in Example 9a) was digested with XhoI and PsmOMI and resulting termini subsequently dephosphorylated with alkaline phosphatase. Similarly, the plasmid Rdn1-R-a16b(+) (described in Example 9b) was digested with XhoI and NotI. The resulting linearized plasmid Rdn1-L-a15c(+) and the DNA fragment containing RFR$_{Rdn1}$ originating from the plasmid Rdn1-R-a16b(+) was electrophoretically separated on a 0.7% low melt agarose gel and thereafter isolated. The linearized plasmid Rdn1-L-a15c(+) was ligated together with the RFR$_{Rdn1}$ DNA fragment and the resulting plasmid was used for the transformation of *E. coli* TOP10. The plasmid was named Rdn1-LR-b5a.

Example 10b

Construction of a Yeast Integrative Plasmid Containing the *S. cerevisiae* Left And Right Flanking Regions of the MIG1 Locus (LFR$_{Mig1-2}$+ RFR$_{Mig1-2}$) Allowing for Homologous Recombination into the Yeast Genome The plasmid Mig1-L2-a19h(+) (described in Example 9c) was digested with NotI and XbaI and resulting termini subsequently dephosphorylated with alkaline phosphatase. Similarly, the plasmid Mig1-R2-a20a(−) (described in Example 9d) was digested with SpeI and NotI. The resulting linearized plasmid Mig1-L2-a19h(+) and the DNA fragment containing RFR$_{Mig1-2}$ originating from the plasmid Mig1-R2-a20a(−) was electrophoretically separated on a 0.7% low melt agarose gel and thereafter isolated. The linearized plasmid Mig1-L2-a19h(+) was ligated together with the RFR$_{Mig1-2}$ DNA fragment and the resulting plasmid was used for the transformation of *E. coli* TOP10. The plasmid was named Mig1-LR2-b7a.

Example 11

Construction of loxP Flanked Antibiotic Marker Gene Cassettes with Either the kanMX or the nal Gene The plasmid pUG6 (Güldener et al, 1996) was digested with Xba and XhoI and resulting termini subsequently dephosphorylated with alkaline phosphatase. Similarly, the plasmids pAG25 (Goldstein and McCusker, 1999) and pUG6 was digested with SpeI and SalI, The resulting linearized plasmid pUG6 and the DNA fragments containing the nail gene (originating from the plasmid pAG25) and the kanMX gene (originating from the plasmid pUG6) were electrophoretically separated on a 0.7% low melt agarose gel and thereafter isolated. The linearized plasmid pUG6 was ligated together with the nat1 encoding DNA fragment and the resulting plasmid was used for the transformation of *E. coli* TOP10. This plasmid was named pUG6R25-b2a. Similarly, the linearized plasmid pUG6 was ligated together with the kanMX encoding DNA fragment and the resulting plasmid was used for the transformation of *E. coli* TOP 10. This plasmid was named pUG6R6-b1a.

Example 12a

Construction of a Yeast Integrative Plasmid Containing the *S. cerevisiae* Left Flanking Region of the Rdn1 Locus (LFR$_{Rdn1}$), the loxP Flanked Antibiotic Marker Gene na1 and the Right Flanking Region of the Rdn1 Locus (RFR$_{Rdn1}$) Allowing for Homologous Recombination into the Yeast Genome and Subsequent Selection Using the Antibiotic Nourseothricin The plasmid Rdn1-LR-b5a (described in Example 10a) is digested with NotI and resulting termini subsequently dephosphorylated with alkaline phosphatase. Similarly, the plasmid pUG6R25-b2a (described in Example 11) is digested with NotI. The resulting linearized plasmid Rdn1-LR-b5a and the DNA fragment containing the loxP flanked nail gene (originating from the plasmid pUG6R25-b2a) are electrophoretically separated on a 0.7% low melt agarose gel and thereafter isolated. The linearized plasmid Rdn1-LR-b5a is ligated together with the loxP flanked nat1 gene DNA fragment and the resulting plasmid is used for the transformation of *E. coli* TOP 10.

Example 12b

Construction of a Yeast Integrative Plasmid Containing the *S. cerevisiae* Left Flanking Region of the Mig1 Locus (LFR$_{Mig1-2}$), the loxP Flanked Antibiotic Marker Gene kanMX and the Right Flanking Region of the Mig1 Locus (RFR$_{Mig1-2}$) Allowing for Homologous Recombination into the Yeast Genome and Subsequent Selection Using the Antibiotic G418

The plasmid Mig1-LR2-b7a (described in Example 10b) is digested with NotI and resulting termini subsequently dephosphorylated with alkaline phosphatase. Similarly, the plasmid pUG6R6-b1a (described in Example 11) is digested with NotI. The resulting linearized plasmid Mig1-LR2-b7a and the DNA fragment containing the loxP flanked kanMX gene (originating from the plasmid pUG6R6-b1a) are electrophoretically separated on a 0.7% low melt agarose gel and thereafter isolated. The linearized plasmid Mig1-LR2-b7a is ligated together with the loxP flanked kanMX gene DNA fragment and the resulting plasmid is used for the transformation of *E. coli* TOP10.

Example 13a

TOPO Cloning of a DNA Fragment Containing the Transcription Terminator of the Open Reading Frame YBR197C and the Promoter of the Gene PGI1 Based on NCBI Accession Code Z21487 Version 1

The *S. cerevisiae* DNA fragment (P-pgi) covering the region between the stop codon of the open reading frame YBR197C and ATG codon of the gene PGI1 was PCR amplified from DNA obtained from the *S. cerevisiae* strain D0002 using the primers identified by SEQ.ID.NO. 27 and SEQ.ID.NO. 28. A restriction-site for SalI, proximal to the DNA fragment and a restriction-site for AvrII, distal to DNA fragment was introduced flanking the intergenic region. As template, DNA from the *S. cerevisiae* strain was used in a concentration of 0.2 ng/µl PCR-reaction. PCR was performed at 35 cycles of 30 seconds at 96° C., 30 seconds at 57° C., and 30 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 1318 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named P-pgi-a1a(+).

Example 13b

TOPO Cloning of a DNA Fragment Containing the Transcription Terminator of the Open Reading Frame YDR051C and the Promoter of the Gene TPI1 Based on NCBI Accession Code 249209 Version 1

The *S. cerevisiae* DNA fragment (P-tpi) covering the region between the stop codon of the open reading frame YDR051C and ATG codon of the gene TPI1 was PCR amplified from DNA obtained from the *S. cerevisiae* strain D0002 using the primers identified by SEQ.ID.NO. 29 and SEQ.ID.NO. 30. A restriction-site for SalI, proximal to the DNA fragment and a restriction-site for AvrII, distal to DNA fragment was introduced flanking the intergenic region. As template, DNA from the *S. cerevisiae* strain was used in a concentration of 0.2 ng/0 PCR-reaction. PCR was performed at 35 cycles of 30 seconds at 96° C., 30 seconds at 57° C., and 30 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 599 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named P-tpi-a2d(+).

Example 13c

TOPO Cloning of a DNA Fragment Containing the Transcription Terminator of the Gene YKU80 and the Promoter of the Gene PGM2 Based on NCBI Accession Code Z49702 Version 1

The *S. cerevisiae* DNA fragment (P-pgm) covering the region between the stop codon of gene YKU80 and ATG codon of the gene PGM2 was PCR amplified from DNA obtained from the *S. cerevisiae* strain D0002 using the primers identified by SEQ.ID.NO. 31 and SEQ.ID.NO. 32. A restriction-site for SalI, proximal to the DNA fragment and a restriction-site for AvrII, distal to DNA fragment was introduced flanking the intergenic region. As template, DNA from the *S. cerevisiae* strain was used in a concentration of 0.2 ng/µl PCR-reaction. PCR was performed at 35 cycles of 30 seconds at 96° C., 30 seconds at 57° C., and 30 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 710 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named P-pgm-a10a(+).

Example 13d

TOPO Cloning of a DNA Fragment Containing the Transcription Terminator of the Gene STU2 and the Promoter of the Gene PDC1 Based on NCBI Accession Code 173217 Version 1

The *S. cerevisiae* DNA fragment (P-pdc) covering the region between the stop codon of gene STU2 and ATG codon of the gene PDC1 was PCR amplified from DNA obtained from the *S. cerevisiae* strain D0002 using the primers identified by SEQ.ID.NO. 33 and SEQ.ID.NO. 34. A restriction-site for SalI, proximal to the DNA fragment and a restriction-site for AvrII, distal to DNA fragment was introduced flanking the intergenic region. As template, DNA from the *S. cerevisiae* strain was used in a concentration of 0.2 ng/µl PCR-reaction. PCR was performed at 35 cycles of 30 seconds at 96° C., 30 seconds at 57° C., and 30 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 971 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named P-pdc-a9f(+).

Example 13e

TOPO Cloning of a DNA Fragment Containing the Transcription Terminator of the Gene MPE1 and the Promoter of the Gene FBA1 Based on NCBI Accession Code Z28060 Version 1

The *S. cerevisiae* DNA fragment (P-fba) covering the region between the stop codon of gene MPE1 and ATG codon of the gene FBA1 was PCR amplified from DNA obtained from the *S. cerevisiae* strain D0002 using the primers identified by SEQ.ID.NO. 35 and SEQ.ID.NO. 36. A restriction-site for SalI, proximal to the DNA fragment and a restriction-site for AvrII, distal to DNA fragment was introduced flanking the intergenic region. As template, DNA from the *S. cerevisiae* strain was used in a concentration of 0.2 ng/µl PCR-reaction. PCR was performed at 35 cycles of 30 seconds at 96° C., 30 seconds at 57° C., and 30 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 646 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named P-fba-a7b(+).

Example 13l

TOPO Cloning of a DNA Fragment Containing the Transcription Terminator of the Open Reading Frame YKL151C and the Promoter of the Gene GPM1 Based on NCBI Accession Code Z26877 Version 1

The *S. cerevisiae* DNA fragment (P-gpm) covering the region between the stop codon of the open reading frame YKL151C and ATG codon of the gene GPM1 was PCR amplified from DNA obtained from the *S. cerevisiae* strain D0002 using the primers identified by SEQ.ID.NO. 37 and SEQ.ID.NO. 38. A restriction-site for SalI, proximal to the DNA fragment and a restriction-site for AvrII, distal to DNA fragment was introduced flanking the intergenic region. As template, DNA from the *S. cerevisiae* strain was used in a concentration of 0.2 ng/µl PCR-reaction. PCR was performed at 35 cycles of 30 seconds at 96° C., 30 seconds at 57° C., and 30 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 547 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named P-gpm-a8a(+).

Example 14a

TOPO Cloning of the TKL1 Gene from the *Saccharomyces cerevisiae* Strain D0002 based on NCBI Accession Code X73224 Version 1

The entire *S. cerevisiae* TKL1 gene (ScTKL1) was PCR amplified from DNA obtained from the *S. cerevisiae* strain D0002 using the primers identified by SEQ.ID.NO. 39 and SEQ.ID.NO. 40. A restriction-site for XbaI, proximal to the ATG-start codon and a restriction-site for XhoI, distal to the stop-codon was introduced flanking the ScTKL1 gene. As template, DNA from the *S. cerevisiae* strain was used in a concentration of 0.2 ng/µl PCR-reaction. PCR was performed at 35 cycles of 30 seconds at 96° C., 30 seconds at 57° C., and 90 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 2059 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named ScTKL1-a25a(+).

Example 14b

TOPO Cloning of the XKS1 Gene from the *Saccharomyces cerevisiae* Strain D0002 Based on NCBI Accession Code X61377 Version 1

The entire *S. cerevisiae* XKS1 gene (ScXKS1) was PCR amplified from DNA obtained from the *S. cerevisiae* strain D0002 using the primers identified by SEQ.ID.NO. 41 and SEQ.ID.NO. 42. A restriction-site for NheI, proximal to the ATG-start codon and a restriction-site for XhoI, distal to the stop-codon was introduced flanking the ScXKS1 gene. As template, DNA from the *S. cerevisiae* strain was used in a concentration of 0.2 ng/µl PCR-reaction. PCR was performed at 35 cycles of 30 seconds at 96° C., 30 seconds at 57° C., and 90 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 2059 bp fragment was isolated. The DNA fragment was TOPO cloned into the pCR-Blunt II-TOPO vector (Invitrogen, USA) according to the manufacturer's instructions and the resulting plasmid was used for the transformation of *E. coli*TOP10. The plasmid was named ScXKS1-G2.

Example 14c

TOPO Cloning of the TAL1 Gene Including 187 bp of Transcription Terminator from the *Saccharomyces cerevisiae* Strain D0002 Based on NCBI Accession Code X15953 Version 1

The entire *S. cerevisiae* TAL1 gene together with 187 bp of transcription terminator sequence (ScTAL1+T) was PCR amplified from DNA obtained from the *S. cerevisiae* strain D0002 using the primers identified by SEQ.ID.NO. 43 and SEQ.ID.NO. 44. A restriction-site for NheI, proximal to the ATG-start codon and a restriction-site for XhoI, distal to the transcription terminator sequence was introduced flanking the ScXKS1+T gene. As template, DNA from the *S. cerevisiae* strain was used in a concentration of 0.2 ng/µl PCR-reaction. PCR was performed at 35 cycles of 30 seconds at 96° C., 30 seconds at 57° C., and 60 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 1210 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named ScTAL1+T-a22a(+).

Example 14d

TOPO Cloning of the RKI1 Gene Including 206 Bp of Transcription Terminator from the *Saccharomyces cerevisiae* Strain D0002 Based on NCBI Accession Code X94335 Version 1

The entire *S. cerevisiae* RKI1 gene together with 206 bp of transcription terminator sequence (ScRKI1+T) was PCR amplified from DNA obtained from the *S. cerevisiae* strain D0002 using the primers identified by SEQ.ID.NO. 45 and SEQ.ID.NO. 46. A restriction-site for NheI, proximal to the ATG-start codon and a restriction-site for XhoI, distal to the transcription terminator sequence was introduced flanking the ScRKI1+T gene. As template, DNA from the *S. cerevisiae* strain was used in a concentration of 0.2 ng/µl PCR-reaction. PCR was performed at 35 cycles of 30 seconds at 96° C., 30 seconds at 57° C., and 60 seconds at 72° C., followed by a final incubation of 10 minutes at 72° C. using Phusion High Fidelity DNA polymerase (Finnzymes Oy, Finland). The PCR product was electrophoretically separated on a 0.7% low melt agarose gel and a 998 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named ScRKI1+T-a21c(+).

Example 15a

Construction of a Plasmid Containing the Yeast Expression Cassette Composed of the P-pgi Promoter in Front of the ScXKS1 Gene The plasmid P-pgi-a1a(+) (described in Example 13a) was digested with AvrII and XhoI and resulting termini subsequently dephosphorylated with alkaline phosphatase. Similarly, the plasmid ScXKS1-02 (described in Example 1413) was digested with NheI and XhoI. The resulting linearized plasmid P-pgi-a1a(+) and the DNA fragment containing ScXKS1 originating from the plasmid ScXKS1-G2 were electrophoretically separated on a 0.7% low melt agarose gel and thereafter isolated. The linearized plasmid P-pgi-a1a(+) was ligated together with the ScXKS 1 encoding DNA fragment and the resulting plasmid was used for the transformation of *E. coli TOP* 10. The plasmid was named P-pgi+ScXKS1-b38a.

Example 15b

Construction of a Plasmid Containing the Yeast Expression Cassette Composed of the P-Fba Promoter in Front of the PmXI Gene The plasmid P-fba-a7b(+) (described in Example 13e) was digested with AvrII and XhoI and resulting termini subsequently dephosphorylated with alkaline phosphatase. Similarly, the plasmid 0717049pGA15 carrying the PmXI gene (described in Example 1b) was digested with NheI and XhoI. The resulting linearized plasmid P-fba-a7b(+) and the DNA fragment containing PmXI originating from the plasmid 0717049pGA15 were electrophoretically separated on a 0.7% low melt agarose gel and thereafter isolated. The linearized plasmid P-fba-a7b(+) was ligated together with the PmXI encoding DNA fragment and the resulting plasmid was used for the transformation of *E. coli*TOP 10. The plasmid was named P-fba+PmXI-b34c.

Example 15c

Construction of a Plasmid Containing the Yeast Expression Cassette Composed of the P-gpm Promoter in Front of the ScRKI1+T Gene The plasmid P-gpm-a8a(+) (described in Example 13f) was digested with AvrII and XhoI and resulting termini subsequently dephosphorylated with alkaline phosphatase. Similarly, the plasmid ScRKI1+T-a21c(+) (described in Example 13d) was digested with NheI and XhoI. The resulting linearized plasmid P-gpm-a8a(+) and the DNA fragment containing ScRKI1+T originating from the plasmid ScRKI1+T-a21c(+) were electrophoretically separated on a 0.7% low melt agarose gel and thereafter isolated. The linearized plasmid P-gpm-a8a(+) was ligated together with the ScRKI1+T encoding DNA fragment and the resulting plasmid was used for the transformation of *E. coli* TOP10. The plasmid was named P-gpm+ScRKI1+T-b15a.

Example 15d

Construction of a Plasmid Containing the Yeast Expression Cassette Composed of the P-tpi Promoter in Front of the L1MR Gene The plasmid P-tpi-a2d(+) (described in Example 13b) was digested with AvrII and XhoI and resulting termini subsequently dephosphorylated with alkaline phosphatase. Similarly, the plasmid 0717050pGA14 (described in Example 1a) was digested with NheI and XhoI. The resulting linearized plasmid P-tpi-a2d(+) and the DNA fragment containing L1MR originating from the plasmid 0717050pGA14 were electrophoretically separated on a 0.7% low melt agarose gel and thereafter isolated. The linearized plasmid P-tpi-a2d(+) was ligated together with the L1MR encoding DNA fragment and the resulting plasmid was used for the transformation of *E. coli* TOP 10. The plasmid was named P-tpi+L1MR-b39a.

Example 15e

Construction of a Plasmid Containing the Yeast Expression Cassette Composed of the P-pgm Promoter in Front of the ScTKL1 Gene The plasmid P-pgm-a10a(+) (described in Example 13c) was digested with AvrII and XhoI and resulting termini subsequently dephosphorylated with alkaline phosphatase. Similarly, the plasmid ScTKL1-a25a(+) (described in Example 14a) was digested with XbaI and XhoI. The resulting linearized plasmid P-pgm-a10a(+) and the DNA fragment containing ScTKL1 originating from the plasmid ScTKL1-a25a(+) were electrophoretically separated on a 0.7% low melt agarose gel and thereafter isolated. The linearized plasmid P-pgm-a10a(+) was ligated together with the ScTKL1 encoding DNA fragment and the resulting plasmid was used for the transformation of *E. coli* TOP10. The plasmid was named P-pgm+ScTKL1-b67a.

Example 15f

Construction of a Plasmid Containing the Yeast Expression Cassette Composed of the P-pdc Promoter in Front of the TAL1+T Gene The plasmid P-pdc-a9f(+) (described in Example 13d) was digested with AvrII and XhoI and resulting termini subsequently dephosphorylated with alkaline phosphatase. Similarly, the plasmid ScTAL1+T-a22a(+) (described in Example 14c) was digested with NheI and XhoI. The resulting linearized plasmid P-pdc-a9f(+) and the DNA fragment containing ScTAL1+T originating from the plasmid ScTAL1+T-a22a(+) were electrophoretically separated on a 0.7% low melt agarose gel and thereafter isolated. The linearized plasmid P-pdc-a9f(+) was ligated together with the ScTAL1+T encoding DNA fragment and the resulting plasmid was used for the transformation of *E. coli* TOP10. The plasmid was named P-pdc+ScTAL1+T-b26a.

Example 16a

Construction of a Plasmid with the P-pgi+ScXKS and the P-fba+PmXI Concatenated Yeast Expression Cassettes The plasmid pgi+ScXKS1-b38a (described in Example 15a) is digested with XhoI and ApaI and resulting termini subsequently dephosphorylated with alkaline phosphatase. Similarly, the plasmid P-fba+PmXI-b34c (described in Example 15b) is digested with SalI and ApaI. The resulting linearized plasmid pgi+ScXKS1-b38a and the DNA fragment containing the P-fba+PmXI expression cassette originating from the plasmid P-fba+PmXI-b34c are electrophoretically separated on a 0.7% low melt agarose gel and thereafter isolated. The linearized plasmid pgi+ScXKS1-b38a is ligated together with the DNA fragment containing the P-fba+PmXI expression cassette and the resulting plasmid is used for the transformation of *E. coli* TOP10.

Example 16b

Construction of a Plasmid with the P-tpi+L1MR and the P-pgm+ScTKL1 Concatenated Yeast Expression Cassettes The plasmid P-tpi+L1MR-b39a (described in Example 15d) is digested with XhoI and ApaI and resulting termini subsequently dephosphorylated with alkaline phosphatase. Similarly, the plasmid P-pgm+ScTKL1-b67a (described in Example 15e) is digested with SalI and ApaI. The resulting linearized plasmid P-tpi+L1MR-b39a and the DNA fragment containing the P-pgm+ScTKL1 expression cassette originating from the plasmid P-pgm+ScTKL1-b67a are electrophoretically separated on a 0.7% low melt agarose gel and thereafter isolated. The linearized plasmid P-tpi+L1MR-b39a is ligated together with the DNA fragment containing the P-pgm+ScTKL1 expression cassette and the resulting plasmid is used for the transformation of *E. coli* TOP 10.

Example 17a

Construction of a Plasmid with the P-pgi+ScXKS, the P-fba+PmXI and the P-gpm+ScRKI1+T Concatenated Yeast Expression Cassettes The plasmid containing the concatenated P-pgi+ScXKS and P-fba+PmXI yeast expression cassettes (described in Example 16a) is digested with XhoI and ApaI and resulting termini subsequently dephosphorylated with alkaline phosphatase. Similarly, the plasmid P-gpm+ScRKI1+T-b15a (described in Example 15e) is digested with. SalI and ApaI. The resulting linearized plasmid, containing the concatenated P-pgi+ScXKS and P-fba+PmXI yeast expression cassettes, and the DNA fragment containing the P-gpm+ScRKI1+T expression cassette originating from the plasmid P-gpm+ScRKI1+T-b15a are electrophoretically separated on a 0.7% low melt agarose gel and thereafter isolated. The linearized plasmid, containing the concatenated P-pgi+ScXKS and P-fba+PmXI yeast expression cassettes, is ligated together with the DNA fragment containing the P-gpm+ScRKI1+T expression cassette and the resulting plasmid is used for the transformation of *E. coli* TOP10.

Example 17b

Construction of a Plasmid with the P-tpi+L1MR, the P-pgm+ScTKL1 and the P-pdc+ScTAL1+T Concatenated Yeast Expression Cassettes The plasmid containing the concatenated P-tpi+L1MR and P-pgm+ScTKL1 yeast expression cassettes (described in Example 16b) is digested with XhoI and ApaI and resulting termini subsequently dephosphorylated with alkaline phosphatase. Similarly, the plasmid P-pdc+ScTAL1+T-b26a (described in Example 15l) is digested with SalI and ApaI. The resulting linearized plasmid, containing the concatenated P-tpi+L1MR and P-pgm+ScTKL1 yeast expression cassettes, and the DNA fragment containing the P-pdc+ScTAL1+T expression cassette originating from the plasmid P-pdc+ScTAL1+T-b26a are electrophoretically separated on a 0.7% low melt agarose gel and thereafter isolated. The linearized plasmid, containing the concatenated P-tpi+L1MR and P-pgm+ScTKL1 yeast expression cassettes, is ligated together with the DNA fragment containing the P-pdc+ScTAL1+T expression cassette and the resulting plasmid is used for the transformation of *E. coli* TOP 10.

Example 17c

Construction of a Plasmid with the P-pgm+ScTKL1 and the P-pdc+ScTAL1+T Concatenated Yeast Expression Cassettes The plasmid P-pgm+ScTKL1-b67a (described in Example 15e) is digested with XhoI and ApaI and resulting termini subsequently dephosphorylated with alkaline phosphatase. Similarly, the plasmid P-pdc+ScTAL1+T-b26a (described in Example 15O) is digested with SalI and ApaI. The resulting linearized plasmid, P-pgm+ScTKL1-b67a, and the DNA fragment containing the P-pdc+ScTAL1+T expression cassette originating from the plasmid P-pdc+ScTAL1+T-b26a are electrophoretically separated on a 0.7% low melt agarose gel and thereafter isolated. The linearized plasmid, P-pgm+ScTKL1-b67a is ligated together with the DNA fragment containing the P-pdc+ScTAL1+T expression cassette and the resulting plasmid is used for the transformation of *E. coli* TOP 10.

Example 18a

Construction of a Yeast Integrative Plasmid Harbouring the P-Pgi+ScXKS, the P-fba+PmXI and the P-gpm+ScRKI1+T Concatenated Yeast Expression Cassettes Allowing for Homologous Recombination into the Rdn1 Locus and Subsequent Selection Using the Antibiotic Nourseothricin The yeast integrative plasmid allowing for homologous recombination into the Rdn1 locus and subsequent selection on growth media supplemented with nourseothricin (described in Example 12a) is digested with XhoI and resulting termini subsequently dephosphorylated with alkaline phosphatase. Linearized plasmid is electrophoretically separated on a 0.7% low melt agarose gel, from that of uncut plasmid, and thereafter isolated. Likewise, the plasmid carrying the concatenated P-pgi+ScXKS, P-fba+PmXI and P-gpm+ScRKI1+T yeast expression cassettes (described in Example 17a) is digested with XhoI and SalI. The concatenated P-pgi+ScXKS, P-fba+fba+PmXI and P-gpm+ScRKI1+T yeast expression cassette fragment is electrophoretically separated from the vector backbone, using a 0.7% low melt agarose gel, and thereafter isolated. The linearized integrative plasmid is ligated together with the concatenated P-pgi+ScXKS, P-fba+PmXI and P-gpm+ScRKI1+T yeast expression cassette fragment and the resulting plasmid is used for the transformation of *E. coli* TOP 10.

Example 18b

Construction of a Yeast Integrative Plasmid Harbouring the P-tpi+LlMR, the P-pgm+ScTKL1 and the P-pdc+ScTAL1+T Concatenated Yeast Expression Cassettes Allowing for Homologous Recombination into the Mig1 Locus and Subsequent Selection Using the Antibiotic G418

The yeast integrative plasmid allowing for homologous recombination into the Mig1 locus and subsequent selection on growth media supplemented with G418 (described in Example 12b) is digested with XhoI and resulting termini subsequently dephosphorylated with alkaline phosphatase. Linearized plasmid is electrophoretically separated on a 0.7% low melt agarose gel, from that of uncut plasmid, and thereafter isolated. Likewise, the P-tpi+LlMR, the P-pgm+ScTKL1 and the P-pdc+ScTAL1+T concatenated yeast expression cassettes (described in Example 17b) is digested with XhoI and SalI. The concatenated P-tpi+LlMR, 1'-pgm+ScTKL1 and P-pdc+ScTAL1+T yeast expression cassette fragment is electrophoretically separated from the vector backbone, using a 0.7% low melt agarose gel, and thereafter isolated. The linearized integrative plasmid is ligated together with the concatenated P-tpi+LlMR, P-pgm+ScTKL1 and P-pdc+ScTAL1+T yeast expression cassette fragment and the resulting plasmid is used for the transformation of *E. coli* TOP10.

Example 18c

Construction of a Yeast Integrative Plasmid Harbouring the P-Pgm+ScTKL1 and the P-pdc+ScTAL1+T Concatenated Yeast Expression Cassettes Allowing for Homologous Recombination into the Mig1 Locus and Subsequent Selection Using the Antibiotic G418

The yeast integrative plasmid allowing for homologous recombination into the Mig1 locus and subsequent selection on growth media supplemented with G418 (described in Example 12b) is digested with XhoI and resulting termini subsequently dephosphorylated with alkaline phosphatase. Linearized plasmid is electrophoretically separated on a 0.7% low melt agarose gel, from that of uncut plasmid, and thereafter isolated. Likewise, the P-pgm+ScTKL1 and the P-pdc+ScTAL1+T concatenated yeast expression cassettes (described in Example 17c) is digested with XhoI and SalI. The concatenated P-pgm+ScTKL1 and P-pdc+ScTAL1+T yeast expression cassette fragment is electrophoretically separated from the vector backbone, using a 0.7% low melt agarose gel, and thereafter isolated. The linearized integrative plasmid is ligated together with the concatenated P-pgm+ScTKL1 and P-pdc+ScTAL1+T yeast expression cassette fragment and the resulting plasmid is used for the transformation of *E. coli* TOP10.

Example 19

Construction of a *S. cerevisiae* Strain Containing the P-Pgi+ScXKS, the P-Fba+PmXI and the P-gpm+ScRKI1+T Concatenated Yeast Expression Cassettes by Recombination into the Rdn1 Locus and Subsequent Selection Using the Antibiotic Nourseothricin Five µg of the integrative plasmid harbouring the P-pgi+ScXKS, the P-fba+PmXI and the P-gpm+ScRKI1+T concatenated yeast expression cassettes (described in Example 18a) is digested with PmeI and subsequently precipitated using 2.5 volumes of 96% ethanol. After discarding the liquid, the DNA pellet is washed with 70% ethanol, dried and redissolved with 5 µl water. The redissolved digested plasmid is used for the transformation of *S. cerevisiae* yeast strain BY4741 (Euroscarf, Germany) by means of electroporation using the Biorad Gene Pulser II system (Biorad, USA) according to the manufacturer's instruction. Yeast cells are made competent according to a standard protocol (Becker and Guarente 1991). Selection for clones stably transformed with the P-pgi+ScXKS, the P-fba+PmXI and the P-gpm+ScRKI1+T concatenated yeast expression cassettes, are performed by plating on YPD solid growth medium supplemented with 100 mg/L of ClonNAT (Werner BioAgents, Jena, Germany). Prior to plating, the transformed cells are allowed to grow in liquid YPD at 30° C. for 4 hours. After plating on selective media, the plates are incubated at 30° C. for 3 days, a medium size colony is isolated and restreaked on solid YPD supplemented 100 mg/L of ClonNAT and a clone is subsequently isolated.

Example 20a

Construction of a P-pgi+ScXKS, P-fba+PmXI and P-gpm+ScRKI1+T Concatenated Expression Cassette Containing *S. cerevisiae* Strain Including the P-Tpi+LlMR, the P-pgm+ScTKL1 and the P-pdc+ScTAL1+T Concatenated Yeast Expression Cassettes by Recombination into the Mig1 Locus and Subsequent Selection Using the Antibiotic G418

Five μg of the integrative plasmid harbouring the P-tpi+LlMR, the P-pgm+ScTKL1 and the P-pdc+ScTAL1+T concatenated yeast expression cassettes (described in Example 18b) is digested with PmeI and subsequently precipitated using 2.5 volumes of 96% ethanol. After discarding the liquid, the DNA pellet is washed with 70% ethanol, dried and redissolved with 5 μl water. The redissolved digested plasmid is used for the transformation of the *S. cerevisiae* yeast strain described in Example 19 by means of electroporation using the Biorad Gene Pulser II system (Biorad, USA) according to the manufacturer's instruction. Yeast cells are made competent according to a standard protocol (Becker and Guarente 1991). Selection for clones stably transformed with the P-tpi+LlMR, the P-pgm+ScTKL1 and the P-pdc+ScTAL1+T concatenated yeast expression cassettes, are performed by plating on YPD solid growth medium supplemented with 200 mg/L of geneticin (Life Technologies). Prior to plating, the transformed cells are allowed to grow in liquid YPD at 30° C. for 4 hours. After plating on selective media, the plates are incubated at 30° C. for 3 days, a medium size colony is isolated and restreaked on solid YPD supplemented 200 mg/L of geneticin and a clone is subsequently isolated.

Example 20b

Construction of a P-pgi+ScXKS, P-fba+PmXI and P-gpm+ScRKI1+T Concatenated Expression Cassette Containing *S. cerevisiae* Strain Including the P-pgm+ScTKL1 and the P-pdc+ScTAL1+T Concatenated Yeast Expression Cassettes by Recombination into the Mig1 Locus and Subsequent Selection Using the Antibiotic G418

Five μg of the integrative plasmid harbouring the P-pgm+ScTKL1 and the P-pdc+ScTAL1+T concatenated yeast expression cassettes (described in Example 18c) is digested with PmeI and subsequently precipitated using 2.5 volumes of 96% ethanol. After discarding the liquid, the DNA pellet is washed with 70% ethanol, dried and redissolved with 5 μl water. The redissolved digested plasmid is used for the transformation of the *S. cerevisiae* yeast strain described in Example 19 by means of electroporation using the Biorad Gene Pulser II system (Biorad, USA) according to the manufacturer's instruction. Yeast cells are made competent according to a standard protocol (Becker and Guarente 1991). Selection for clones stably transformed with the P-pgm+ScTKL1 and the P-pdc+ScTAL1+T concatenated yeast expression cassettes, is performed by plating on YPD solid growth medium supplemented with 200 mg/L of geneticin (Life Technologies). Prior to plating, the transformed cells are allowed to grow in liquid YPD at 30° C. for 4 hours. After plating on selective media, the plates are incubated at 30° C. for 3 days, a medium size colony is isolated and restreaked on solid YPD supplemented 200 mg/L of geneticin and a clone is subsequently isolated.

Example 21a

Measurements of D-Xylose Metabolism by Growth Curves of the Yeast Strains Described in Example 20a and 20b Changes in the rate of D-xylose metabolism are measured as alterations in the growth rate of the xylose metabolising yeast strains. The two yeast strains (described in Example 20a and 20b) are initially adapted to D-xylose metabolism. Each strain is inoculated individually in liquid Yeast Peptone Xylose (YPX) supplemented with 0.2% glucose. The cultures are incubated for one week at 30° C. in a shaker running at 225 RPM. After one week, each culture is used to re-inoculate new cultures with YPX supplemented with 0.02% glucose. The two cultures are incubated for a further week as described above. Growth experiments are initiated by inoculation of YPX at an initial cell titre of OD600=0.006/ml. The cultures are incubated as described above. Aliquots are sampled five times with intervals of 24 hours, the optical density, OD600 is measured and growth curves are determined for the two strains. The doubling times are determined, using the time interval of 24-120 hours following the initial lag phase. An increased growth rate of the strain expressing the aldose-1-epimerase (LlMR) together with the xylose isomerase (PmXI), the D-xylulokinase (SOCKS), the ribose-5-phosphate ketol-isomerase (ScRKI1+T), the transketolase (ScTKL1) and the transaldolase (ScTAL1+T) compared to the analogous strain not expressing the mutarotase is demonstrated.

Example 21b

Measurements of D-Xylose Fermentation of the Yeast Strains Described in Example 20a and 20b The two yeast strains adapted to D-xylose metabolism (described in Example 21a) are inoculated individually in liquid Yeast Peptone Xylose (YPX) using baffled shake flasks. The cultures are incubated at 30° C. in a shaker running at 225 RPM until OD600≈1.0. Thereafter the cultures are harvested by centrifugation and resuspended in 20 ml of liquid Yeast Peptone supplemented with 50 g/L of D-xylose, using shake flask with two side necks, at a final cell concentration of OD600=5. Shake flasks are sealed with bungs containing fermentation locks inserted. Side necks are fitted with gas impermeable resealable rubber stoppers. Fermentation is conducted at 30° C. in a shaker running at 100 RPM. Samples are withdrawn, though the resealable rubber stoppers, using a hypodermic needle and syringe and adjusted to pH=9.0 using 2 M NaOH. Ethanol concentrations are measured using the Megazyme Ethanol Assay Kit: K-ETOH (Megazyme International, Ireland) according to the manufacturer's instruction and with appropriated dilutions of samples. Fermentation progression for each of the two strains is determined by plotting the ethanol concentration as a function of time. Rates are given by the slope of the linear part of the curve, subsequent the initial diauxic shift between aerobic growth and anaerobic fermentation. A faster fermentation rate of the strain expressing the aldose-1-epimerase, compared to the congenetic strain without this gene, is demonstrated.

REFERENCES

Anderson R. L. and Allison D. P. (1965) Purification and Characterization of D-Lyxose Isomerase. *J. Biol. Chem.* 240, 2367-2372.

Ausubel F. M., Brent R., Kingston R. E., Moore D., Seidman J. G., Smith J. A., and Struhl K., eds (1995 (and periodic supplements)) *Current Protocols in Molecular Biology*, Vol. ch. 9, 13 and 16. John Wiley & Sons, New York, N.Y.

Bailey J. M., Fishman P. H., and Pentchev P. G. (1969) Studies on Mutarotases. III. Isolation and characterization of a mutarotase from bovine kidney cortex. *J. Biol. Chem.* 244, 781-788.

Becker D. M. and Guarente L. (1991) High-efficiency transformation of yeast by electroporation. *Methods Enzymol.* 194, 182-187.

Brahma A. and Bhattaeharyya D. (2004) UDP-galactose 4-epimerase from *Kluyveromyces fragilis*. Evidence for independent mutarotation site. *Eur. J. Biochem.* 271, 58-68.

Burnett M. E., Liu J., and Conway T. (1992) Molecular Characterization of the *Zymomonas mobilis* Enolase (eno) Gene. *J. Bact.* 174, 6548-6553.

Cheng H., Jiang N., Shen A., and Feng Y. (2005) Molecular cloning and functional expression of D-arabitol dehydrogenase gene from *Gluconobacter oxydans* in *Escherichia coli*. *FEMS Microbial. Lett.* 252, 35-42.

Conway T., Sewell G. W., and Ingram L. O. (1987) Glyceraldehyde-3-Phosphate Dehydrogenase Gene from *Zymomonas mobilis*: Cloning, Sequencing, and Identification of Promoter Region. *J. Bact.* 169, 5653-5662.

Dische Z. and Borenfreund E. (1951) A new spectrophotometric method for the detection and determination of keto sugars and trioses. *J. Biol. Chem.* 192, 583.

Dothie J. M., Giglio J. R., Moore C. B., Taylor S. S., and Hartley B. S. (1985) Ribitol dehydrogenase of *Klebsiella aerogenes*. Sequence and properties of wild-type and mutant strains. *Biochem. J.* 230, 569-578.

Eberts T. J., Sample R. H. B., Glick M. R., and Gregory H. E. (1979) A Simplified, Colorimetric Micromethod for Xylose in Serum or Urine, with Phloroglucinol. *Clin. Chem.* 25, 1440-1443.

Gait M. J., ed (1984) *Oligonucleotide Synthesis: A Practical Approach*. Oxford University Press.

Goldstein A. L. and McCusker J. H. (1999) Three New Dominant Drug Resistance Cassettes for Gene Disruption in *Saccharomyces cerevisiae*. *Yeast* 15, 1541-1553.

Güldener U., Heck S., Fiedler T., Beinhauer J., and Hegemann J. H. (1996) A new efficient gene disruption cassette for repeated use in budding yeast. *Nucleic Acids Res.* 24, 2519-2524.

Izumori K., Rees A. W., and Elbein A. D. (1975) Purification, Crystallization, and Properties of D-Ribose Isomerase from *Mycobacterium smegmatis*. *J. Biol. Chem.* 250, 8085-8087.

Kavanagh K., Klimcek M., Nidetsky B., and Wilson D. K. (2003) Structure of xylose reductase bound to NAD+ and the basis for single and dual co-substrate specificity in family 2 aldo-keto reductases. *Biochem. J.* 373, 319-326.

Lilley D. M. J. and Dahlberg J. E., eds (1992) *Methods in Enzymology: DNA Structures Part A: Synthesis and Physical Analysis of DNA*, Vol. 211. Academic Press, Majumdar S., Ghatak J., Mukherji S., Bhattacharjee H., and Bhaduri A. (2004) UDPgalactose 4-epimerase from *Saccharomyces cerevisiae*: A bifunctional enzyme with aldose 1-epimerase activity. *Eur. J. Biochem.* 271, 753-759.

Mumberg D., Mailer R., and Funk M. (1995) Yeast vectors for the controlled expression of heterologous proteins in different genetic backgrounds. *Gene* 156, 119-122.

Nakamura Y., Gojobori T., and Ikemura T. (2000) Codon Usage tabulated from international DNA sequence databases: status for the year 2000. *Nucleic Acids Res.* 28, 292.

Richard P., Londesborough J., Putkonen M., Kalkkinen N., and Penttila M. (2001) Cloning and Expression of a Fungal L-Arabinitol 4-Dehydrogenase Gene. *J. Biol. Chem.* 276, 40631.40637.

Roe B., Crabtree J., and Kahn A., eds (1996) *DNA Isolation and Sequencing: Essential Techniques*. John Wiley & Sons.

Rose M. D., Winston F., and Hieter P., eds (1990) *Methods in Yeast Genetics: A Laboratory Course Manual*. Cold Spring Harbor Laboratory Press.

Ryu K.-S., Kim C., Kim I., Yoo S., Choi B.-S., and Park C. (2004) NMR Application Probes a Novel and Ubiquitous Family of Enzymes That Alter Monosaccharide Configuration. *J. Biol. Chem.* 279, 25544-25548.

Sambrook, E. F. Fritsch, and T. Maniatis, 1989, *Molecular Cloning: A Laboratory Manual*, Second Edition, Books 1-3, Cold Spring Harbor Laboratory Press.

Shimonishi T. and Izumori K. (1996) A new enzyme, L-ribose isomerase from *Acinetobacter* sp. strain DL-28. *J. Ferment. Bioeng.* 81, 493-497.

Verho R., Putkonen M., Londesborough J., Penttila M., and Richard P. (2004) A Novel NADH-linked L-Xylulose Reductase in the L-Arabinose Catabolic Pathway of Yeast. *J. Biol. Chem.* 279, 14746-14751.

Witteveen C. F. B., Weber F., Busink. R., and Visser J. (1994) Isolation and characterisation of two xylitol dehydrogenases from *Aspergillus niger*. *Microbiol.* 140, 1679-1685.

Woodyer R., Simurdiak M., van der Donk W. A., and Zhao H. (2005) Heterologous Expression, Purification, and Characterization of a Highly Active Xylose Reductase from *Neurospora crassa*. *Appl. Environ. Microbiol.* 71, 1642-1647.

Yanase H., Sato D., Yamamoto K., Matsuda S., Yamamoto S., and Okamoto K. (2007) Genetic Engineering of *Zymobacter palmae* for Production of Ethanol from Xylose. *Appl. Environ. Microbiol.* 73, 2592-2599.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry and molecular biology or related fields are intended to be within the scope of the following claims.

Sequence Listing:

```
>SEQ.ID.NO. 1 (AAD20245 version 1):
The amino acid sequence encoded by this nucleotide sequence is
shown as SEQ ID No 47.
   1 GAATTCCTAGAAATAATTTTGTTTAACTTTAAGAAGGAGGAGCTAGCC M   A   T   F   T   I   S   K   E   S   L   P   F   R   A   D
  49 ATG GCT ACT TTT ACA ATC AGC AAG GAG AGC CTG CCA TTC AGA GCA GAT
```

-continued

```
         K   S   I   S   Q   I   T   L   S   N   E   R   L   T   I   V
 97     AAA TCA ATT TCC CAA ATT ACT TTG TCA AAT GAA AGA TTA ACA ATC GTC

V   H   D   Y   G   A   R   A   H   Q   L   L   T   P   D   K
145     GTA CAC GAC TAT GGA GCT AGA GCC CAC CAG CTG TTG ACA CCT GAC AAA

N   G   T   F   E   N   I   L   L   S   K   N   D   S   E   T
193     AAC GGT ACA TTT GAA AAC ATC TTG TTG TCC AAG AAT GAT TCT GAA ACT

Y   A   N   D   G   G   Y   Y   G   V   I   C   G   P   V   A
241     TAT GCA AAT GAT GGC GGC TAT TAT GGT GTT ATT TGT GGT CCT GTT GCT

G   R   I   S   G   A   T   Y   D   S   V   S   L   E   A   N
289     GGC AGA ATA TCT GGA GCT ACT TAT GAC TCA GTG AGC TTA GAA GCC AAC

E   G   K   N   N   L   H   S   G   S   H   G   W   E   R   Q
337     GAG GGC AAA AAT AAC TTA CAT TCA GGC TCA CAC GGT TGG GAA AGA CAA

F   W   S   Y   H   T   F   E   T   A   S   S   L   G   I   K
385     TTT TGG AGC TAT GAG ACA TTT GAG ACT GCT TCT TCA TTG GGA ATA AAA

L   S   L   R   D   E   E   S   G   F   P   G   Q   I   Q   A
433     CTG TCA TTG AGA GAC GAA GAA TCT GGT TTT CCA GGC CAG ATT CAA GCA

E   V   T   Y   K   L   T   D   N   K   L   E   V   T   I   S
481     GAA GTA ACC TAC AAA TTA ACC GAT AAT AAA CTG GAA GTA ACA ATA AGC

G   L   S   V   T   D   T   V   F   N   P   A   W   H   P   Y
529     GGA TTA TCA GTT ACT GAT ACT GTT TTT AAT CCT GCC TGG CAC CCT TAT

F   N   L   S   A   E   L   S   T   T   H   E   H   F   I   Q
577     TTC AAT CTT AGC GCA GAA CTT AGC ACC ACT CAC GAA CAC TTC ATA CAA

A   N   V   D   F   L   V   E   T   N   Q   H   N   I   P   T
625     GCC AAC GTG GAC TTT TTA GTA GAA ACC AAT CAG GAG AAC ATC CCT ACC

G   H   L   L   T   V   D   D   S   S   Y   S   I   K   E   S
673     GGA AGA CTG CTT ACT GTT GAT GAT TCA AGC TAT TCT ATT AAA GAA AGC

V   S   I   K   K   L   L   K   D   N   P   E   G   L   D   D
721     GTC TCC ATT AAG AAG TTG TTG AAG GAT AAC CCA GAA GGT TTG GAC GAT

C   F   V   F   N   P   K   G   D   K   S   L   M   L   Y   D
769     TGC TTT GTT TTC AAT CCA AAA GGA GAC AAA TCC CTT ATG TTA TAC GAT

P   L   S   G   R   K   L   V   A   Q   T   D   R   Q   A   V
817     CCA CTG AGC GGT AGA AAA TTG GTT GCA CAA ACT GAT CGT CAA GCC GTC

V   I   Y   T   A   T   N   P   H   I   E   S   M   I   N   G
865     GTT ATT TAC ACC GCA ACG AAC CCA GAG ATT GAA TCA ATG ATA AAT GGT

R   P   M   S   K   N   R   G   I   A   I   E   F   Q   E   I
913     AGA CCT ATG TCC AAA AAT AGA GGC ATA GCC ATT GAG TTT CAA GAA ATC

P   D   L   V   H   H   P   E   W   G   T   I   E   L   K   A
961     CCG GAT CTT GTT CAC CAC CCA GAA TGG GGA ACC ATT GAA TTG AAA GCT

G   Q   K   K   T   F   I   T   H   Y   L   F   T   T   N   *
1009    GGC CAA AAG AAA ACT TTT ATC ACT GAG TAT TTG TTC ACC ACT AAC TAG

1057 CCTAGGCTCGAGGAATTC

>SEQ.ID.NO. 2:
The amino acid sequence encoded by this nucleotide sequence is
shown as SEQ ID No 48.
   1 GAATTCCTAGAAATAATTTGTTTAACTTTAAGAAGGAGGAGCTAGCC M   A   K   E   Y   F   P   Q   I   Q   K   I   K   F   E   G
 49     ATG GCC AAA GAA TAC TTT CCA CAA ATA CAG AAG ATT AAG TTT GAA GGC K   D   S   K   N   P   L   A   F   H   Y   Y   D   A   E   K
 97     AAA GAT TCA AAG AAT CCA CTG GCC TTC CAT TAT TAT GAT GCA GAA AAG E   V   M   G   K   K   M   K   D   W   L   R   F   A   M   A
145     GAA GTG ATG GGT AAG AAA ATG AAA GAC TGG CTG AGA TTC GCT ATG GCT W   W   H   T   L   C   A   E   G   A   D   Q   F   G   G
193     TGG TGG CAT ACC TTA TGT GCT GAA GGT GCA GAT CAA TTC GGT GGC GGT T   K   S   F   P   W   N   E   G   T   D   A   I   E   I   A
241     ACG AAG AGC TTT CCT TGG AAT GAG GGT ACT GAT GCA ATA GAA ATA GCA
```

-continued

```
       K   Q   K   V   D   A   G   F   E   I   M   Q   K   L   G   I
289  AAA CAA AAG GTT GAC GCA GGC TTT GAG ATT ATG CAA AAG CTG GGT ATT

P   Y   Y   C   F   H   D   V   D   L   V   S   E   G   N   S
337  CCT TAT TAT TGT TTT CAT GAC GTG GAC TTG GTA TCC GAA GGA AAT AGC

T   E   E   Y   E   S   N   L   K   A   V   V   A   Y   L   K
385  ATC GAA GAG TAC GAA AGC AAT CTG AAG GCT GTC GTT GCA TAT CTG AAG

E   K   Q   K   E   T   G   I   K   L   L   W   S   T   A   N
433  GAG AAG CAA AAG GAA ACG GGT ATA AAG TTG TTA TGG TCA ACA GCA AAT

V   F   G   H   K   R   Y   M   N   G   A   S   T   N   P   D
481  GTC TTC GGT CAT AAA AGA TAC ATG AAC GGT GCC TCA ACA AAC CCA GAC

F   D   V   V   A   R   A   I   V   Q   I   K   N   A   I   D
529  TTT GAC GTT GTG GCA CGT GCA ATA GTT CAA ATT AAG AAC GCT ATC GAT

A   G   I   E   L   G   A   E   N   Y   V   F   W   G   G   R
577  GCT GGC ATA GAG TTG GGC GCC GAG AAT TAC GTT TTC TGG GGT GGC CGT

E   G   Y   M   S   L   L   N   T   D   Q   K   R   E   K   E
625  GAG GGT TAT ATG AGC CTT TTA AAT ACG GAT CAA AAA CGT GAG AAG GAA

H   M   A   T   M   L   T   M   A   R   D   Y   A   R   S   K
673  CAC ATG GCT ACA ATG CTT ACG ATG GCC CGT GAC TAT GCT AGA TCA AAA

G   F   K   G   T   F   L   I   E   P   K   P   M   E   P   T
721  GGT TTT AAG GGT ACA TTC TTG ATA GAA CCT AAA CCG ATG GAA CCA ACA

K   H   Q   Y   D   V   D   T   E   T   A   I   G   E   L   K
769  AAG CAC CAA TAT GAT GTA GAT ACC GAA ACC GCA ATT GGA TTT TTG AAG

A   H   N   L   D   K   D   F   K   V   N   I   E   V   N   H
817  GCA CAT AAC TTG GAC AAG GAT TTC AAG GTA AAC ATA GAA GTA AAT CAT

A   T   L   A   G   H   T   F   E   H   E   L   A   C   A   V
865  GCA ACG TTG GCA GGT CAT ACT TTC GAA CAC GAA TTA GCT TGC GCA GTA

D   A   G   M   L   G   S   I   D   A   N   R   G   D   Y   Q
913  GAT GCT GGA ATG TTA GGT AGC ATC GAT GCA AAT AGA GGT GAT TAC CAG

N   G   W   D   T   D   Q   F   P   I   D   Q   Y   E   L   V
961  AAT GGC TGG GAT ACT GAT CAA TTC CCA ATA GAC CAG TAT GAA CTG GTA

Q   A   W   M   E   I   I   R   G   G   G   F   V   T   G   G
1009 CAG GCC TGG ATG GAA ATA ATC CGT GGC GGT GGT TTC GTG ACA GGT GGA

T   N   E   D   A   K   T   R   R   N   S   T   D   L   E   D
1057 ACA AAT TTT GAT GCA AAA ACT CGT AGA AAC TCA ACT GAT CTT GAG GAT

I   T   I   A   H   V   S   G   M   D   A   M   A   R   A   L
1105 ATC ATT ATC GCT CAC GTA TCT GGC ATG GAC GCT ATG GCC CGT GCA TTG

E   N   A   A   K   L   L   Q   E   S   P   Y   T   K   M   K
1153 GAG AAC GCT GCT AAG CTT TTA CAA GAG TCC CCA TAT ACG AAG ATG AAG

K   E   R   Y   A   S   E   D   S   G   I   G   K   D   F   E
1201 AAA GAG AGA TAT GCT TCT TTT GAT AGC GGT ATA GGA AAA GAC TTC GAG

D   G   K   L   T   L   E   Q   V   Y   E   Y   G   K   K   N
1249 GAT GGA AAG CTG ACA CTG GAG CAA GTG TAC GAA TAT GGT AAA AAG AAT

G   E   P   K   Q   T   S   G   K   Q   E   L   Y   E   A   I
1297 GGT GAA CCA AAA CAG ACC TCA GGA AAG CAG GAA TTA TAT GAA GCC ATT

V   A   M   Y   Q   *
1345 GTG GCT ATG TAC CAA TAG CCTAGGCTCGAGGAATTC

>SEQ.ID.NO. 3:
The amino acid sequence encoded by this nucleotide sequence is
shown as SEQ ID No 49.
   1 GAATTCCTAGAAATAATTTTGTTTAACTTTAAGAAGGAGGAGCTAGCC M   E   Y   F   K   N   V   P   Q   I   K   Y   E   G   P   K
  49 ATG GAA TAT TTC AAA AAC GTG CCA CAG ATC AAG TAT GAA GGT CCT AAA S   N   N   P   Y   A   F   K   F   Y   N   P   D   E   I   I
  97 AGC AAT AAC CCT TAT GCA TTT AAG TTC TAT AAC CCA GAT GAA ATT ATA
```

```
            D   G   K   P   L   K   E   H   L   R   F   S   V   A   Y   W
        145 GAT GGA AAA CCA TTA AAA GAA CAC TTA AGA TTT AGO GTA GCC TAC TGG

H   T   F   T   A   N   G   T   D   P   F   G   A   P   T   M
        193 CAT ACA TTT ACC GCT AAC GGA ACG GAT CCA TTT GGT GCA CCG ACT ATG

Q   R   P   W   D   H   F   T   D   P   M   D   I   A   K   A
        241 CAG CGT CCT TGG GAT CAT TTT ACC GAC CCT ATG GAC ATA GCA AAA GCA

R   V   E   A   A   F   E   L   F   E   K   L   D   V   P   F
        289 CGT GTG GAA GCC GCA TTC GAG CTT TTT GAA AAA TTG GAT GTT CCA TTC

F   C   F   H   D   R   D   I   A   P   E   G   E   T   L   R
        337 TTC TGT TTT CAT GAC AGA GAT ATA GCT CCG GAA GGT GAA ACA TTG AGA

E   T   N   K   N   L   D   T   I   V   A   M   I   K   D   Y
        385 GAA ACC AAC AAA AAC TTA GAT ACT ATC GTT GCT ATG ATT AAA GAC TAC

L   K   T   S   K   T   K   V   L   W   G   T   A   N   L   F
        433 TTA AAA ACG TCA AAG ACT AAA GTT CTT TGG GGC ACT GCT AAT TTG TTT

S   N   P   R   F   V   H   G   A   A   T   S   C   N   A   D
        481 TCT AAT CCA CGT TTC GTG CAT GGC GCT GGC ACA TCA TGT AAT GCA GAC

V   F   A   Y   A   A   A   Q   V   K   K   A   L   E   I   T
        529 GTA TTT GCT TAT GCA GCC GCT CAA GTT AAA AAG GCC TTA GAG ATT ACC

K   E   L   G   G   Q   N   Y   V   F   W   G   R   E   G
        577 AAA GAG TTA GGA GGC CAG AAT TAT GTT TTC TGG GGT GGT CGT GAG GGA

Y   E   T   L   L   N   T   D   M   E   L   E   L   D   N   L
        625 TAT GAG ACA CTT TTA AAT ACT GAT ATG GAG TTG GAA TTA GAT AAT TTA

A   R   F   L   H   M   A   V   E   Y   A   Q   E   I   G   F
        673 GCA AGA TTC TTA CAC ATG GCA GTA GAA TAT GCT CAG GAA ATT GGT TTT

E   G   Q   F   L   I   E   P   K   P   K   E   P   T   K   H
        721 GAA GGA CAG TTC TTG ATC GAG CCT AAA CCA AAG GAA CCA ACA AAG CAT

Q   Y   D   F   D   A   A   S   V   H   A   F   L   K   K   Y
        769 CAG TAT GAT TTC GAC GCT GCT TCT GTA CAC GCC TTT TTG AAG AAG TAT

D   L   D   K   Y   F   K   L   N   I   E   A   N   H   A   T
        817 GAT TTG GAT AAA TAC TTT AAG TTG AAC ATA GAG GCT AAT CAC GCA ACG

L   A   G   H   D   F   Q   H   E   L   R   Y   A   R   I   N
        865 TTG GCA GGT CAC GAT TTT CAA CAC GAA TTG AGA TAC GCC CGT ATT AAT

N   M   L   G   S   I   D   A   N   M   G   D   M   L   L   G
        913 AAC ATG TTA GGT TCC ATA GAT GCC AAC ATG GGT GAC ATG TTG CTG GGT

W   D   T   D   Q   Y   P   T   D   I   R   M   T   T   L   A
        961 TGG GAT ACT GAT CAA TAC CCA ACG GAT ATT AGA ATG ACA ACT TTA GCA

M   Y   E   V   I   K   M   G   G   F   N   K   G   G   L   N
       1009 ATG TAC GAG GTC ATT AAA ATG GGA GGT TTT AAC AAA GGA GGT TTG AAT

F   D   A   K   V   R   H   A   S   F   E   P   E   D   L   F
       1057 TTC GAT GCT AAA GTG CGT CGT GCC TCT TTT GAA CCT GAA GAC CTT TTT

L   G   H   I   A   G   M   D   A   F   A   K   G   F   K   V
       1105 CTT GGA CAT ATT GCC GGA ATG GAT GCA TTT GCA AAA GGT TTC AAG GTC

A   Y   K   L   V   K   D   G   V   F   D   R   F   I   E   E
       1153 GCT TAT AAG CTT GTT AAG GAT GGT GTA TTT GAT AGA TTC ATT GAA GAG

R   Y   K   S   Y   R   E   G   I   G   A   E   I   V   S   G
       1201 AGA TAC AAA TCC TAT CGT GAA GGT ATA GGT GCT GAA ATC GTT TCA GGT

K   A   N   F   K   T   L   E   E   Y   A   L   N   N   P   K
       1249 AAG GCC AAT TTT AAG ACT TTA GAG GAA TAT GCA TTG AAT AAC CCA AAA

I   E   N   K   S   G   K   Q   E   L   L   E   S   I   L   N
       1297 ATC GAA AAC AAA AGC GGT AAA CAG GAA CTG CTG GAA TCT ATT TTG AAT

Q   Y   L   F   S   E   *
       1345 CAA TAT TTG TTC TCT GAA TAG CCTAGGCTCGAGGAATTC

>SEQ.ID.NO. 4:
  1 GCTAGCCATG GCCACTACCC CATTTGATGC TCCAGATAAG
```

-continued

>SEQ.ID.NO. 5:
1 CTCGAGCCTA GGCTAGTGTT TCAATTCACT TTCCATCTTG GCC

>SEQ.ID.NO. 6:
1 GCTAGCCATG GCTTCTATTA AGTTGAACTC TGGTTACG

>SEQ.ID.NO. 7:
1 CTCGAGCCTA GGCTAGACGA AGATAGGAAT CTTGTCCCAG TCCC

>SEQ.ID.NO. 8:
1 GCTAGCCATG GCTGCTAACC CTTCCTTGGT GTTG

>SEQ.ID.NO. 9:
1 CTCGAGCCTA GGCTACTCAG GGCCGTCAAT GAGACACTTG ACAGCACCC

>SEQ.ID.NO. 10:
1 TAGCTAGCAT GTTATCAGTA CCTGATTATG AG

>SEQ.ID.NO. 11:
1 ATCTCGAGTT ACTTTAAGAA TGCCTTAGTC ATGCC

>SEQ.ID.NO. 12:
1 TAGCTAGCAT GAATTTAGTT GAAACAGCCC AAGC

>SEQ.ID.NO. 13:
1 ATCTCGAGCT AATATTTGAT TGCTTGCCCA GCC

>SEQ.ID.NO. 14:
1 TAGCTAGCAT GCTAGAAGCA TTAAAACAAG AAG

>SEQ.ID.NO. 15:
1 ATCTCGAGTT ACTTGCGAAC TGCATGATCC TTAG

>SEQ.ID.NO. 16:
1 TAGCTAGCAT GACAGCTCAG TTACAAAGTG AAAG

>SEQ.ID.NO. 17:
1 ATCTCGAGTC AGGAAAATCT GTAGACAATC TTGG

>SEQ.ID.NO. 18:
1 TAGCTAGCAT GGCCAGATTT TCCGCTGAAG ATATGCG

>SEQ.ID.NO. 19:
1 TAGTTTAAAC TTGCCATCAT CATTCCCTAG AAACTGC

>SEQ.ID.NO. 20:
1 TAGTCGACAG TGTGTAAGAG TGTACCATTT ACT

>SEQ.ID.NO. 21:
1 TACTCGAGTT TCCCTTTTTC TGCCTTTTTC GGTG

>SEQ.ID.NO. 22:
1 TAGTTTAAAC TGATGGTGTG GAAGACATAG ATGG

>SEQ.ID.NO. 23:
1 TAGTTTAAAC AGTTATGTTT AAAAAATCAA CTTTCTTTCC

>SEQ.ID.NO. 24:
1 TAGTCGACAA CCAGGTCCTT GTGTGCCGCT GTT

>SEQ.ID.NO. 25:
1 TACTCGAGTC CTATCGAGTT ACACTGCTAG TG

>SEQ.ID.NO. 26:
1 TAGTTTAAAC ATTGCTTAGC ATAGCTGCCA CTAACC

>SEQ.ID.NO. 27:
1 TAGTCGACTG ACATGTATGG GTTGAAAATA TTTAG

>SEQ.ID.NO. 28:
1 TACCTAGGTT TTAGGCTGGT ATCTTGATTC

>SEQ.ID.NO. 29:
1 TAGTCGACTG TTTAAAGATT ACGGATATTT AAC

>SEQ.ID.NO. 30:
1 TACCTAGGTT TTAGTTTATG TATGTGTTTT TTGTAG

>SEQ.ID.NO. 31:
1 TAGTCGACAA AAGGTCTAAC ATCCTTTGAG TTATG

-continued

>SEQ.ID.NO. 32:
1 TACCTAGGGT TATGTTAACT TTTGTTACTT

>SEQ.ID.NO. 33:
1 TAGTCGACAG GGTAGCCTCC CCATAACATA AAC

>SEQ.ID.NO. 34:
1 TACCTAGGTT TGATTGATTT GACTGTGTTA TTTTGCG

>SEQ.ID.NO. 35:
1 TAGTCGACAT AACAATACTG ACAGTACTAA A

>SEQ.ID.NO. 36:
1 TACCTAGGTT TGAATATGTA TTACTTGGTT ATGG

>SEQ.ID.NO. 37:
1 TAGTCGACCA CATGCAGTGA TGCACGCGCG

>SEQ.ID.NO. 38:
1 TACCTAGGTA TTGTAATATG TGTGTTTGTT TGG

>SEQ.ID.NO. 39:
1 TATCTAGAAT GACTCAATTC ACTGACATTG ATAAGC

>SEQ.ID.NO. 40:
1 TACTCGAGTT AGAAAGCTTT TTTCAAAGGA GAAATTAGC

>SEQ.ID.NO. 41:
1 TAGCTAGCAT GTTGTGTTCA GTAATTCAGA GAC

>SEQ.ID.NO. 42:
1 ATCTCGAGGA TGAGAGTCTT TTCCAGTTCG C

>SEQ.ID.NO. 43:
1 GCTAGCCATG TCTGAACCAG CTCAAAAGAA ACAAAAGG

>SEQ.ID.NO. 44:
1 TACTCGAGAG AAACTGTATC ATTCATCAAA TAGG

>SEQ.ID.NO. 45:
1 GCTAGCCATG GCTGCCGGTG TCCCAAAAAT TGATGCG

>SEQ.ID.NO. 46:
1 TACTCGAGAA CATTGCATTT ATTGGTGTTG AATC

>SEQ.ID.NO. 47:
The amino acid sequence encoded by the nucleotide sequence of SEQ ID No 1.

| M | A | T | F | T | I | S | K | E | S | L | P | F | R | A | D |
| K | S | I | S | Q | I | T | L | S | N | E | R | L | T | I | V |
| V | H | D | Y | G | A | R | A | H | Q | L | L | T | P | D | K |
| N | G | T | F | E | N | I | L | L | S | K | N | D | S | E | T |
| Y | A | N | D | G | G | Y | Y | G | V | I | C | G | P | V | A |
| G | R | I | S | G | A | T | Y | D | S | V | S | L | E | A | N |
| E | G | K | N | N | L | H | S | G | S | H | G | W | E | R | Q |
| F | W | S | Y | E | T | F | E | T | A | S | S | L | G | I | K |
| L | S | L | R | D | E | E | S | G | F | P | G | Q | I | Q | A |
| E | V | T | Y | K | L | T | D | N | K | L | E | V | T | I | S |
| G | L | S | V | T | D | T | V | E | N | P | A | W | H | P | Y |
| F | N | L | S | A | E | L | S | T | H | E | H | F | I | Q |   |
| A | N | V | D | F | L | V | E | T | N | Q | E | N | I | P | T |
| G | R | L | T | V | D | D | S | S | Y | S | I | K | E | S |   |
| V | S | I | K | K | L | K | D | N | P | E | G | L | D | D |   |
| C | F | V | F | N | P | K | G | D | K | S | L | M | L | Y | D |
| P | L | S | G | R | K | L | V | A | Q | T | D | R | Q | A | V |

```
V    I    Y    T    A    T    N    P    E    I    E    S    M    I    N    G
R    P    M    S    K    N    R    G    I    A    I    E    F    Q    E    I
P    D    L    V    H    H    P    E    N    G    T    I    E    L    K    A
G    Q    K    K    T    F    I    T    E    Y    L    E    T    T    N    *
```

>SEQ. ID. NO. 48 (ACCESSION NUMBER CAB76571 version 1):
The amino acid sequence encoded by the nucleotide sequence of
SEQ ID No 2.

```
M    A    K    E    Y    F    P    Q    I    Q    K    I    K    F    E    G
K    D    S    K    N    P    L    A    F    H    Y    Y    D    A    E    K
E    V    M    G    K    K    M    K    D    W    L    R    F    A    M    A
W    W    H    T    L    C    A    E    G    A    D    Q    F    G    G    G
T    K    S    F    P    W    N    E    G    T    D    A    I    E    I    A
K    Q    K    V    D    A    G    F    E    I    M    Q    K    L    G    I
P    Y    Y    C    F    H    D    V    D    L    V    S    E    G    N    S
I    E    E    Y    E    S    N    L    K    A    V    V    A    Y    L    K
E    K    Q    K    E    T    G    I    K    L    L    W    S    T    A    N
V    F    G    H    K    R    Y    M    N    G    A    S    T    N    P    D
F    D    V    V    A    R    A    I    V    Q    I    K    N    A    I    D
A    G    I    E    L    G    A    E    N    Y    V    F    W    G    G    R
E    G    Y    M    S    L    L    N    T    D    Q    K    R    E    K    E
H    M    A    T    M    L    T    M    A    R    D    Y    A    R    S    K
G    F    K    G    T    F    L    I    E    P    K    P    M    E    P    T
K    H    Q    Y    D    V    D    T    E    T    A    I    G    E    L    K
A    H    N    L    D    K    D    E    K    V    N    I    E    V    N    H
A    T    L    A    G    H    T    F    E    H    E    L    A    C    A    V
D    A    G    M    L    G    S    I    D    A    N    R    G    D    Y    Q
N    G    W    D    T    D    Q    F    P    I    D    Q    Y    E    L    V
Q    A    W    M    E    I    I    R    G    G    G    F    V    T    G    G
T    N    F    D    A    K    T    R    R    N    S    T    D    L    E    D
T    I    I    A    H    V    S    G    M    D    A    M    A    R    A    L
E    N    A    A    K    L    L    Q    E    S    P    Y    T    K    M    K
K    E    R    Y    A    S    E    D    S    G    I    G    K    D    F    E
D    G    K    L    T    L    E    Q    V    Y    E    Y    G    K    K    N
G    E    P    K    Q    T    S    G    K    Q    E    L    Y    E    A    I
V    A    M    Y    Q    *
```

>SEQ. ID. NO. 49 (ACCESSION NUMBER P22842 version 1):
The amino acid sequence encoded by the nucleotide sequence of
SEQ ID No 3.

```
M    E    Y    F    K    N    V    P    Q    I    K    Y    E    G    A    K
S    N    N    P    Y    A    F    K    E    Y    N    P    D    E    I    I
D    G    K    P    L    K    E    H    L    R    F    S    V    A    Y    W
H    T    F    T    A    N    G    T    D    P    F    G    A    P    T    M
Q    R    P    W    D    H    F    T    D    P    M    D    I    A    K    A
```

-continued

| | | | | | | | | | | | | |
|---|---|---|---|---|---|---|---|---|---|---|---|---|
| R | V | E | A | A | F | E | L | F | E | K | L | D | V | P | F |
| F | C | F | H | D | R | D | I | A | P | E | G | E | T | L | R |
| E | T | N | K | N | L | D | T | I | V | A | M | I | K | D | Y |
| L | K | T | S | K | T | K | V | L | W | G | T | A | N | L | F |
| S | N | P | R | F | V | H | G | A | A | T | S | C | N | A | D |
| V | F | A | Y | A | A | A | Q | V | K | K | A | L | E | I | T |
| K | E | L | G | G | Q | N | Y | V | F | W | G | G | R | E | G |
| Y | E | T | L | L | N | T | D | M | E | L | E | L | D | N | L |
| A | R | F | L | H | M | A | V | E | Y | A | Q | E | I | G | F |
| E | G | Q | F | L | I | E | P | K | P | K | E | P | T | K | H |
| Q | Y | D | F | D | A | A | S | V | H | A | F | L | K | K | Y |
| D | L | D | K | Y | F | K | L | N | I | E | A | N | H | A | T |
| L | A | G | H | D | F | Q | H | E | L | R | Y | A | R | I | N |
| N | M | L | G | S | I | D | A | N | M | G | D | M | L | L | G |
| W | D | T | D | Q | Y | P | T | D | I | R | M | T | T | L | A |
| N | Y | E | V | I | K | M | G | G | E | N | K | G | G | L | N |
| F | D | A | K | V | R | R | A | S | F | E | P | E | D | L | F |
| L | G | H | I | A | G | M | D | A | F | A | K | G | F | K | V |
| A | Y | K | L | V | K | D | G | V | F | D | R | F | I | E | E |
| R | Y | K | S | Y | R | E | G | I | G | A | E | I | V | S | G |
| K | A | N | F | K | T | L | E | E | Y | A | L | N | N | P | K |
| I | E | N | K | S | G | K | Q | E | L | L | E | S | I | L | N |
| Q | Y | L | F | S | E | * | | | | | | | | | |

The invention claimed is:

1. A transformed microorganism capable of: (i) converting xylose to a xylulose at a higher rate than the equivalent microorganism prior to transformation; and/or (ii) a higher growth rate in the presence of xylose than the equivalent microorganism prior to transformation; and/or (iii) a higher metabolism of xylose than the equivalent microorganism prior to transformation;

wherein said microorganism has been transformed with a promoter that enables the microorganism to overexpress an endogenous aldose-1-epimerase, and/or wherein said microorganism has been transformed with a nucleotide sequence encoding an aldose-1-epimerase, and said microorganism has been transformed with at least one expression vector comprising a heterologous nucleotide sequence encoding xylose isomerase, or said microorganism has been transformed with at least one expression vector comprising a heterologous nucleotide sequence encoding a xylose isomerase and a xylulokinase, or said microorganism has been transformed with at least one expression vector comprising a heterologous nucleotide sequence encoding a xylose isomerase wherein said microorganism has been transformed with a promoter that enables the microorganism to overexpress an endogenous xylulokinase, and wherein said microorganism is a transformed yeast.

2. An inoculum comprising a microorganism according to claim 1.

3. A culture medium comprising a microorganism according to claim 1.

* * * * *

SEQUENCE LISTING

```
<160> NUMBER OF SEQ ID NOS: 49

<210> SEQ ID NO 1
<211> LENGTH: 1074
<212> TYPE: DNA
<213> ORGANISM: Artificial Sequence
<220> FEATURE:
<223> OTHER INFORMATION: Synthetic construct (L1MR)
<220> FEATURE:
<221> NAME/KEY: CDS
<222> LOCATION: (49)..(1053)

<400> SEQUENCE: 1
gaattcctag aaataatttt gtttaacttt aagaaggagg agctagcc atg gct act         57
                                                    Met Ala Thr
                                                     1 ttt aca atc agc aag gag agc ctg cca ttc aga gca gat aaa tca att        105
Phe Thr Ile Ser Lys Glu Ser Leu Pro Phe Arg Ala Asp Lys Ser Ile
  5                  10                  15 tcc caa att act ttg tca aat gaa aga tta aca atc gtc gta cac gac        153
Ser Gln Ile Thr Leu Ser Asn Glu Arg Leu Thr Ile Val Val His Asp
 20                  25                  30                  35 tat gga gct aga gcc cac cag ctg ttg aca cct gac aaa aac ggt aca        201
Tyr Gly Ala Arg Ala His Gln Leu Leu Thr Pro Asp Lys Asn Gly Thr
                 40                  45                  50
```

| | | |
|---|---|---|
| ttt gaa aac atc ttg ttg tcc aag aat gat tct gaa act tat gca aat<br>Phe Glu Asn Ile Leu Leu Ser Lys Asn Asp Ser Glu Thr Tyr Ala Asn<br>           55                   60                65 | | 249 |
| gat ggc ggc tat tat ggt gtt att tgt ggt cct gtt gct ggc aga ata<br>Asp Gly Gly Tyr Tyr Gly Val Ile Cys Gly Pro Val Ala Gly Arg Ile<br>        70                   75                    80 | | 297 |
| tct gga gct act tat gac tca gtg agc tta gaa gcc aac gag ggc aaa<br>Ser Gly Ala Thr Tyr Asp Ser Val Ser Leu Glu Ala Asn Glu Gly Lys<br>85                    90                   95 | | 345 |
| aat aac tta cat tca ggc tca cac ggt tgg gaa aga caa ttt tgg agc<br>Asn Asn Leu His Ser Gly Ser His Gly Trp Glu Arg Gln Phe Trp Ser<br>100                 105               110             115 | | 393 |
| tat gag aca ttt gag act gct tct tca ttg gga ata aaa ctg tca ttg<br>Tyr Glu Thr Phe Glu Thr Ala Ser Ser Leu Gly Ile Lys Leu Ser Leu<br>                    120               125             130 | | 441 |
| aga gac gaa gaa tct ggt ttt cca ggc cag att caa gca gaa gta acc<br>Arg Asp Glu Glu Ser Gly Phe Pro Gly Gln Ile Gln Ala Glu Val Thr<br>                135               140             145 | | 489 |
| tac aaa tta acc gat aat aaa ctg gaa gta aca ata agc gga tta tca<br>Tyr Lys Leu Thr Asp Asn Lys Leu Glu Val Thr Ile Ser Gly Leu Ser<br>      150                155               160 | | 537 |
| gtt act gat act gtt ttt aat cct gcc tgg cac cct tat ttc aat ctt<br>Val Thr Asp Thr Val Phe Asn Pro Ala Trp His Pro Tyr Phe Asn Leu<br>165                   170               175 | | 585 |
| agc gca gaa ctt agc acc act cac gaa cac ttc ata caa gcc aac gtg<br>Ser Ala Glu Leu Ser Thr Thr His Glu His Phe Ile Gln Ala Asn Val<br>180                 185               190             195 | | 633 |
| gac ttt tta gta gaa acc aat cag gag aac atc cct acc gga aga ctg<br>Asp Phe Leu Val Glu Thr Asn Gln Glu Asn Ile Pro Thr Gly Arg Leu<br>                    200               205             210 | | 681 |
| ctt act gtt gat gat tca agc tat tct att aaa gaa agc gtc tcc att<br>Leu Thr Val Asp Asp Ser Ser Tyr Ser Ile Lys Glu Ser Val Ser Ile<br>                215               220             225 | | 729 |
| aag aag ttg ttg aag gat aac cca gaa ggt ttg gac gat tgc ttt gtt<br>Lys Lys Leu Leu Lys Asp Asn Pro Glu Gly Leu Asp Asp Cys Phe Val<br>      230                235               240 | | 777 |
| ttc aat cca aaa gga gac aaa tcc ctt atg tta tac gat cca ctg agc<br>Phe Asn Pro Lys Gly Asp Lys Ser Leu Met Leu Tyr Asp Pro Leu Ser<br>245                   250               255 | | 825 |
| ggt aga aaa ttg gtt gca caa act gat cgt caa gcc gtc gtt att tac<br>Gly Arg Lys Leu Val Ala Gln Thr Asp Arg Gln Ala Val Val Ile Tyr<br>260                   265               270             275 | | 873 |
| acc gca acg aac cca gag att gaa tca atg ata aat ggt aga cct atg<br>Thr Ala Thr Asn Pro Glu Ile Glu Ser Met Ile Asn Gly Arg Pro Met<br>                    280               285             290 | | 921 |
| tcc aaa aat aga ggc ata gcc att gag ttt caa gaa atc ccg gat ctt<br>Ser Lys Asn Arg Gly Ile Ala Ile Glu Phe Gln Glu Ile Pro Asp Leu<br>                295               300             305 | | 969 |
| gtt cac cac cca gaa tgg gga acc att gaa ttg aaa gct ggc caa aag<br>Val His His Pro Glu Trp Gly Thr Ile Glu Leu Lys Ala Gly Gln Lys<br>      310              315               320 | | 1017 |
| aaa act ttt atc act gag tat ttg ttc acc act aac tagcctaggc<br>Lys Thr Phe Ile Thr Glu Tyr Leu Phe Thr Thr Asn<br>325                   330               335 | | 1063 |
| tcgaggaatt c | | 1074 |

<210> SEQ ID NO 2
<211> LENGTH: 1380
<212> TYPE: DNA

<213> ORGANISM: Artificial Sequence
<220> FEATURE:
<223> OTHER INFORMATION: Synthetic construct (PmXI)
<220> FEATURE:
<221> NAME/KEY: CDS
<222> LOCATION: (49)..(1359)

<400> SEQUENCE: 2

```
gaattcctag aaataatttt gtttaacttt aagaaggagg agctagcc atg gcc aaa        57
                                                    Met Ala Lys
                                                      1 gaa tac ttt cca caa ata cag aag att aag ttt gaa ggc aaa gat tca       105
Glu Tyr Phe Pro Gln Ile Gln Lys Ile Lys Phe Glu Gly Lys Asp Ser
  5                  10                  15 aag aat cca ctg gcc ttc cat tat tat gat gca gaa aag gaa gtg atg       153
Lys Asn Pro Leu Ala Phe His Tyr Tyr Asp Ala Glu Lys Glu Val Met
 20                  25                  30                  35 ggt aag aaa atg aaa gac tgg ctg aga ttc gct atg gct tgg tgg cat       201
Gly Lys Lys Met Lys Asp Trp Leu Arg Phe Ala Met Ala Trp Trp His
                 40                  45                  50 acc tta tgt gct gaa ggt gca gat caa ttc ggt ggc ggt acg aag agc       249
Thr Leu Cys Ala Glu Gly Ala Asp Gln Phe Gly Gly Gly Thr Lys Ser
             55                  60                  65 ttt cct tgg aat gag ggt act gat gca ata gaa ata gca aaa caa aag       297
Phe Pro Trp Asn Glu Gly Thr Asp Ala Ile Glu Ile Ala Lys Gln Lys
         70                  75                  80 gtt gac gca ggc ttt gag att atg caa aag ctg ggt att cct tat tat       345
Val Asp Ala Gly Phe Glu Ile Met Gln Lys Leu Gly Ile Pro Tyr Tyr
     85                  90                  95 tgt ttt cat gac gtg gac ttg gta tcc gaa gga aat agc atc gaa gag       393
Cys Phe His Asp Val Asp Leu Val Ser Glu Gly Asn Ser Ile Glu Glu
100                 105                 110                 115 tac gaa agc aat ctg aag gct gtc gtt gca tat ctg aag gag aag caa       441
Tyr Glu Ser Asn Leu Lys Ala Val Val Ala Tyr Leu Lys Glu Lys Gln
                120                 125                 130 aag gaa acg ggt ata aag ttg tta tgg tca aca gca aat gtc ttc ggt       489
Lys Glu Thr Gly Ile Lys Leu Leu Trp Ser Thr Ala Asn Val Phe Gly
            135                 140                 145 cat aaa aga tac atg aac ggt gcc tca aca aac cca gac ttt gac gtt       537
His Lys Arg Tyr Met Asn Gly Ala Ser Thr Asn Pro Asp Phe Asp Val
        150                 155                 160 gtg gca cgt gca ata gtt caa att aag aac gct atc gat gct ggc ata       585
Val Ala Arg Ala Ile Val Gln Ile Lys Asn Ala Ile Asp Ala Gly Ile
    165                 170                 175 gag ttg ggc gcc gag aat tac gtt ttc tgg ggt ggc cgt gag ggt tat       633
Glu Leu Gly Ala Glu Asn Tyr Val Phe Trp Gly Gly Arg Glu Gly Tyr
180                 185                 190                 195 atg agc ctt tta aat acg gat caa aaa cgt gag aag gaa cac atg gct       681
Met Ser Leu Leu Asn Thr Asp Gln Lys Arg Glu Lys Glu His Met Ala
                200                 205                 210 aca atg ctt acg atg gcc cgt gac tat gct aga tca aaa ggt ttt aag       729
Thr Met Leu Thr Met Ala Arg Asp Tyr Ala Arg Ser Lys Gly Phe Lys
            215                 220                 225 ggt aca ttc ttg ata gaa cct aaa ccg atg gaa cca aca aag cac caa       777
Gly Thr Phe Leu Ile Glu Pro Lys Pro Met Glu Pro Thr Lys His Gln
        230                 235                 240 tat gat gta gat acc gaa acc gca att gga ttt ttg aag gca cat aac       825
Tyr Asp Val Asp Thr Glu Thr Ala Ile Gly Phe Leu Lys Ala His Asn
    245                 250                 255 ttg gac aag gat ttc aag gta aac ata gaa gta aat cat gca acg ttg       873
Leu Asp Lys Asp Phe Lys Val Asn Ile Glu Val Asn His Ala Thr Leu
```

```
                260              265               270               275
gca ggt cat act ttc gaa cac gaa tta gct tgc gca gta gat gct gga      921
Ala Gly His Thr Phe Glu His Glu Leu Ala Cys Ala Val Asp Ala Gly
                280               285               290 atg tta ggt agc atc gat gca aat aga ggt gat tac cag aat ggc tgg      969
Met Leu Gly Ser Ile Asp Ala Asn Arg Gly Asp Tyr Gln Asn Gly Trp
                295               300               305 gat act gat caa ttc cca ata gac cag tat gaa ctg gta cag gcc tgg     1017
Asp Thr Asp Gln Phe Pro Ile Asp Gln Tyr Glu Leu Val Gln Ala Trp
            310               315               320 atg gaa ata atc cgt ggc ggt ggt ttc gtg aca ggt gga aca aat ttt     1065
Met Glu Ile Ile Arg Gly Gly Gly Phe Val Thr Gly Gly Thr Asn Phe
325               330               335 gat gca aaa act cgt aga aac tca act gat ctt gag gat atc att atc     1113
Asp Ala Lys Thr Arg Arg Asn Ser Thr Asp Leu Glu Asp Ile Ile Ile
340               345               350               355 gct cac gta tct ggc atg gac gct atg gcc cgt gca ttg gag aac gct     1161
Ala His Val Ser Gly Met Asp Ala Met Ala Arg Ala Leu Glu Asn Ala
                360               365               370 gct aag ctt tta caa gag tcc cca tat acg aag atg aag aaa gag aga     1209
Ala Lys Leu Leu Gln Glu Ser Pro Tyr Thr Lys Met Lys Lys Glu Arg
                375               380               385 tat gct tct ttt gat agc ggt ata gga aaa gac ttc gag gat gga aag     1257
Tyr Ala Ser Phe Asp Ser Gly Ile Gly Lys Asp Phe Glu Asp Gly Lys
                390               395               400 ctg aca ctg gag caa gtg tac gaa tat ggt aaa aag aat ggt gaa cca     1305
Leu Thr Leu Glu Gln Val Tyr Glu Tyr Gly Lys Lys Asn Gly Glu Pro
            405               410               415 aaa cag acc tca gga aag cag gaa tta tat gaa gcc att gtg gct atg     1353
Lys Gln Thr Ser Gly Lys Gln Glu Leu Tyr Glu Ala Ile Val Ala Met
420               425               430               435 tac caa tagcctaggc tcgaggaatt c                                     1380
Tyr Gln <210> SEQ ID NO 3
<211> LENGTH: 1383
<212> TYPE: DNA
<213> ORGANISM: Artificial Sequence
<220> FEATURE:
<223> OTHER INFORMATION: Synthetic construct (ThXI)
<220> FEATURE:
<221> NAME/KEY: CDS
<222> LOCATION: (49)..(1362)

<400> SEQUENCE: 3
gaattcctag aaataatttt gtttaacttt aagaaggagg agctagcc atg gaa tat      57
                                                    Met Glu Tyr
                                                    1 ttc aaa aac gtg cca cag atc aag tat gaa ggt cct aaa agc aat aac     105
Phe Lys Asn Val Pro Gln Ile Lys Tyr Glu Gly Pro Lys Ser Asn Asn
  5               10               15 cct tat gca ttt aag ttc tat aac cca gat gaa att ata gat gga aaa     153
Pro Tyr Ala Phe Lys Phe Tyr Asn Pro Asp Glu Ile Ile Asp Gly Lys
20               25               30               35 cca tta aaa gaa cac tta aga ttt agc gta gcc tac tgg cat aca ttt     201
Pro Leu Lys Glu His Leu Arg Phe Ser Val Ala Tyr Trp His Thr Phe
                40               45               50 acc gct aac gga acg gat cca ttt ggt gca ccg act atg cag cgt cct     249
Thr Ala Asn Gly Thr Asp Pro Phe Gly Ala Pro Thr Met Gln Arg Pro
            55               60               65 tgg gat cat ttt acc gac cct atg gac ata gca aaa gca cgt gtg gaa     297
Trp Asp His Phe Thr Asp Pro Met Asp Ile Ala Lys Ala Arg Val Glu
```

|  |  |  |  |  |  |  |  |  |  |  |  |  |  |  |  |
|---|---|---|---|---|---|---|---|---|---|---|---|---|---|---|---|
|  | Trp | Asp | His | Phe | Thr | Asp | Pro | Met | Asp | Ile | Ala | Lys | Ala | Arg | Val | Glu |
|  |  | 70 |  |  |  | 75 |  |  |  |  | 80 |  |  |  |  |  |

| gcc | gca | ttc | gag | ctt | ttt | gaa | aaa | ttg | gat | gtt | cca | ttc | ttc | tgt | ttt | 345 |
|---|---|---|---|---|---|---|---|---|---|---|---|---|---|---|---|---|
| Ala | Ala | Phe | Glu | Leu | Phe | Glu | Lys | Leu | Asp | Val | Pro | Phe | Phe | Cys | Phe |  |
| 85 |  |  |  |  | 90 |  |  |  |  | 95 |  |  |  |  |  |  |

| cat | gac | aga | gat | ata | gct | ccg | gaa | ggt | gaa | aca | ttg | aga | gaa | acc | aac | 393 |
|---|---|---|---|---|---|---|---|---|---|---|---|---|---|---|---|---|
| His | Asp | Arg | Asp | Ile | Ala | Pro | Glu | Gly | Glu | Thr | Leu | Arg | Glu | Thr | Asn |  |
| 100 |  |  |  | 105 |  |  |  |  | 110 |  |  |  |  | 115 |  |  |

| aaa | aac | tta | gat | act | atc | gtt | gct | atg | att | aaa | gac | tac | tta | aaa | acg | 441 |
|---|---|---|---|---|---|---|---|---|---|---|---|---|---|---|---|---|
| Lys | Asn | Leu | Asp | Thr | Ile | Val | Ala | Met | Ile | Lys | Asp | Tyr | Leu | Lys | Thr |  |
|  |  |  | 120 |  |  |  |  | 125 |  |  |  |  | 130 |  |  |  |

| tca | aag | act | aaa | gtt | ctt | tgg | ggc | act | gct | aat | ttg | ttt | tct | aat | cca | 489 |
|---|---|---|---|---|---|---|---|---|---|---|---|---|---|---|---|---|
| Ser | Lys | Thr | Lys | Val | Leu | Trp | Gly | Thr | Ala | Asn | Leu | Phe | Ser | Asn | Pro |  |
|  |  | 135 |  |  |  |  | 140 |  |  |  |  | 145 |  |  |  |  |

| cgt | ttc | gtg | cat | ggc | gct | gcc | aca | tca | tgt | aat | gca | gac | gta | ttt | gct | 537 |
|---|---|---|---|---|---|---|---|---|---|---|---|---|---|---|---|---|
| Arg | Phe | Val | His | Gly | Ala | Ala | Thr | Ser | Cys | Asn | Ala | Asp | Val | Phe | Ala |  |
|  | 150 |  |  |  |  | 155 |  |  |  |  | 160 |  |  |  |  |  |

| tat | gca | gcc | gct | caa | gtt | aaa | aag | gcc | tta | gag | att | acc | aaa | gag | tta | 585 |
|---|---|---|---|---|---|---|---|---|---|---|---|---|---|---|---|---|
| Tyr | Ala | Ala | Ala | Gln | Val | Lys | Lys | Ala | Leu | Glu | Ile | Thr | Lys | Glu | Leu |  |
| 165 |  |  |  |  | 170 |  |  |  |  | 175 |  |  |  |  |  |  |

| gga | ggc | cag | aat | tat | gtt | ttc | tgg | ggt | ggt | cgt | gag | gga | tat | gag | aca | 633 |
|---|---|---|---|---|---|---|---|---|---|---|---|---|---|---|---|---|
| Gly | Gly | Gln | Asn | Tyr | Val | Phe | Trp | Gly | Gly | Arg | Glu | Gly | Tyr | Glu | Thr |  |
| 180 |  |  |  |  | 185 |  |  |  |  | 190 |  |  |  |  | 195 |  |

| ctt | tta | aat | act | gat | atg | gag | ttg | gaa | tta | gat | aat | tta | gca | aga | ttc | 681 |
|---|---|---|---|---|---|---|---|---|---|---|---|---|---|---|---|---|
| Leu | Leu | Asn | Thr | Asp | Met | Glu | Leu | Glu | Leu | Asp | Asn | Leu | Ala | Arg | Phe |  |
|  |  |  | 200 |  |  |  |  | 205 |  |  |  |  | 210 |  |  |  |

| tta | cac | atg | gca | gta | gaa | tat | gct | cag | gaa | att | ggt | ttt | gaa | gga | cag | 729 |
|---|---|---|---|---|---|---|---|---|---|---|---|---|---|---|---|---|
| Leu | His | Met | Ala | Val | Glu | Tyr | Ala | Gln | Glu | Ile | Gly | Phe | Glu | Gly | Gln |  |
|  |  | 215 |  |  |  |  | 220 |  |  |  |  | 225 |  |  |  |  |

| ttc | ttg | atc | gag | cct | aaa | cca | aag | gaa | cca | aca | aag | cat | cag | tat | gat | 777 |
|---|---|---|---|---|---|---|---|---|---|---|---|---|---|---|---|---|
| Phe | Leu | Ile | Glu | Pro | Lys | Pro | Lys | Glu | Pro | Thr | Lys | His | Gln | Tyr | Asp |  |
|  | 230 |  |  |  |  | 235 |  |  |  |  | 240 |  |  |  |  |  |

| ttc | gac | gct | gct | tct | gta | cac | gcc | ttt | ttg | aag | aag | tat | gat | ttg | gat | 825 |
|---|---|---|---|---|---|---|---|---|---|---|---|---|---|---|---|---|
| Phe | Asp | Ala | Ala | Ser | Val | His | Ala | Phe | Leu | Lys | Lys | Tyr | Asp | Leu | Asp |  |
| 245 |  |  |  |  | 250 |  |  |  |  | 255 |  |  |  |  |  |  |

| aaa | tac | ttt | aag | ttg | aac | ata | gag | gct | aat | cac | gca | acg | ttg | gca | ggt | 873 |
|---|---|---|---|---|---|---|---|---|---|---|---|---|---|---|---|---|
| Lys | Tyr | Phe | Lys | Leu | Asn | Ile | Glu | Ala | Asn | His | Ala | Thr | Leu | Ala | Gly |  |
| 260 |  |  |  |  | 265 |  |  |  |  | 270 |  |  |  |  | 275 |  |

| cac | gat | ttt | caa | cac | gaa | ttg | aga | tac | gcc | cgt | att | aat | aac | atg | tta | 921 |
|---|---|---|---|---|---|---|---|---|---|---|---|---|---|---|---|---|
| His | Asp | Phe | Gln | His | Glu | Leu | Arg | Tyr | Ala | Arg | Ile | Asn | Asn | Met | Leu |  |
|  |  |  | 280 |  |  |  |  | 285 |  |  |  |  | 290 |  |  |  |

| ggt | tcc | ata | gat | gcc | aac | atg | ggt | gac | atg | ttg | ctg | ggt | tgg | gat | act | 969 |
|---|---|---|---|---|---|---|---|---|---|---|---|---|---|---|---|---|
| Gly | Ser | Ile | Asp | Ala | Asn | Met | Gly | Asp | Met | Leu | Leu | Gly | Trp | Asp | Thr |  |
|  |  | 295 |  |  |  |  | 300 |  |  |  |  | 305 |  |  |  |  |

| gat | caa | tac | cca | acg | gat | att | aga | atg | aca | act | tta | gca | atg | tac | gag | 1017 |
|---|---|---|---|---|---|---|---|---|---|---|---|---|---|---|---|---|
| Asp | Gln | Tyr | Pro | Thr | Asp | Ile | Arg | Met | Thr | Thr | Leu | Ala | Met | Tyr | Glu |  |
|  | 310 |  |  |  |  | 315 |  |  |  |  | 320 |  |  |  |  |  |

| gtc | att | aaa | atg | gga | ggt | ttt | aac | aaa | gga | ggt | ttg | aat | ttc | gat | gct | 1065 |
|---|---|---|---|---|---|---|---|---|---|---|---|---|---|---|---|---|
| Val | Ile | Lys | Met | Gly | Gly | Phe | Asn | Lys | Gly | Gly | Leu | Asn | Phe | Asp | Ala |  |
| 325 |  |  |  |  | 330 |  |  |  |  | 335 |  |  |  |  |  |  |

| aaa | gtg | cgt | cgt | gcc | tct | ttt | gaa | cct | gaa | gac | ctt | ttt | ctt | gga | cat | 1113 |
|---|---|---|---|---|---|---|---|---|---|---|---|---|---|---|---|---|
| Lys | Val | Arg | Arg | Ala | Ser | Phe | Glu | Pro | Glu | Asp | Leu | Phe | Leu | Gly | His |  |
| 340 |  |  |  |  | 345 |  |  |  |  | 350 |  |  |  |  | 355 |  |

| att | gcc | gga | atg | gat | gca | ttt | gca | aaa | ggt | ttc | aag | gtc | gct | tat | aag | 1161 |
|---|---|---|---|---|---|---|---|---|---|---|---|---|---|---|---|---|
| Ile | Ala | Gly | Met | Asp | Ala | Phe | Ala | Lys | Gly | Phe | Lys | Val | Ala | Tyr | Lys |  |
|  |  |  | 360 |  |  |  |  | 365 |  |  |  |  | 370 |  |  |  |

| ctt | gtt | aag | gat | ggt | gta | ttt | gat | aga | ttc | att | gaa | gag | aga | tac | aaa | 1209 |
|---|---|---|---|---|---|---|---|---|---|---|---|---|---|---|---|---|
| Leu | Val | Lys | Asp | Gly | Val | Phe | Asp | Arg | Phe | Ile | Glu | Glu | Arg | Tyr | Lys |  |
|  |  | 375 |  |  |  |  | 380 |  |  |  |  | 385 |  |  |  |  |

```
tcc tat cgt gaa ggt ata ggt gct gaa atc gtt tca ggt aag gcc aat    1257
Ser Tyr Arg Glu Gly Ile Gly Ala Glu Ile Val Ser Gly Lys Ala Asn
        390                 395                 400 ttt aag act tta gag gaa tat gca ttg aat aac cca aaa atc gaa aac    1305
Phe Lys Thr Leu Glu Glu Tyr Ala Leu Asn Asn Pro Lys Ile Glu Asn
    405                 410                 415 aaa agc ggt aaa cag gaa ctg ctg gaa tct att ttg aat caa tat ttg    1353
Lys Ser Gly Lys Gln Glu Leu Leu Glu Ser Ile Leu Asn Gln Tyr Leu
420                 425                 430                 435 ttc tct gaa tagcctaggc tcgaggaatt c                                1383
Phe Ser Glu
```

```
<210> SEQ ID NO 4
<211> LENGTH: 40
<212> TYPE: DNA
<213> ORGANISM: Artificial Sequence
<220> FEATURE:
<223> OTHER INFORMATION: Primer

<400> SEQUENCE: 4
gctagccatg ccactaccc catttgatgc tccagataag                          40

<210> SEQ ID NO 5
<211> LENGTH: 43
<212> TYPE: DNA
<213> ORGANISM: Artificial Sequence
<220> FEATURE:
<223> OTHER INFORMATION: Primer

<400> SEQUENCE: 5
ctcgagccta ggctagtgtt tcaattcact ttccatcttg gcc                     43

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gctagccatg gcttctatta agttgaactc tggttacg                           38

<210> SEQ ID NO 7
<211> LENGTH: 44
<212> TYPE: DNA
<213> ORGANISM: Artificial Sequence
<220> FEATURE:
<223> OTHER INFORMATION: Primer

<400> SEQUENCE: 7
ctcgagccta ggctagacga agataggaat cttgtcccag tccc                    44

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
gctagccatg gctgctaacc cttccttggt gttg                               34

<210> SEQ ID NO 9
<211> LENGTH: 49
<212> TYPE: DNA
```

```
<213> ORGANISM: Artificial Sequence
<220> FEATURE:
<223> OTHER INFORMATION: Primer

<400> SEQUENCE: 9
ctcgagccta ggctactcag ggccgtcaat gagacacttg acagcaccc        49

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
tagctagcat gttatcagta cctgattatg ag                          32

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
atctcgagtt actttaagaa tgccttagtc atgcc                       35

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
tagctagcat gaatttagtt gaaacagccc aagc                        34

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
atctcgagct aatatttgat tgcttgccca gcc                         33

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14
tagctagcat gctagaagca ttaaaacaag aag                         33

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
atctcgagtt acttgcgaac tgcatgatcc ttag                        34
```

```
<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
tagctagcat gacagctcag ttacaaagtg aaag                                34

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
atctcgagtc aggaaaatct gtagacaatc ttgg                                34

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18
tagctagcat ggccagattt tccgctgaag atatgcg                             37

<210> SEQ ID NO 19
<211> LENGTH: 37
<212> TYPE: DNA
<213> ORGANISM: Artificial Sequence
<220> FEATURE:
<223> OTHER INFORMATION: Primer

<400> SEQUENCE: 19
tagtttaaac ttgccatcat cattccctag aaactgc                             37

<210> SEQ ID NO 20
<211> LENGTH: 33
<212> TYPE: DNA
<213> ORGANISM: Artificial Sequence
<220> FEATURE:
<223> OTHER INFORMATION: Primer

<400> SEQUENCE: 20
tagtcgacag tgtgtaagag tgtaccattt act                                 33

<210> SEQ ID NO 21
<211> LENGTH: 34
<212> TYPE: DNA
<213> ORGANISM: Artificial Sequence
<220> FEATURE:
<223> OTHER INFORMATION: Primer

<400> SEQUENCE: 21
tactcgagtt tcccttttc tgccttttc ggtg                                  34

<210> SEQ ID NO 22
<211> LENGTH: 34
<212> TYPE: DNA
<213> ORGANISM: Artificial Sequence
<220> FEATURE:
```

```
<223> OTHER INFORMATION: Primer

<400> SEQUENCE: 22
tagtttaaac tgatggtgtg aagacatag atgg                                    34

<210> SEQ ID NO 23
<211> LENGTH: 40
<212> TYPE: DNA
<213> ORGANISM: Artificial Sequence
<220> FEATURE:
<223> OTHER INFORMATION: Primer

<400> SEQUENCE: 23
tagtttaaac agttatgttt aaaaaatcaa ctttctttcc                              40

<210> SEQ ID NO 24
<211> LENGTH: 33
<212> TYPE: DNA
<213> ORGANISM: Artificial Sequence
<220> FEATURE:
<223> OTHER INFORMATION: Primer

<400> SEQUENCE: 24
tagtcgacaa ccaggtcctt gtgtgccgct gtt                                    33

<210> SEQ ID NO 25
<211> LENGTH: 32
<212> TYPE: DNA
<213> ORGANISM: Artificial Sequence
<220> FEATURE:
<223> OTHER INFORMATION: Primer

<400> SEQUENCE: 25
tactcgagtc ctatcgagtt acactgctag tg                                     32

<210> SEQ ID NO 26
<211> LENGTH: 36
<212> TYPE: DNA
<213> ORGANISM: Artificial Sequence
<220> FEATURE:
<223> OTHER INFORMATION: Primer

<400> SEQUENCE: 26
tagtttaaac attgcttagc atagctgcca ctaacc                                 36

<210> SEQ ID NO 27
<211> LENGTH: 35
<212> TYPE: DNA
<213> ORGANISM: Artificial Sequence
<220> FEATURE:
<223> OTHER INFORMATION: Primer

<400> SEQUENCE: 27
tagtcgactg acatgtatgg gttgaaaata tttag                                  35

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
tacctaggtt ttaggctggt atcttgattc                                        30
```

```
<210> SEQ ID NO 29
<211> LENGTH: 33
<212> TYPE: DNA
<213> ORGANISM: Artificial Sequence
<220> FEATURE:
<223> OTHER INFORMATION: Primer

<400> SEQUENCE: 29
tagtcgactg tttaaagatt acggatattt aac                                    33

<210> SEQ ID NO 30
<211> LENGTH: 36
<212> TYPE: DNA
<213> ORGANISM: Artificial Sequence
<220> FEATURE:
<223> OTHER INFORMATION: Primer

<400> SEQUENCE: 30
tacctaggtt ttagtttatg tatgtgtttt ttgtag                                 36

<210> SEQ ID NO 31
<211> LENGTH: 35
<212> TYPE: DNA
<213> ORGANISM: Artificial Sequence
<220> FEATURE:
<223> OTHER INFORMATION: Primer

<400> SEQUENCE: 31
tagtcgacaa aaggtctaac atcctttgag ttatg                                  35

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
tacctagggt tatgttaact tttgttactt                                        30

<210> SEQ ID NO 33
<211> LENGTH: 33
<212> TYPE: DNA
<213> ORGANISM: Artificial Sequence
<220> FEATURE:
<223> OTHER INFORMATION: Primer

<400> SEQUENCE: 33
tagtcgacag ggtagcctcc ccataacata aac                                    33

<210> SEQ ID NO 34
<211> LENGTH: 37
<212> TYPE: DNA
<213> ORGANISM: Artificial Sequence
<220> FEATURE:
<223> OTHER INFORMATION: Primer

<400> SEQUENCE: 34
tacctaggtt tgattgattt gactgtgtta ttttgcg                                37

<210> SEQ ID NO 35
<211> LENGTH: 31
<212> TYPE: DNA
<213> ORGANISM: Artificial Sequence
<220> FEATURE:
<223> OTHER INFORMATION: Primer
```

<400> SEQUENCE: 35
tagtcgacat aacaatactg acagtactaa a                                31

<210> SEQ ID NO 36
<211> LENGTH: 34
<212> TYPE: DNA
<213> ORGANISM: Artificial Sequence
<220> FEATURE:
<223> OTHER INFORMATION: Primer

<400> SEQUENCE: 36
tacctaggtt tgaatatgta ttacttggtt atgg                             34

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
tagtcgacca catgcagtga tgcacgcgcg                                  30

<210> SEQ ID NO 38
<211> LENGTH: 33
<212> TYPE: DNA
<213> ORGANISM: Artificial Sequence
<220> FEATURE:
<223> OTHER INFORMATION: Primer

<400> SEQUENCE: 38
tacctaggta ttgtaatatg tgtgtttgtt tgg                              33

<210> SEQ ID NO 39
<211> LENGTH: 36
<212> TYPE: DNA
<213> ORGANISM: Artificial Sequence
<220> FEATURE:
<223> OTHER INFORMATION: Primer

<400> SEQUENCE: 39
tatctagaat gactcaattc actgacattg ataagc                           36

<210> SEQ ID NO 40
<211> LENGTH: 39
<212> TYPE: DNA
<213> ORGANISM: Artificial Sequence
<220> FEATURE:
<223> OTHER INFORMATION: Primer

<400> SEQUENCE: 40
tactcgagtt agaaagcttt tttcaaagga gaaattagc                        39

<210> SEQ ID NO 41
<211> LENGTH: 33
<212> TYPE: DNA
<213> ORGANISM: Artificial Sequence
<220> FEATURE:
<223> OTHER INFORMATION: Primer

<400> SEQUENCE: 41
tagctagcat gttgtgttca gtaattcaga gac                              33

<210> SEQ ID NO 42
<211> LENGTH: 31

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
atctcgagga tgagagtctt ttccagttcg c         31

<210> SEQ ID NO 43
<211> LENGTH: 38
<212> TYPE: DNA
<213> ORGANISM: Artificial Sequence
<220> FEATURE:
<223> OTHER INFORMATION: Primer

<400> SEQUENCE: 43
gctagccatg tctgaaccag ctcaaaagaa acaaaagg         38

<210> SEQ ID NO 44
<211> LENGTH: 34
<212> TYPE: DNA
<213> ORGANISM: Artificial Sequence
<220> FEATURE:
<223> OTHER INFORMATION: Primer

<400> SEQUENCE: 44
tactcgagag aaactgtatc attcatcaaa tagg         34

<210> SEQ ID NO 45
<211> LENGTH: 37
<212> TYPE: DNA
<213> ORGANISM: Artificial Sequence
<220> FEATURE:
<223> OTHER INFORMATION: Primer

<400> SEQUENCE: 45
gctagccatg gctgccggtg tcccaaaaat tgatgcg         37

<210> SEQ ID NO 46
<211> LENGTH: 34
<212> TYPE: DNA
<213> ORGANISM: Artificial Sequence
<220> FEATURE:
<223> OTHER INFORMATION: Primer

<400> SEQUENCE: 46
tactcgagaa cattgcattt attggtgttg aatc         34

<210> SEQ ID NO 47
<211> LENGTH: 335
<212> TYPE: PRT
<213> ORGANISM: Artificial Sequence
<220> FEATURE:
<223> OTHER INFORMATION: Synthetic construct (L1MR)

<400> SEQUENCE: 47

Met Ala Thr Phe Thr Ile Ser Lys Glu Ser Leu Pro Phe Arg Ala Asp
1               5                   10                  15

Lys Ser Ile Ser Gln Ile Thr Leu Ser Asn Glu Arg Leu Thr Ile Val
            20                  25                  30

Val His Asp Tyr Gly Ala Arg Ala His Gln Leu Leu Thr Pro Asp Lys
        35                  40                  45

Asn Gly Thr Phe Glu Asn Ile Leu Leu Ser Lys Asn Asp Ser Glu Thr
    50                  55                  60

-continued

Tyr Ala Asn Asp Gly Tyr Tyr Gly Val Ile Cys Gly Pro Val Ala
65              70                  75                  80

Gly Arg Ile Ser Gly Ala Thr Tyr Asp Ser Val Ser Leu Glu Ala Asn
            85                  90                  95

Glu Gly Lys Asn Asn Leu His Ser Gly Ser His Gly Trp Glu Arg Gln
        100                 105                 110

Phe Trp Ser Tyr Glu Thr Phe Glu Thr Ala Ser Ser Leu Gly Ile Lys
    115                 120                 125

Leu Ser Leu Arg Asp Glu Glu Ser Gly Phe Pro Gly Gln Ile Gln Ala
130                 135                 140

Glu Val Thr Tyr Lys Leu Thr Asp Asn Lys Leu Glu Val Thr Ile Ser
145                 150                 155                 160

Gly Leu Ser Val Thr Asp Thr Val Phe Asn Pro Ala Trp His Pro Tyr
                165                 170                 175

Phe Asn Leu Ser Ala Glu Leu Ser Thr Thr His Glu His Phe Ile Gln
                180                 185                 190

Ala Asn Val Asp Phe Leu Val Glu Thr Asn Gln Glu Asn Ile Pro Thr
            195                 200                 205

Gly Arg Leu Leu Thr Val Asp Asp Ser Ser Tyr Ser Ile Lys Glu Ser
210                 215                 220

Val Ser Ile Lys Lys Leu Leu Lys Asp Asn Pro Glu Gly Leu Asp Asp
225                 230                 235                 240

Cys Phe Val Phe Asn Pro Lys Gly Asp Lys Ser Leu Met Leu Tyr Asp
                245                 250                 255

Pro Leu Ser Gly Arg Lys Leu Val Ala Gln Thr Asp Arg Gln Ala Val
                260                 265                 270

Val Ile Tyr Thr Ala Thr Asn Pro Glu Ile Glu Ser Met Ile Asn Gly
            275                 280                 285

Arg Pro Met Ser Lys Asn Arg Gly Ile Ala Ile Glu Phe Gln Glu Ile
        290                 295                 300

Pro Asp Leu Val His His Pro Gly Trp Gly Thr Ile Glu Leu Lys Ala
305                 310                 315                 320

Gly Gln Lys Lys Thr Phe Ile Thr Glu Tyr Leu Phe Thr Thr Asn
                325                 330                 335

<210> SEQ ID NO 48
<211> LENGTH: 437
<212> TYPE: PRT
<213> ORGANISM: Artificial Sequence
<220> FEATURE:
<223> OTHER INFORMATION: Synthetic construct (PmXI)

<400> SEQUENCE: 48

Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65              70                  75                  80

Lys Gln Lys Val Asp Ala Gly Phe Glu Ile Met Gln Lys Leu Gly Ile
            85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Gly Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435

<210> SEQ ID NO 49
<211> LENGTH: 438
<212> TYPE: PRT
<213> ORGANISM: Artificial Sequence
<220> FEATURE:
<223> OTHER INFORMATION: Synthetic construct (ThXI)

<400> SEQUENCE: 49

Met Glu Tyr Phe Lys Asn Val Pro Gln Ile Lys Tyr Glu Gly Pro Lys
1               5                   10                  15

```
Ser Asn Asn Pro Tyr Ala Phe Lys Phe Tyr Asn Pro Asp Glu Ile Ile
            20                  25                  30

Asp Gly Lys Pro Leu Lys Glu His Leu Arg Phe Ser Val Ala Tyr Trp
        35                  40                  45

His Thr Phe Thr Ala Asn Gly Thr Asp Pro Phe Gly Ala Pro Thr Met
    50                  55                  60

Gln Arg Pro Trp Asp His Phe Thr Asp Pro Met Asp Ile Ala Lys Ala
65                  70                  75                  80

Arg Val Glu Ala Ala Phe Glu Leu Phe Glu Lys Leu Asp Val Pro Phe
                85                  90                  95

Phe Cys Phe His Asp Arg Asp Ile Ala Pro Glu Gly Glu Thr Leu Arg
                100                 105                 110

Glu Thr Asn Lys Asn Leu Asp Thr Ile Val Ala Met Ile Lys Asp Tyr
            115                 120                 125

Leu Lys Thr Ser Lys Thr Lys Val Leu Trp Gly Thr Ala Asn Leu Phe
    130                 135                 140

Ser Asn Pro Arg Phe Val His Gly Ala Ala Thr Ser Cys Asn Ala Asp
145                 150                 155                 160

Val Phe Ala Tyr Ala Ala Ala Gln Val Lys Lys Ala Leu Glu Ile Thr
                165                 170                 175

Lys Glu Leu Gly Gly Gln Asn Tyr Val Phe Trp Gly Gly Arg Glu Gly
            180                 185                 190

Tyr Glu Thr Leu Leu Asn Thr Asp Met Glu Leu Glu Leu Asp Asn Leu
    195                 200                 205

Ala Arg Phe Leu His Met Ala Val Glu Tyr Ala Gln Glu Ile Gly Phe
210                 215                 220

Glu Gly Gln Phe Leu Ile Glu Pro Lys Pro Lys Glu Pro Thr Lys His
225                 230                 235                 240

Gln Tyr Asp Phe Asp Ala Ala Ser Val His Ala Phe Leu Lys Lys Tyr
                245                 250                 255

Asp Leu Asp Lys Tyr Phe Lys Leu Asn Ile Glu Ala Asn His Ala Thr
            260                 265                 270

Leu Ala Gly His Asp Phe Gln His Glu Leu Arg Tyr Ala Arg Ile Asn
    275                 280                 285

Asn Met Leu Gly Ser Ile Asp Ala Asn Met Gly Asp Met Leu Leu Gly
290                 295                 300

Trp Asp Thr Asp Gln Tyr Pro Thr Asp Ile Arg Met Thr Thr Leu Ala
305                 310                 315                 320

Met Tyr Glu Val Ile Lys Met Gly Gly Phe Asn Lys Gly Gly Leu Asn
                325                 330                 335

Phe Asp Ala Lys Val Arg Arg Ala Ser Phe Glu Pro Glu Asp Leu Phe
            340                 345                 350

Leu Gly His Ile Ala Gly Met Asp Ala Phe Ala Lys Gly Phe Lys Val
    355                 360                 365

Ala Tyr Lys Leu Val Lys Asp Gly Val Phe Asp Arg Phe Ile Glu Glu
370                 375                 380

Arg Tyr Lys Ser Tyr Arg Glu Gly Ile Gly Ala Glu Ile Val Ser Gly
385                 390                 395                 400

Lys Ala Asn Phe Lys Thr Leu Glu Glu Tyr Ala Leu Asn Asn Pro Lys
                405                 410                 415

Ile Glu Asn Lys Ser Gly Lys Gln Glu Leu Leu Glu Ser Ile Leu Asn
            420                 425                 430
```

```
Gln Tyr Leu Phe Ser Glu
        435
```